(12) United States Patent
Dekruyff et al.

(10) Patent No.: US 11,485,787 B2
(45) Date of Patent: Nov. 1, 2022

(54) AGENTS THAT MODULATE RGMB-NEOGENIN-BMP SIGNALING AND METHODS OF USE THEREOF

(71) Applicants: Dana-Farber Cancer Institute, Inc., Boston, MA (US); Boston Children's Hospital, Boston, MA (US)

(72) Inventors: Rosemarie Dekruyff, Newton, MA (US); Gordon J. Freeman, Brookline, MA (US); Dale Umetsu, Newton, CT (US); Sanhong Yu, Brookline, MA (US); Yanping Xiao, Brookline, MA (US)

(73) Assignees: Dana-Farber Cancer Institute, Inc., Boston, MA (US); Boston Children's Hospital, Boston, MA (US)

( * ) Notice: Subject to any disclaimer, the term of this patent is extended or adjusted under 35 U.S.C. 154(b) by 0 days.

(21) Appl. No.: 15/116,321

(22) PCT Filed: Feb. 5, 2015

(86) PCT No.: PCT/US2015/014595
§ 371 (c)(1),
(2) Date: Aug. 3, 2016

(87) PCT Pub. No.: WO2015/120138
PCT Pub. Date: Aug. 13, 2015

(65) Prior Publication Data
US 2016/0347844 A1    Dec. 1, 2016

Related U.S. Application Data

(60) Provisional application No. 61/936,150, filed on Feb. 5, 2014.

(51) Int. Cl.
| | |
|---|---|
| *A61K 39/395* | (2006.01) |
| *C07K 16/28* | (2006.01) |
| *C07K 16/22* | (2006.01) |
| *A61K 31/7105* | (2006.01) |
| *A61K 45/06* | (2006.01) |
| *C12N 15/113* | (2010.01) |
| *C12N 15/115* | (2010.01) |
| *G01N 33/566* | (2006.01) |
| *A61K 39/00* | (2006.01) |

(52) U.S. Cl.
CPC ...... *C07K 16/2863* (2013.01); *A61K 31/7105* (2013.01); *A61K 39/3955* (2013.01); *A61K 45/06* (2013.01); *C07K 16/22* (2013.01); *C07K 16/2803* (2013.01); *C12N 15/115* (2013.01); *C12N 15/1138* (2013.01); *G01N 33/566* (2013.01); *A61K 2039/505* (2013.01); *C07K 2317/565* (2013.01); *C07K 2317/76* (2013.01); *C12N 2310/11* (2013.01); *C12N 2310/14* (2013.01); *C12N 2310/16* (2013.01); *C12N 2320/31* (2013.01); *G01N 2333/715* (2013.01); *G01N 2500/04* (2013.01)

(58) Field of Classification Search
None
See application file for complete search history.

(56) References Cited

U.S. PATENT DOCUMENTS

| | | | | |
|---|---|---|---|---|
| 6,086,898 | A * | 7/2000 | DeKruyff | A61K 39/39 424/275.1 |
| 7,550,472 | B2 * | 6/2009 | Dollinger | C07D 475/08 514/262.1 |
| 9,334,331 | B2 * | 5/2016 | Igawa | C07K 16/40 |
| 10,421,807 | B2 * | 9/2019 | Gonzales | A61P 43/00 |
| 2003/0219839 | A1 * | 11/2003 | Bowdish | C07K 16/22 435/7.9 |
| 2006/0063208 | A1 * | 3/2006 | Woolf | G01N 33/74 435/7.2 |
| 2010/0322948 | A1 | 12/2010 | Mueller et al. | |
| 2011/0003971 | A1 | 1/2011 | Strittmatter et al. | |
| 2012/0245184 | A1 | 9/2012 | Brunton et al. | |
| 2013/0252833 | A1 | 9/2013 | Woolf et al. | |

FOREIGN PATENT DOCUMENTS

| WO | WO-2009/030500 A1 | 3/2009 |
|---|---|---|
| WO | WO-2014/022759 A1 | 2/2014 |

OTHER PUBLICATIONS

"Idiopathic Pulmonary Fibrosis," internet definition accessed Mar. 19, 2018 at https://www.lung.ca/lung-health/lung-disease/idiopathic-pulmonary-fibrosis.*
"What are Crohn's and Colitis" (accessed Sep. 28, 2018 at http://www.crohnscolitisfoundation.org/what-are-crohns-and-colitis/).*
Al Qaraghuli et al. (2020, Nature Scientific Reports 10:13969).*
Edwards et al. (JMB, 2003, 334:103-118).*
Lloyd et al. (Protein Engineering, Eng. Design & Selection, 2009, 22(3): 159-168).*
Goel et al. (J. Immunol., 2004, 173: 7358-7367).*
Andreev et al. (2012, Frontiers in Immunology 3(216):1-13).*
Extended European Search Report for Application No. 15746105.4 dated Jan. 29, 2018.
Conrad et al., "RGMb controls aggregation and migration of Neogenin-positive cells in vitro and in vivo," Mol Cell Neurosci, 43(2):222-231 (2010).
Corradini et al., "The RGM/DRAGON family of BMP co-receptors," Cytokine Growth Factor Rev, 20(0):389-398 (2009).
Hagihara et al., "Neogenin, a receptor for bone morphogenetic proteins," J Biol Chem, 286(7):5157-5165 (2011).
Partial Supplementary European Search Report issued by the European Patent Office in corresponding Application No. EP 15746105.4, dated Oct. 23, 2017.
Bell et al., "Structure of the Repulsive Guidance Molecule (RGM)-Neogenin Signaling Hub," Science, 341:77-80 (2013).

(Continued)

*Primary Examiner* — Elizabeth C. Kemmerer
(74) *Attorney, Agent, or Firm* — Foley Hoag LLP

(57) ABSTRACT

The present invention relates to compositions and methods for the modulation RGMb-Neogenin-BMP signaling.

16 Claims, 14 Drawing Sheets

Specification includes a Sequence Listing.

(56) References Cited

OTHER PUBLICATIONS

Xiao et al., "RGMb is a novel binding partner for PD-L2 and its engagement with PD-L2 promotes respiratory tolerance," J. Exp. Med., 211:943-959 (2014).
International Search Report dated Jun. 15, 2015, from PCT/US2015/014595.
Lu et al., "Pulmonary manifestations of Crohn's disease," World Journal of Gastroenterology, 20(1): 133-141 (2014).
Vadlamudi et al., "Crohn's disease with pulmonary manifestations in children: 2 case reports and review of the literature," Journal of Crohn's and Colitis, 7(3): e85-e92 (2013).

* cited by examiner

I. Genes elevated in inflamed lung, reduced by aRGMb treatment

II. Genes elevated in inflamed lung, partially reduced by aRGMb treatment

III. Genes elevated in inflamed lung, just as with aRGMb treatment

IV. Genes downregulated in inflamed lung, not with aRGMb treatment

AGENTS THAT MODULATE RGMB-NEOGENIN-BMP SIGNALING AND METHODS OF USE THEREOF

CROSS-REFERENCE TO RELATED APPLICATIONS

This application claims the benefit of U.S. Provisional Application No. 61/936,150, filed on 5 Feb. 2014; the entire contents of said application is incorporated herein in its entirety by this reference.

STATEMENT OF RIGHTS

This invention was made with government support under Grant A1056299 awarded by the National Institutes of Health. The U.S. government has certain rights in the invention. This statement is included solely to comply with 37 C.F.R. § 401.14(a)(f)(4) and should not be taken as an assertion or admission that the application discloses and/or claims only one invention.

BACKGROUND OF THE INVENTION

Repulsive guidance molecule b (RGMb), also known as DRAGON, is a member of the RGM family. RGMs are glycosylphosphatidylinositol (gpi)-anchored membrane proteins that do not directly signal but act as co-receptors, that modulate the activity of signaling receptors. The function of RGMs was originally described in the developing nervous system where they regulate motility and adhesion of neurons and are critical in embryonic development (Samad et al. (2004) *J. Neurosci.* 24:2027-2036 and Matsunaga et al. (2004) *Nat. Cell Biol.* 6:749-755). Co-receptors such as RGMb often have large extracellular domains with multiple motifs enabling them to bind several different ligands. RGMb, a 436 amino acid GPI anchored protein, has been shown to bind neogenin (Bell et al. (2013) *Science* 341:77-80 and Conrad et al. (2009) *Mol. Cell Neurosci.* 43:222-231), bone morphogenetic proteins (BMPs) (Samad et al. (2005) *J. Biol. Chem.* 280:14122-14129 and Xia et al. (2010) *J. Am. Soc. Nephrol.* 21:666-677), and more recently, programmed death ligand 2 (PD-L2).

Neogenin (NEO1) is a critical receptor for axonal guidance and endochondral bone formation (Cole et al. (2007) *Int. J. Biochem. Cell Biol.* 39:1569-1575 and Zhou et al. (2010) *Dev. Cell* 19:90-102) during embryonic development. However, neogenin is abundantly expressed outside the nervous system, and has been shown to promote pulmonary inflammation during lung injury (Mirakaj et al. (2012) *FASEB J.* 26:1549-1558). BMPs, secreted proteins best known for their essential role in regulating bone development (Yoon and Lyons (2004) *J. Cell Biochem.* 93:93-103 and Yoon et al. (2006) *Development* 133:4667-4678), also play essential roles in lung development, and there is some evidence that the BMP/Smad signaling pathway is activated during acute airway inflammation (Rosendahl et al. (2002) *Am. J. Respir. Cell Mol. Biol.* 27:160-169 and Sountoulidis et al. (2012) *PLoS One* 7:e41460). A recent report showed that neogenin regulates the activation of BMPs, and that RGMs mediate interaction of neogenin with BMP receptors, indicating the related pathways of these molecules (Zhou et al. (2010) *Dev. Cell* 19:90-102). It has also recently been shown that RGMb is expressed in lung where it binds PD-L2 and plays a role in induction of respiratory tolerance (Xiao et al. (2014) *J. Exp. Med.* 211:943-959).

Despite the role of the RGMb-NEO1-BMP signaling pathway in regulating developmental processes, its role, if any, in regulating immunological conditions such as those mediated by inflammatory response remains unknown. In particular, allergic asthma is an immunological disease associated with Type 2 immune responses and characterized by inflammation in the peribronchial space and by airway hyperreactivity (AHR), a cardinal feature of asthma. Recent studies have demonstrated the key role of the epithelial cell-derived Type 2 inflammation-associated cytokine IL-25 in driving allergic asthma. IL-25 is critical for allergic asthma, since blockade (Ballantyne et al. (2007) *J. Allerg. Clin. Immunol.* 120:1324-1331) or deficiency (Suzukawa et al. (2012)*J. Immunol.* 189:3641-3652) of IL-25 or the IL-25 receptor (Rickel et al. (2008) *J. Immunol.* 181:4299-4310) prevents the development of AHR in murine models. In humans, increased expression of IL-25 and its receptor has been noted in the airways following allergen exposure. IL-25 produced by airway epithelial cells, mast cells and eosinophils, acts upstream of type 2 cytokines in the development of AHR. Thus, binding of IL-25 to its receptor promotes production of the effector cytokines IL-4, IL-5 and IL-13 by multiple cell types in the inflamed lung, orchestrating many of the classical features of asthma. However, little is known about other molecules that may regulate the inflammatory cascade associated with binding of IL-25 to its receptor. Moreover, inflammatory-mediated diseases represent a large unmet medical need and new targets for modulating such diseases are required.

SUMMARY OF THE INVENTION

The present invention is based, at least in part, on the discovery that the RGMb-NEO1-BMP signaling pathway is critical for the regulation of respiratory inflammatory disorders such as asthma. It was surprisingly discovered that blockade of the RGMb-NEO1-BMP signaling pathway can actually reverse the effects of such respiratory inflammatory disorders at the effector stage once the inflammatory processes are set in motion, as opposed to simply blocking or reducing sensitization to a source of inflammation such as an allergen. For example, blockade of RGMb function by continuous treatment with an anti-RGMb mAb prevented the development of allergen-induced airway hyperreactivity (AHR). Importantly, treatment only during the challenge phase effectively prevented AHR, whereas treatment during the sensitization phase did not prevent T cell priming. These results indicate that anti-RGMb treatment may be effective in reversing established airways disease even after allergen sensitization, and that RGMb functions late during the effector stage of AHR. Using mAbs to NEO and to the IL-25 receptor (IL-17RB), it was also determined that RGMb is coexpressed with NEO on F4/80$^+$CD11b$^+$IL-17RB$^+$ myeloid cells (termed T2M cells), which accumulate in the lungs of mice sensitized and challenged with OVA and contribute to the pathology of asthma. Although PD-L2 is also a ligand of RGMb, it was found that the function of RGMb in modulating AHR was independent of PD-L2. RGMb expressed in the inflamed lung binds NEO and BMPs, resulting in the release of cytokines that trigger AHR. The results described herein indicate that activation of the RGMb-BMP-NEO1 pathway is critical in the inflammation associated with AHR, and that blocking this pathway allows for practical and sustained treatment of respiratory inflammatory disorders in contrast to the chronic application of current therapeutics like bronchodilators or tolerizing agents.

In one aspect, a method of treating a subject having a respiratory inflammatory disorder comprising administering to the subject a therapeutically effective amount of at least one agent that inhibits the repulsive guidance molecule b (RGMb)-neogenin (NEO1)-bone morphogenetic protein (BMP) signaling pathway to thereby treat the respiratory disorder is provided. In one embodiment, the agent is selected from the group consisting of: a blocking antibody that binds RGMb, NEO1, BMP2, and/or BMP4; a non-activating form of RGMb, NEO1, BMP2, and/or BMP4; a soluble form of RGMb, NEO1, BMP2, and/or BMP4; an RGMb, NEO1, BMP2, and/or BMP4 fusion protein; a nucleic acid molecule that blocks transcription or translation of RGMb, NEO1. BMP2, and/or BMP4; and a small molecule antagonist of RGMb, NEO1, BMP2, and/or BMP4. In another embodiment, the blocking antibody is selected from the group consisting of 1) anti-RGMb antibodies that block the interaction between a BMP and RGMb without blocking the interaction between PD-L2 and RGMb, 2) anti-RGMb antibodies that block the interaction between NEO1 and RGMb without blocking the interaction between PD-L2 and RGMb, 3) anti-RGMb antibodies that block both the BMP/RGMb interaction and NEO1/RGMb interaction and without blocking the interaction between PD-L2 and RGMb, 4) anti-RGMb antibodies that block the interaction between a BMP and RGMb and block the interaction between PD-L2 and RGMb, 5) anti-RGMb antibodies that block the interaction between NEO1 and RGMb and block the interaction between PD-L2 and RGMb, and 6) anti-RGMb antibodies that block both the BMP/RGMb interaction and NEO1/RGMb interaction and further block the interaction between PD-L2 and RGMb.

In some embodiments, the antibody, or antigen binding fragment thereof, is murine, chimeric, humanized, composite, or human. In yet another embodiment, the antibody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In another embodiment, the antibody, or antigen binding fragment thereof, is conjugated to a heterologous agent (e.g., a biologic agent, a toxin, and a radioactive isotope). In still another embodiment, the agent comprises an RNA interfering agent which inhibits expression of RGMb, NEO1, BMP2, and/or BMP4 (e.g., a small interfering RNA (siRNA), small hairpin RNA (shRNA), or a microRNA (miRNA)). In yet another embodiment, the agent comprises an antisense oligonucleotide complementary to RGMb. NEO1, BMP2, and/or BMP4. In another embodiment, the agent comprises a peptide or peptidomimetic that inhibits or blocks RGMb, NEO1, BMP2, and/or BMP4. In still another embodiment, the agent comprises a small molecule that inhibits or blocks RGMb, NEO1, BMP2, and/or BMP4 (e.g., a small molecule that inhibits a protein-protein interaction between RGMb and BMP2, RGMb and BMP4, and/or RGMb and NEO1). In yet another embodiment, the agent comprises an aptamer that inhibits or blocks RGMb, NEO1, BMP2, and/or BMP4. In another embodiment, the at least one agent is administered in a pharmaceutically acceptable formulation. In still another embodiment, the respiratory inflammatory disorder is selected from the group consisting of allergic asthma, non-allergic asthma, respiratory allergy, chronic obstructive pulmonary disease (COPD), emphysema, chronic bronchitis, chronic sinusitis, rhinitis, lung infection, cystic fibrosis, interstitial fibrosis, nasal and sinus dysplasia, bronchopulmonary dysplasia and neoplasia, food allergies, Crohn's disease, and inflammatory bowel disease.

In yet another embodiment, the method further comprises administering to the subject an additional therapeutic agent for treating the respiratory inflammatory disorder (e.g., agents selected from the group consisting of bronchodilators, corticosteroids, glucocorticoids, mast-cell stabilizers, oxygen, cytokine inhibitors, immunomodulatory inhibitors, and leukotriene inhibitors, anticholinergic agents, antihistamines, and IgE inhibitors). In another embodiment, the at least one agent is administered systemically, orally, nasally, or pulmonarily. In still another embodiment, the subject is a mammal, such as a human or an animal model of the respiratory inflammatory disorder. In yet another embodiment, the subject has an observable reduction in or absence of one or more of the following: acute hypersreactivity (AHR), recurrent wheezing, coughing, trouble breathing, chest tightness, symptoms that occur or worsen at night, symptoms that are triggered by cold air, exercise or exposure to allergens, upregulated serum IgE (atopy), eosinophilia, and excessive mucus secretion.

In another aspect, a cell-based method for screening for compounds which treat a respiratory inflammatory disorder by modulating RGMb-NEO1-BMP signaling comprising contacting a cell expressing RGMb protein with a NEO1, BMP2, and/or BMP4 protein, and a test compound, and determining the ability of the test compound to 1) modulate the binding between the RGMb protein and the NEO1, BMP2, and/or BMP4 protein and 2) modulate one or more respiratory inflammatory disorder symptoms selected from the group consisting of AHR, recurrent wheezing, coughing, trouble breathing, chest tightness, symptoms that occur or worsen at night, symptoms that are triggered by cold air, exercise or exposure to allergens, upregulated serum IgE (atopy), eosinophilia, and excessive mucus secretion in a subject, wherein a test compound that modulates the binding of the proteins and symptoms treats the respiratory inflammatory disorder is provided. In one embodiment, the cell is an immune cell selected from the group consisting of a T cell, a B cell, and a myeloid cell.

In still another aspect, a cell-based method for screening for compounds which treat a respiratory inflammatory disorder by modulating RGMb-NEO1-BMP signaling comprising contacting a cell expressing NEO1 with a RGMb, BMP2, and/or BMP4 protein, and a test compound, and a test compound and determining the ability of the test compound to 1) modulate the binding between the RGMb protein and the NEO1, BMP2, and/or BMP4 protein and 2) modulate one or more respiratory inflammatory disorder symptoms selected from the group consisting of AHR, recurrent wheezing, coughing, trouble breathing, chest tightness, symptoms that occur or worsen at night, symptoms that are triggered by cold air, exercise or exposure to allergens, upregulated serum IgE (atopy), eosinophilia, and excessive mucus secretion in a subject, wherein a test compound that modulates the binding of the proteins and symptoms treats the respiratory inflammatory disorder is provided. In one embodiment, the cell is an immune cell selected from the group consisting of a T cell, a B cell, and a myeloid cell.

In yet another aspect, a cell-free method for screening for compounds which treat a respiratory inflammatory disorder by modulating RGMb-NEO1-BMP signaling comprising contacting a RGMb, NEO1, BMP2, and/or BMP4 protein with at least one of the protein's natural binding partners selected from the group consisting of RGMb, NEO1, BMP2, and/or BMP4 protein, and a test compound, and determining the ability of the test compound to 1) modulate the binding between the protein(s) and 2) modulate one or more respiratory inflammatory disorder symptoms selected from the group consisting of AHR, recurrent wheezing, coughing, trouble breathing, chest tightness, symptoms that occur or worsen at night, symptoms that are triggered by cold air, exercise or exposure to allergens, upregulated serum IgE (atopy), eosinophilia, and excessive mucus secretion in a subject, wherein a test compound that modulates the binding between the protein(s) and symptoms treats the respiratory inflammatory disorder is provided.

In another aspect, a method of assessing the efficacy of an agent for treating a respiratory inflammatory disorder, comprising: a) detecting in a first subject sample and maintained in the presence of the agent the presence, absence, amount, or activity of at least one biomarker listed in Table 1; b) detecting the presence, absence, amount, or activity of the at least one biomarker listed in Table 1 in a second subject sample and maintained in the absence of the test compound; and c) comparing the presence, absence, amount, or activity of the at least one biomarker listed in Table 1 from steps a) and b), wherein an absence or a significantly decreased amount or activity of the at least one biomarker listed in Table 1 in the first subject sample relative to at least one subsequent subject sample, indicates that the agent treats the respiratory inflammatory disorder is provided.

In still another aspect, a method of assessing the efficacy of an agent for treating a respiratory inflammatory disorder, comprising: a) detecting in a subject sample at a first point in time the presence, absence, amount, or activity of at least one biomarker listed in Table 1; b) repeating step a) during at least one subsequent point in time after administration of the agent; and c) comparing the presence, absence, amount, or activity detected in steps a) and b), wherein an absence or a significantly decreased amount or activity of the at least one biomarker listed in Table 1 in the first subject sample relative to at least one subsequent subject sample, indicates that the agent treats the respiratory inflammatory disorder is provided. In one embodiment, the subject has undergone treatment, completed treatment, and/or is in remission for the respiratory inflammatory disorder between the first point in time and the subsequent point in time. In another embodiment, the first and/or at least one subsequent sample is selected from the group consisting of ex vivo and in vivo samples. In still another embodiment, the first and/or at least one subsequent sample is obtained from an animal model of the respiratory inflammatory disorder. In yet another embodiment, the first and/or at least one subsequent sample is a portion of a single sample or pooled samples obtained from the subject.

In some embodiments of the methods described herein, the at least one biomarker listed in Table 1 comprises a RGMb, NEO1, BMP2, and/or BMP4 biomarker, or a portion thereof. In another embodiment, the subject sample is selected from the group consisting of lung tissue, nasal tissue, sputum, whole blood, serum, plasma, urine, cells, cell lines, and biopsies. In still another embodiment, the presence or amount of the at least one biomarker listed in Table 1 is detected using a reagent which specifically binds with the protein. In yet another embodiment, the reagent is selected from the group consisting of an antibody, an antibody derivative, and an antibody fragment. In another embodiment, the presence or amount of the at least one biomarker listed in Table 1 is assessed by detecting the presence in the sample of a transcribed polynucleotide or portion thereof. In still another embodiment, the transcribed polynucleotide is an mRNA or a cDNA. In yet another embodiment, the step of detecting further comprises amplifying the transcribed polynucleotide. In another embodiment, the transcribed polynucleotide is detected by identifying a nucleic acid that anneals with the biomarker nucleic acid, or a portion thereof, under stringent hybridization conditions. In still another embodiment, the method further comprises determining whether the agent modulates one or more respiratory inflammatory disorder symptoms selected from the group consisting of AHR, recurrent wheezing, coughing, trouble breathing, chest tightness, symptoms that occur or worsen at night, symptoms that are triggered by cold air, exercise or exposure to allergens, upregulated serum IgE (atopy), eosinophilia, and excessive mucus secretion. In yet another embodiment, the respiratory inflammatory disorder is selected from the group consisting of allergic asthma, non-allergic asthma, respiratory allergy, chronic obstructive pulmonary disease (COPD), emphysema, chronic bronchitis, chronic sinusitis, rhinitis, lung infection, cystic fibrosis, interstitial fibrosis, nasal and sinus dysplasia, bronchopulmonary dysplasia and neoplasia, food allergies, Crohn's disease, and inflammatory bowel disease.

Figure 1:
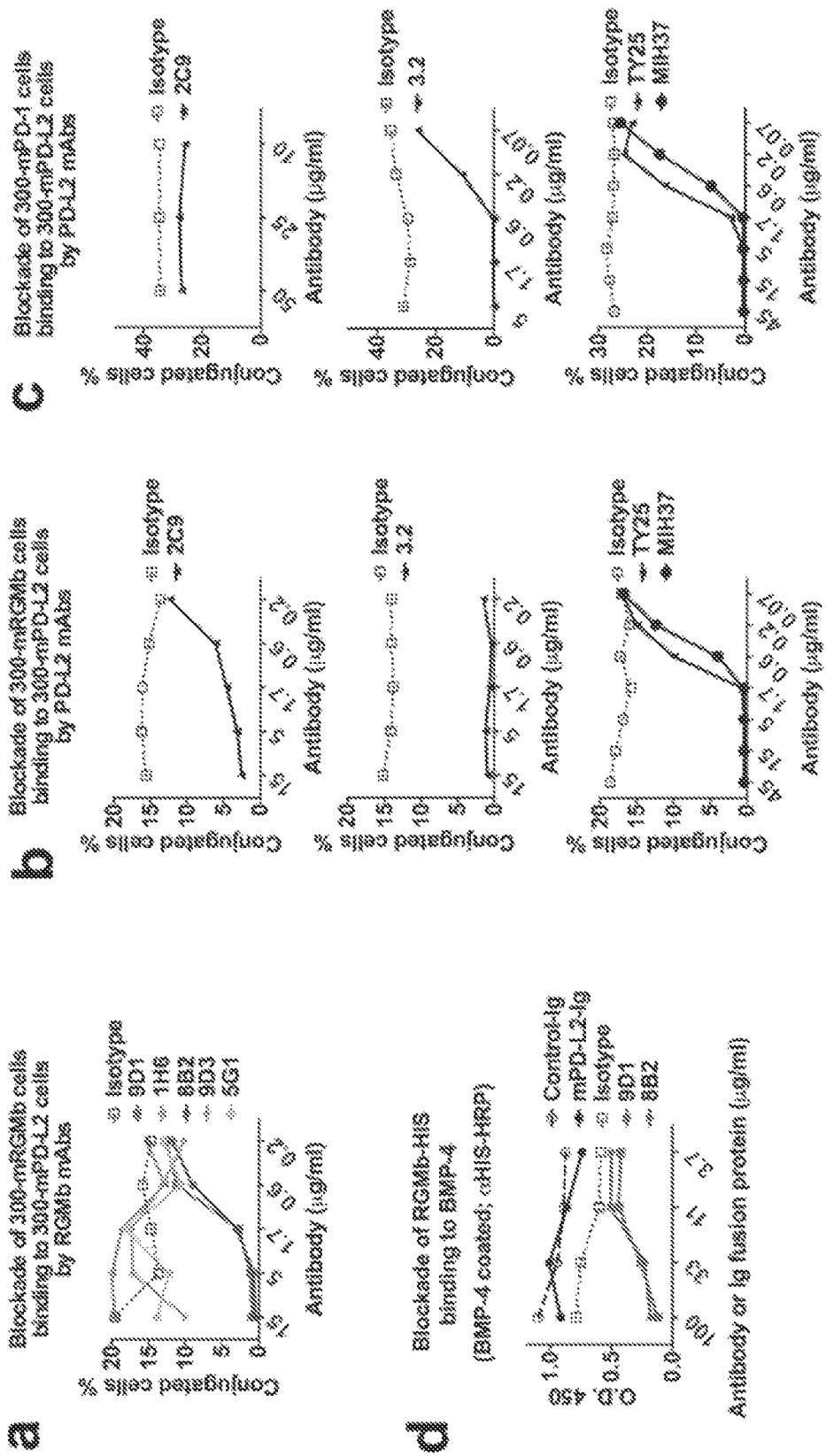
FIG. 1 includes nine panels, identified as panels (A), (B), (C), (D), (E), (F), (G), (H), and (I), which show the blocking capacities of RGMb and PD-L2 mAbs and a model for RGMb, PD-L2, Neogenein, BMP, and BMP-receptor interactions. Panels A-C show the capacities of RGMb mAbs and PD-L2 mAbs to block RGMb binding to PD-L2 or to block PD-1 to PD-L2, as determined by cell conjugation assay. Panel D shows the capacities of RGMb mAbs and mPD-L2-hIgG1/IgA to block RGMb binding to BMP-4 determined by ELISA. mRGMb-HIS was preincubated with mAbs or Ig fusion proteins and then added to BMP-4-coated plates. Binding of mRGMb-HIS was detected by anti-penta-HIS-HRP. Similar results were seen with BMP-2. Panel E shows the capacity of RGMb that has bound PD-L2 to also bind BMP-4 determined by ELISA. mPD-L2-hIgG or control-hIgG were preincubated alone or with monomeric mRGMb-HIS and then added to BMP-4-coated plates. Binding of Ig fusion proteins was detected with anti-hIgG-HRP. Similar results were also seen for BMP-2. Panel F shows the results of mNeogenin- or mPD-L2-transfected 300 cells stained with the indicated Ig fusion proteins or control-Ig and analyzed by flow cytometry. Panel G shows the capacities of RGMb mAbs to block RGMb-mIgG2a binding to neogenin-transfected 300 cells as determined by flow cytometry. Panel H shows the results of cell-to-cell binding of the indicated transfected cells analyzed by a cell conjugation assay. Panel 1I shows a molecular model depicting the PD-L2/BMP/BMPR/RGMb/neogenin pathway and the PD-L2/PD-1 pathway. Data shown in Panels 1A-1C and 1F-1H are representative of 2 or more independent experiments.
Figure 1:
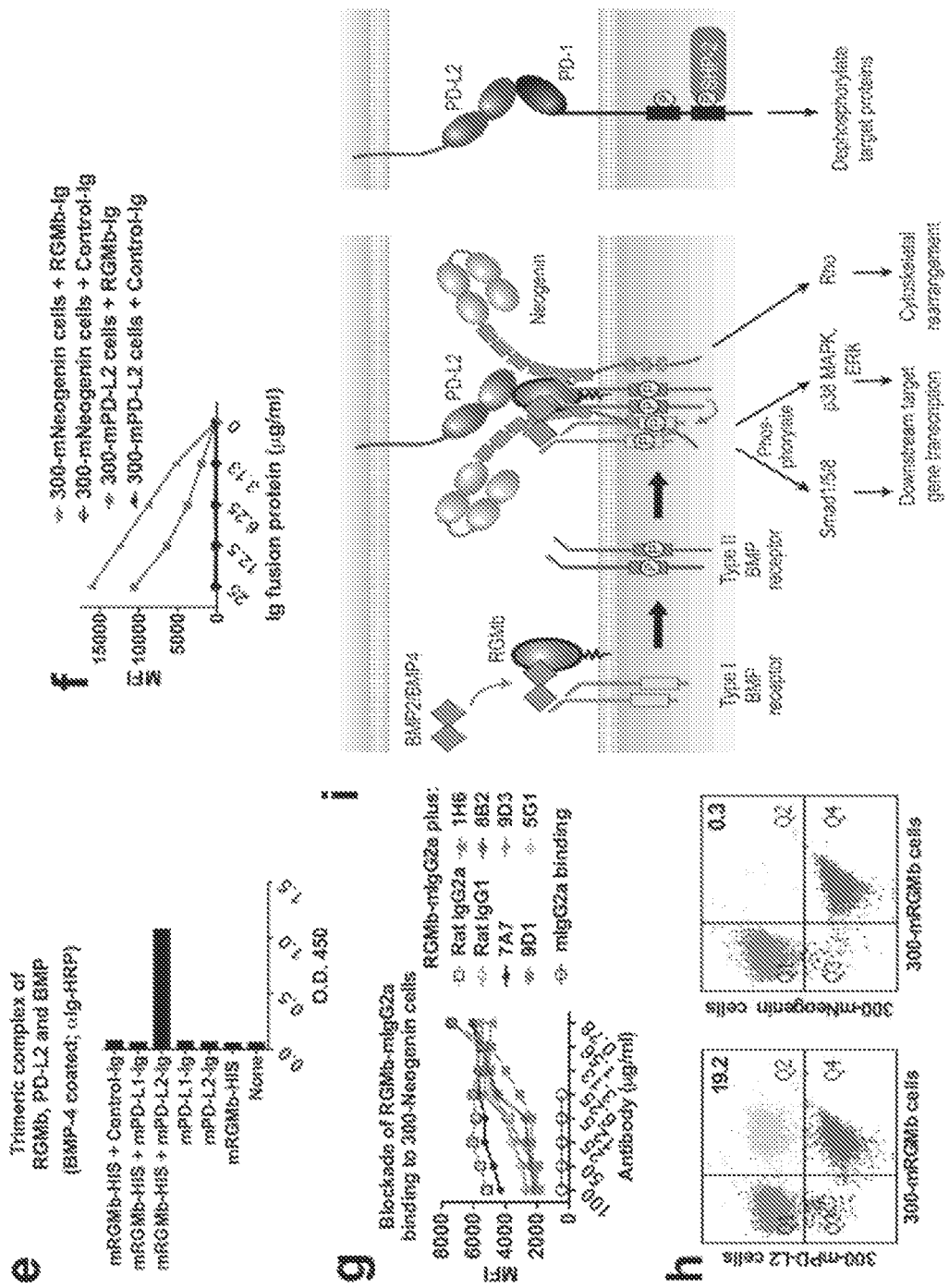

For figures and panels thereof showing bar graphs or line graphs, numerical labels are provided in the key and representative labels in the data corresponding to the labels in the keys are provided.

DETAILED DESCRIPTION OF THE INVENTION

It has been determined herein that RGMb functions at the effector stage, wherein NEO1 expressed in respiratory tissues like the lung binds RGMb and BMPs, resulting in release of cytokines which trigger inflammatory responses. Blocking RGMb-NEO1-BMP signaling, such as through the use of agents like anti-RGMb mAbs was determined to block the development of respiratory inflammatory disorder symptoms like airway hyperreactivity (AHR) and to inhibit the development of inflammation. Treatment with such agents was also effective when given at the time of antigen challenge, after sensitization, indicating that that RGMb-NEO1-BMP signaling functions at the effector stage.

I. Definitions

The articles "a" and "an" are used herein to refer to one or to more than one (i.e. to at least one) of the grammatical object of the article. By way of example, "an element" means one element or more than one element.

The term "activity," when used with respect to a polypeptide, e.g., a RGMb, NEO1, BMP2, and/or BMP4 polypeptide includes activities that are inherent in the structure of the protein. For example, with regard to RGMb, the term "activity" includes the ability to bind to its natural binding partners, including NEO1, BMP2, and/or BMP4 or to signal according to the model shown in FIG. 1i.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a cancer sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The "amount" of a marker, e.g., expression or copy number of a marker or MCR, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains: (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts. In addition, antibodies can be "humanized," which includes antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody," as used herein, also includes antibodies in which CDR sequences derived from the germline of another mammalian species, such as a mouse, have been grafted onto human framework sequences.

The term "antisense" nucleic acid polypeptide comprises a nucleotide sequence which is complementary to a "sense" nucleic acid encoding a protein, e.g., complementary to the coding strand of a double-stranded cDNA polypeptide, complementary to an mRNA sequence or complementary to the coding strand of a gene. Accordingly, an antisense nucleic acid polypeptide can hydrogen bond to a sense nucleic acid polypeptide.

The term "biological activity" or "functional activity" refers to an activity exerted by a polypeptide or portion thereof or nucleic acid molecule on a responsive cell or tissue, or on a binding partner, as determined in vivo, or in vitro, according to standard techniques.

In one embodiment, such an activity is a direct activity, such as an association of a polypeptide with its natural binding partner in vivo. As used herein, a "target molecule" or "binding partner" is a molecule with which a polypeptide binds or interacts in nature, such that a function of the polypeptide is achieved. In an exemplary embodiment, RGMb is a target molecule of BMPs like BMP2 and BMP4, as well as of NEO. Alternatively, an activity is an indirect activity, such as a cellular signaling activity mediated by an RGMb-NEO 1-BMP signaling complex.

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, vomit). In some embodiments, respiratory fluids, such as bronchial, alveolar, lung, sputum, mucous, or other fluids are useful.

The terms "CDR", and its plural "CDRs", refer to a complementarity determining region (CDR) of which three make up the binding character of a light chain variable region (CDR-L1, CDR-L2 and CDR-L3) and three make up the binding character of a heavy chain variable region (CDR-H1, CDR-H2 and CDR-H3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. In some embodiments, the CDRs described herein are determined according to listed segments of light chain and heavy chain variable region nucleic acid and polypeptide sequences (see, for example Table 3). See also Kabat, Chothia, and/or MacCallum et al., (Kabat et al., in "Sequences of Proteins of Immunological Interest," $5^{th}$ Edition, U.S. Department of Health and Human Services, 1992; Chothia et al. (1987) J. Mol. Biol. 196, 901; and MacCallum et al., J. Mol. Biol. (1996) 262, 732, each of which is incorporated by reference in its entirety).

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "composite antibody" refers to an antibody which has variable regions comprising germline or non-germline immunoglobulin sequences from two or more unrelated variable regions. Additionally, the term "composite, human antibody" refers to an antibody which has constant regions derived from human germline or non-germline immunoglobulin sequences and variable regions comprising human germline or non-germline sequences from two or more unrelated human variable regions. A composite, human antibody is useful as an effective component in a therapeutic agent according to the present invention since the antigenicity of the composite, human antibody in the human body is lowered.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

The term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The term "homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "hypervariable region," "HVR," or "HV." refers to the regions of an antibody-variable domain that are hypervariable in sequence and/or form structurally defined loops. Generally, antibodies comprise six HVRs; three in the VH (H1, H2, H3), and three in the VL (L1, L2. L3). In native antibodies, H3 and L3 display the most diversity of the six HVRs, and H3 in particular is believed to play a unique role in conferring fine specificity to antibodies. See, e.g., Xu et al. (2000) Immunity 13, 37-45; Johnson and Wu in Methods in Molecular Biology 248, 1-25 (Lo, ed., Human Press, Totowa, N.J., 2003)). Indeed, naturally occurring camelid antibodies consisting of a heavy chain only are functional and stable in the absence of light chain (see, e.g., Hamers-Casterman et al. (1993) Nature 363:446-448 (1993) and Sheriff et al. (1996) Nature Struct. Biol. 3, 733-736). The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

The term "interaction," when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting costimulation). To inhibit such an interaction results in the disruption of the activity of one or more molecules involved in the interaction. To enhance such an interaction is to prolong or increase the likelihood of said physical contact, and prolong or increase the likelihood of said activity.

The term "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of polypeptide, in which the protein is separated from cellular components of the cells from which it is isolated or recombinantly produced. In one embodiment, the language "substantially free of cellular material" includes preparations of protein, having less than about 30% (by dry weight) of non-desired protein (also referred to herein as a "contaminating protein"), more preferably less than about 20% of non-desired protein, still more preferably less than about 10% of non-desired protein, and most preferably less than about 5% non-desired protein. When antibody, polypeptide, peptide or fusion protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The term "isotype" refers to the antibody class (e.g., IgM or IgG1) that is encoded by heavy chain constant region genes.

The term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

The term "modulate" includes up-regulation and down-regulation, e.g., enhancing or inhibiting a response.

The term "naturally-occurring" nucleic acid polypeptide refers to an RNA or DNA polypeptide having a nucleotide sequence that occurs in nature (e.g., encodes a natural protein).

The "normal" level of expression of a marker is the level of expression of the marker in cells of a subject, e.g., a human patient, not afflicted with a cancer. An "overexpression" or "significantly higher level of expression" of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

The term "PD-1" refers to a member of the immunoglobulin gene superfamily that functions as a coinhibitory receptor having PD-L1 and PD-L2 as known ligands. PD-1 was previously identified using a subtraction cloning based approach to select for proteins involved in apoptotic cell death. PD-1 is a member of the CD28/CTLA-4 family of molecules based on its ability to bind to PD-L1. Like CTLA4. PD-1 is rapidly induced on the surface off-cells in response to anti-CD3 (Agata et al. 25 (1996) Int. Immunol. 8:765). In contrast to CTLA4, however, PD-1 is also induced on the surface of B-cells (in response to anti-IgM). PD-1 is also expressed on a subset of thymocytes and myeloid cells (Agata et al. (1996) supra; Nishimura et al. (1996) Int. Immunol. 8:773).

The nucleic acid and amino acid sequences of a representative human PD-1 biomarker is available to the public at the GenBank database under NM_005018.2 and NP_005009.2 and is shown in Table 1 (see also Ishida et al. (1992) 20 EMBO J 11:3887; Shinohara et al. (1994) Genomics 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) EMBO J. 11:3887; Shinohara et al. (1994) Genomics 23:704: U.S. Pat. No. 5,698,520). These features also define a larger family of polypeptides, called the immunoinhibitory receptors, which also includes gp49B, PIR-B, and the killer inhibitory receptors (KIRs) (Vivier and Dacron (1997) Immunol. Today 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA4 bind to B7-1 and B7-2. It has been proposed that there is a phylogenetic relationship between the MHC and B7 genes (Henry et al. (1999) Immunol. Today 20(6):285-8). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell. e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) J. Exp. Med. 192:1027) and PD-L2 (Latchman et al. (2001) Nat. Immunol. 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) J. Exp. Med. 192:1027 for sequence data) and PD-L2 (See Latchman et al. (2001) Nat. Immunol. 2:261 for sequence data) are members of the B7 family of polypeptides. Both PD-L and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells.

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two P sheets, each consisting of anti-parallel P strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and form an additional pair of β strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28. ICOS, PD-1 and/or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

The term "PD-L2" refers to a specific PD-1 ligand. PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The nucleic acid and amino acid sequences of representative human PD-L2 biomarkers (e.g., SEQ ID NOs: 23 and 24) are well known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 of SEQ ID NO: 8 comprises a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) Annu. Rev. Neurosci. 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two 1 sheets, each consisting of antiparallel (3 strands of 5-10 amino acids with a conserved disulfide bond between the two sheets in most, but not all, domains. IgC domains of g, TCR, and MHC molecules share the same types of sequence patterns and are called the Cl set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody. e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "respiratory inflammatory disorder" refers to a number of well-known conditions affecting the respiratory system, including the lungs, airways, and nasal cavity, and mediated by inflammatory mechanisms. Such conditions include, without limitation, asthma, respiratory allergy, chronic obstructive pulmonary disease (COPD), emphysema, chronic bronchitis, chronic sinusitis, rhinitis, lung infection, cystic fibrosis, interstitial fibrosis, nasal and sinus dysplasia, bronchopulmonary dysplasia and neoplasia, lung inflammation, pneumonia, hypersensitivity pneumonitis, pulmonary infiltrated with eosinophilia, environmental lung disease, bronchiectasis, interstitial lung disease, acute respiratory distress syndrome, mesothelioma, asbestosis, aspergilloma, aspergillosis, bronchiectasis, idiopathic pulmonary fibrosis, invasive pneumococcal disease, influenza, nontuberculous mycobacteria, pneumoconiosis, pneumocytosis, pneumonia, pulmonary actinomycosis, rheumatoid lung disease, sarcoidosis, and Wegener's granulomatosis.

Since respiratory inflammation involves mucosal immunology, other sites of mucosal immune responses, such as those involving the intestines are also contemplated within the scope of respiratory inflammatory disorders. Such disorders include gastrointestinal allergies, including food allergies such as peanuts, milk polypeptides, egg proteins, strawberries and the like, eosinophilia, conjunctivitis, glomerulonephritis, Crohn's disease, inflammatory bowel disease, as well as certain pathogen infections like human immunodeficiency virus (HIV), tuberculosis, and lepromatous leprosy.

Asthma is a chronic inflammatory disease of the airways that is characterized by recurrent episodes of reversible airway obstruction and airway hyperreactivity (AHR). Typical clinical manifestations include shortness of breath, wheezing, coughing and chest tightness that can become life threatening or fatal. While existing therapies focus on reducing the symptomatic bronchospasm and pulmonary inflammation, there is a growing awareness of the role of long-term airway remodeling in accelerated lung deterioration in asthmatics. Airway remodeling refers to a number of pathological features including epithelial smooth muscle and myofibroblast hyperplasia and/or metaplasia, subepithelial fibrosis and matrix deposition. The processes collectively result in up to about 300% thickening of the airway in cases of fatal asthma.

Extrinsic, or allergic asthma, is more common (90% of all cases) than intrinsic (non-allergic) and typically develops in childhood (approximately 80% of children with asthma also have documented allergies, and other allergic conditions, such as nasal allergies or eczema, are often also present. An "allergy" is an inflammatory disorder caused by acquired hypersensitivity to a substance (i.e., allergen). Non-allergic asthma is not mediated by an allergen and does not involve $TH_2$ cytokines such as interleukin (IL)-4, IL-5 and IL-13. By contrast, allergic asthma is initiated by an inappropriate inflammatory reaction to airborne allergens. The lungs of asthmatics demonstrate an intense infiltration of lymphocytes, mast cells and eosinophils that is driven by CD4+ T-cells expressing a $TH_2$ cytokine profile. This can be experimentally initiated using sensitization of an animal to ovalbumin (OVA) followed by intratracheal delivery of the OVA challenge. This procedure generates a $TH_2$ immune reaction in the mouse lung and mimics four major pathophysiological responses seen in human asthma, including upregulated serum IgE (atopy), eosinophilia, excessive mucus secretion, and AHR.

Chronic obstructive pulmonary disease (COPD) is an umbrella term used to describe airflow obstruction that is associated mainly with emphysema and chronic bronchitis. Emphysema causes irreversible lung damage by weakening and breaking the air sacs within the lungs. Inflammatory cells in emphysematous lung release elastase enzymes, which degrade or damage elastin fibers within the lung matrix. As a result, elasticity of the lung tissue is lost, causing airways to collapse and obstruction of airflow to occur. Chronic bronchitis is an inflammatory disease that begins in the smaller airways within the lungs and gradually advances to larger airways. It increases mucus in the airways and bacterial infections in the bronchial tubes, which, in turn, impedes airflow.

Chronic sinusitis is an inflammation of the membrane lining of one or more paranasal sinuses. Chronic sinusitis lasts longer than three weeks and often continues for months. In cases of chronic sinusitis, there is usually tissue damage.

Respiratory allergy is an unwanted inflammatory response to an antigen by respiratory cells or tissues.

Lung infections, including viral, bacterial, or fungal infection, can also lead to inflammation and/or scarring of the lungs, the pleural cavity that surrounds the lungs, the alveoli, and/or the bronchial passages. In particular, pneumonia, influenza, SARS, tuberculosis, and whooping cough (pertussis) can all lead to chronic lung problems due to inflammation and scarring in the lungs.

Rhinitis is a condition comprising irritation and inflammation of internal areas of the nose. The primary symptom of rhinitis is a runny nose, caused by chronic or acute inflammation of the nasal mucous membranes due to viruses, bacteria or irritants. This inflammation results in generation of excessive amounts of mucus, producing a runny nose, nasal congestion and post-nasal drip. More than fifty million Americans are current sufferers. In addition to affecting the nose, throat, and eyes, rhinitis has been associated with sleeping problems, problems with the ears, and even been linked to learning problems. Rhinitis is caused by an increase in histamine, typically caused by airborne allergens that affect an individual's nose, throat, or eyes and cause an increase in fluid production within these areas. Allergic rhinitis (hay fever) is caused by pollens of specific seasonal plants, airborne chemicals and dust particles in people who are allergic to these substances. Symptoms of allergic rhinitis include sneezing, runny nose and itching eyes, infection, inflammation, mucus production and/or secretion, burning, and itching.

Therapies for respiratory inflammatory disorders include the use of bronchodilators (e.g., anticholinergics such as ipratropium and beta-agonists such as albuterol), corticosteroids, oxygen, cytokine and immunomodulatory inhibitors (e.g., TNFa and IL-13 inhibitors), leukotriene inhibitors, and the like. Such agents can be administered in the form of an inhaler or atomizer. Exemplary agents include inhaled corticosteroids, glucocorticoids (e.g., ciclesonide, beclomethasone, budesonide, flunisolide, fluticasone, mometasone, triamcinolone, etc.), oral leukotriene modifiers (e.g., montelukast, zafirlukast, pranlukast, zileuton, etc.), mast-cell stabilizers (cromoglicate, nedocromil, etc.), β-2 agonists (e.g., salbutamol, levalbuterol, terbutaline, bitolterol, fluticasone, salmeterol, budesonide, formoterol, etc.), epinephrine, ephedrine, and methylxanthines (e.g., theophylline, aminophylline, etc.). In severe asthmatics, oral glucocorticoids may be added to these treatments during severe attacks. Additionally, anticholinergic drugs (i.e. ipratropium bromide, oxitropium, tiotropium, etc.) may be administered. Antihistamines or IgE blockers (such as Omalizumab) may also benefit asthmatics suffering from allergic asthma. The treatments share the same therapeutic goal of bronchodilation, reducing inflammation, and facilitating expectoration. Many of such treatments, however, include undesired side effects and lose effectiveness after being used for a period of time. Additionally, only limited agents for therapeutic intervention are available for decreasing the airway remodeling process that occurs in asthmatics.

The term "RGMb-NEO1-BMP signaling pathway" refers to one of the intracellular signaling pathways activated by the binding of BMP factors to RGMb and NEO1 co-receptors. Without being bound by theory, it is believed that the RGMb-NEO1-BMP signaling pathway signals according to the model shown in FIG. 1i, wherein RGMb forms a signaling supercomplex of BMP-BMP receptors-RGMb-Neogenin (BBRN supercomplex). RGMb directly binds to BMP-2 or BMP-4, which bind to type I BMP receptors (BMPR1a, BMPR1b, ACVR1, ACVRL1) and recruit type II BMP receptors (BMPR2, ACVR2a. ACVR2b) (Corradini et al. (2009) Cytokine Growth Factor Rev. 20:389-398 and Yoshioka et al. (2012) Eur. J. Immunol. 42:749-759). Then type II BMP receptors phosphorylate type I BMP receptors, which phosphorylate Smad1/5/8 or p38 mitogen activated protein kinase (MAPK) and extracellular signal-regulated protein kinase (ERK), leading to downstream target gene transcription (Corradini et al. (2009) Cytokine Growth Factor Rev. 20:389-398 and Xia et al. (2010) J. Immunol. 186:1369-1376). RGMs facilitate the utilization of ACVR2a by BMP-2/4. In the absence of an RGM, BMP-2/4 preferentially utilize BMPR2 (Corradini et al. (2009) Cytokine Growth Factor Rev. 20:389-398). RGMb may also signal through neogenin and downstream effector Rho, triggering cytoskeletal rearrangement (Bell et al. (2013) Science 341: 77-80 and Conrad et al. (2007) J. Biol. Chem. 282:16423-16433). PD-L2 may interact with this BBRN supercomplex by binding to RGMb, and modulate these signaling pathways. For example, the right panel of FIG. 1i shows PD-L2 binding to PD-1 which results in tyrosine phosphorylation of the PD-1 cytoplasmic domain, recruitment of tyrosine phosphatases, particularly SHP-2, and attenuation of antigen receptor signals. Thus, PD-L2 may participate in three important signaling circuits, the PD-1, BMP, and neogenin signaling pathways, by binding to either PD-1 or RGMb. As demonstrated below, however, the RGMb-NEO1-BMP signaling pathway relevant to respiratory disorders can be mediated independently of the PD-L2 and PD-1 signaling pathways.

In some embodiments, the RGMb-NEO1-BMP signaling pathway is limited to subsets of biomolecules within the pathway, such as RGMb, NEO1, BMP2, and BMP4, or even individual biomolecules within the pathway, such as RGMb.

Exemplary agents useful for inhibiting the RGMb-NEO1-BMP signaling pathway, or other biomarkers described herein, include antibodies, small molecules, peptides, peptidomimetics, natural ligands, and derivatives of natural ligands, that can either bind and/or inactivate or inhibit target proteins, or fragments thereof; as well as RNA interference, antisense, nucleic acid aptamers, etc. that can downregulate the expression and/or activity of target nucleic acids, or fragments thereof. In some embodiments, a single agent or a combination of agents can be used to disrupt signaling by the BBRN supercomplex. Exemplary inhibitors of the RGMb-NEO1-BMP signaling pathway are also well known in the art and include, but are not limited to BMP inhibitors, such as inhibitors of BMP2 and BMP4 include noggin, chrodin, Cer1, DAN, WISE (USAG-1), SOST (Extodin), and Gremlin, as well as antibodies, nucleic acids, and extracellular domains of BMP receptors such as soluble activin extracellular domains. Similarly, antibodies that bind to RGMb and/or neogenin to block the interaction with its natural binding partners are contemplated, as well as the use of such natural binding partners, or soluble fragments thereof.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample. In one embodiments, respiratory samples as described herein are preferred.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. 1998. Science 282:63), and natural product extract libraries. In another embodiment, the compounds are small, organic non-peptidic compounds. In a further embodiment, a small molecule is not biosynthetic.

The term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using human Gall as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

The term "subject" refers to any healthy animal, mammal or human, or any animal, mammal or human afflicted with a condition of interest (e.g., cancer). The term "subject" is interchangeable with "patient."

The term "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

A "transcribed polynucleotide" or "nucleotide transcript" is a polynucleotide (e.g. an mRNA, hnRNA, cDNA, mature miRNA, pre-miRNA, pri-miRNA, miRNA*, anti-miRNA, or a miRNA binding site, or a variant thereof or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

The term "T cell" includes $CD4^+$ T cells and $CD8^+$ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, oligodendrocytes).

The term "treating" or "treatment" or "alleviation" refers to measures, wherein the object is to prevent or slow down (lessen) the targeted pathologic condition or disorder or relieve some of the symptoms of the disorder. Those in need of treatment include can include those already with the disorder as well as those prone to have the disorder or those in whom the disorder is to be prevented. A subject or mammal is successfully "treated" for asthma if, after receiving a therapeutic agent of the present invention, the patient shows observable and/or measurable reduction in or absence of one or more of the following: recurrent wheezing, coughing, trouble breathing, chest tightness, symptoms that occur or worsen at night, symptoms that are triggered by cold air, exercise or exposure to allergens, upregulated serum IgE (atopy), eosinophilia, excessive mucus secretion, AHR. Such parameters can be measured using well known techniques. For example, "Forced expiratory volume (FEV)" is a standard test that measures the volume of air expelled in the first second of a forced expiration. FEV is measured by a spirometer, which consists of a mouthpiece and disposable tubing connected to a machine that records the results and displays them on a graph. To perform spirometry, a person inhales deeply, closes the mouth tightly around the tube and then exhales through the tubing while measurements are taken. The volume of air exhaled, and the length of time each breath takes is recorded and analyzed. Spirometry results are expressed as a percentage. Examples of normal spirometry results include a FEV of 75 percent of vital capacity after one second. An example of abnormal spirometry results include a reading of less than 80 percent of the normal predicted value. An abnormal result usually indicates the presence of some degree of obstructive lung disease such as asthma, emphysema or chronic bronchitis, or restrictive lung disease such as pulmonary fibrosis. For example, FEV values (percentage of predicted) can be used to classify the obstruction that may occur with asthma and other obstructive lung diseases like emphysema or chronic bronchitis: an FEV of 65%-79% indicates mild obstruction, an FEV of 40%-59% indicates moderate obstruction, and an FEV of <40% indicates severe obstruction.

An "underexpression" or "significantly lower level of expression or copy number" of a marker (e.g., RGMb, NEO1, BMPs, or downstream signaling marker thereof) refers to an expression level or copy number in a test sample that is greater than the standard error of the assay employed to assess expression or copy number, but is preferably at least twice, and more preferably three, four, five or ten or more times less than the expression level or copy number of the marker in a control sample (e.g., sample from a healthy subject not afflicted with cancer) and preferably, the average expression level or copy number of the marker in several control samples.

The term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "tolerance" or "unresponsiveness" includes refractivity of cells, such as immune cells, to stimulation, e.g., stimulation via an activating receptor or a cytokine. Unresponsiveness can occur, e.g., because of exposure to immunosuppressants or exposure to high doses of antigen. Several independent methods can induce tolerance. One mechanism is referred to as "anergy," which is defined as a state where cells persist in vivo as unresponsive cells rather than differentiating into cells having effector functions. Such refractivity is generally antigen-specific and persists after exposure to the tolerizing antigen has ceased. For example, anergy in T cells is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the API sequence that can be found within the enhancer (Kang et al. (1992) *Science* 257:1134). Another mechanism is referred to as "exhaustion." T cell exhaustion is a state of T cell dysfunction that arises during many chronic infections and cancer. It is defined by poor effector function, sustained expression of inhibitory receptors and a transcriptional state distinct from that of functional effector or memory T cells.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for a fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

Finally, nucleic acid and amino acid sequence information for nucleic acid and polypeptide molecules useful in the present invention are well known in the art and readily available on publicly available databases, such as the National Center for Biotechnology Information (NCBI). For example, exemplary nucleic acid and amino acid sequences derived from publicly available sequence databases are provided in Table 1 below.

For example, the term "RGMb" or "DRAGON" refers to a member of the repulsive guidance molecule family, which consists of RGMa, RGMb and RGMc/hemojuvelin (Severyn et al. (2009) *Biochem J.* 422:393-403). RGMs are glycosylphosphatidylinositol (gpi)-anchored membrane proteins that bind bone morphogenic proteins (BMPs) and neogenin (Conrad et al. (2010) *Mol. Cell Neurosci.* 43:222-231). RGMb directly binds to BMP-2 or BMP-4, which in turn bind to type I receptors (ALK1, ALK2, ALK3, and ALK6) and type II receptors (BMPRII, ActRIIa and ActRIIb) (Corradini et al. (2009) *Cytokine Growth Factor Rev.* 20:389-398 and Yoshioka et al. (2012) *Eur. J. Immunol.* 42:749-759). RGMs coordinate utilization of specific BMP receptors (Corradini et al. (2009) *Cytokine Growth Factor Rev.* 20:389-398). RGMs do not directly signal but can act as co-receptors (e.g., RGMb binds directly to BMP-2/4) that modulate BMP signaling (Samad et al. (2005) *J. Biol. Chem.* 280:14122-14129). RGMb is expressed and functions in the nervous system (Severyn et al. (2009) *Biochem J.* 422:393-403) and RGMb deficient mice have an early lethal phenotype. In addition, RGMb expression is observed in macrophages and other cells of the immune system (Xia et al. (2010) *J. Immunol.* 186:1369-1376). A role for RGMb in the immune system is only beginning to emerge (Galligan et al. (2007) *J. Immunol.* 143:2714-2722 and Xia et al. (2010) *J. Immunol.* 186:1369-1376). For example, the relationship of RGMb-BMP-neogenin signaling in mediating respiratory disorders or that modulating such signaling could effectively treat such respiratory disorders, especially at the effector stage, were not heretofore known.

The nucleic acid and amino acid sequences of representative human RGMb (e.g., SEQ ID NOs: 1 and 2) biomarkers are well known in the art and are also available to the public at the GenBank database under NM_001012761.2 and NP_001012779.2. RGMb proteins are characterized by common structural elements. In some embodiments, RGMb proteins comprise conserved domains with homology to notch-3, phosphatidylinositol-4-phosphate-5-kinase type II beta, insulin-like growth factor binding protein-2, thrombospondin, ephrin type-B receptor 3 precursor, and Slit-2, all of which are known to influence axonal guidance, neurite outgrowth, and other neuronal developmental functions. The C-terminus of RGMb also contains a hydrophobic domain indicative of a 21 amino acid extracellular GPI anchoring. In addition, nucleic acid and polypeptide sequences of RGMb orthologs in organisms other than humans are well known and include, for example, mouse RGMb (NM_178615.3 and NP_848730.2), chimpanzee RGMb (XM_517848.4 and XP_517848.2), monkey RGMb (NM_001265620.1 and NP_001252549.1), cow RGMb (XM_002689413.2 and XP_002689459.2), chicken RGMb (XM_424860.4 and XP_424860.4), and zebrafish RGMb (NM_001001727.1 and NP_001001727.1).

The term "neogenin" refers to a gene encoding the NEO1 protein. At least three splice variants of human neogenin are known. The nucleic acid sequence of transcript variant 1 is available as NM_002499.3, which encodes isoform 1 that is available as NP_002490.2. Transcript variant 2 (NM_001172623.1) lacks an in-frame exon in the coding region relative to transcript variant 1, which encodes an isoform that is shorter than isoform 1 (NP_001166094.1). Transcript variant 3 (NM_001172624.1) also lacks an in-frame exon in the coding region relative to transcript variant 1, which encodes an isoform that is shorter than isoform 1 (NP_001166095.1). Neogenin proteins are characterized by common structural elements. In some embodiments, neogenin proteins comprise four N-terminal immunoglobulin-like domains, six fibronectin type III domains, a transmembrane domain and a C-terminal internal domain that shares homology with the tumor suppressor candidate gene, deleted in colorectal cancer (DCC). In addition, nucleic acid and polypeptide sequences of neogenin orthologs in organisms other than humans are well known and include, for example, mouse neogenin (NM_008684.2, NP_032710.2, NM_001042752.1, and NP_001036217.1), chimpanzee neogenin (XM_510660.3, XP_510660.3, XM_003314752.1, XP_003314800.1, XM_003314751.1, and XP_003314799.1), monkey neogenin (NM_00121500.1 and NP_001248429.1), dog neogenin (XM_005638577.1, XP_005638634.1, XM_005638581.1, XP_005638638.1, XM_005638578.1, XP 005638635.1, XM_005638579.1, XP 005638636.1, XM_005638580.1, XP_005638637.1, XM_544760.4, XP_544760.2, XM_003433937.2, XP_003433985.1, XM_003433936.2, and XP_003433984.1), cow neogenin (XM_005211431.1, XP 005211488.1, XM_005211432.1, XP_005211489.1, XM_002690492.3, XP_002690538.1, XM_003586508.2, XP_003586556.1, XM_005211433.1, XP_005211490.1, XM_003586507.2, and XP_003586555.1), rat neogenin (XM_006243186.1 and XP_006243248.1), chicken neogenin (XM_004943656.1, XP_004943713.1, XM_004943654.1, XP_004943711.1, XM_004943655.1, XP_004943712.1, XM_413704.4, XP_413704.4, XM_004943657.1, and XP_004943714.1), and zebrafish neogenin (NM_173218.1 and NP_775325.1).

The term "BMP" refers to a family with more than 20 members related to the transforming growth factor-β (TGF-β) family (Bragdon et al. (2011) *Cell Signal.* 23:609-620 and Yoshioka et al. (2012) *Eur. J. Immunol.* 42:749-759). Signaling is initiated when a BMP ligand binds to complexes of two type I and two type II serine/threonine kinase receptors. Constitutively active type II receptors phosphorylate type I receptors, which phosphorylate Smad proteins. The BMP subfamily signals via one set of receptor-activated Smads (Smad1, Smad5 and Smad8), whereas the TGF-β subfamily signals via another set (Smad2 and Smad3). Phosphorylated receptor-activated Smads form heteromeric complexes with common mediator Smad4, and the Smad complexes translocate to the nucleus where they modulate gene transcription. Regulation of this pathway occurs at multiple levels in order to generate specificity and to finely tune these signals. One key regulatory mechanism is the promotion or inhibition of ligand binding by coreceptors. RGM family members RGMa and RGMb (DRAGON) are the first described co-receptors for the BMP subfamily. Both RGMa and RGMb bind selectively to BMP-2 and BMP-4 ligands, interact with BMP receptors and enhance cellular responses to BMP ligands (Samad et al. (2005)*J. Biol. Chem.* 280:14122-14129; Babitt et al. (2005)*J. Biol. Chem.* 280:29820-29827 (2005); and Shi et al. (2003) *Cell* 113:685-700).

The nucleic acid and amino acid sequences of representative human BMP2 (e.g., SEQ ID NOs: 13 and 14) biomarkers are well known in the art and are also available to the public at the GenBank database under NM_001012761.2 and NP_001012779.2 (preproprotein at residues 1-396, signal peptide at residues 1-23, proprotein at residues 24-396, and the mature peptide at residues 283-396). In addition, nucleic acid and polypeptide sequences of BMP2 orthologs in organisms other than humans are well known and include, for example, mouse BMP2 (NM_007553.3 and NP_031579.2 with preproprotein at residues 1-394, signal peptide at residues 1-23, proprotein at residues 24-394, and the mature peptide at residues 281-394), chimpanzee BMP2 (XM_514508.2 and XP_514508.2), monkey BMP2 (XM_001115987.1 and XP_001115987.1), dog BMP2 (XM_534351.4 and XP_534351.2), cow BMP2 (NM_001099141.1 and NP_001092611.1), rat BMP2 (NM_017178.1 and NP_058874.1), chicken BMP2 (NM_204358.1 and NP_989689.1), and zebrafish BMP2 (NM_131360.1 and NP_571435.1).

At least three splice variants of human BMP4 are known. The nucleic acid sequence of transcript variant 1 is available as NM_001202.4. Transcript variant 2 (NM_130850.2) and variant 3 (NM_130851.2) each differ from transcript variant 1 only in the 5' untranslated region (5' UTR) such that all three variants encode the same protein (NP_001193.2, NP_570911.2, and NP_570912.2) (preproprotein at residues 1-408, signal peptide at residues 1-24, proprotein at residues 36-275, and, in some embodiments, the mature peptide at residues 308-408). In addition, nucleic acid and polypeptide sequences of BMP4 orthologs in organisms other than humans are well known and include, for example, mouse BMP4 (NM_007554.2 and NP_031580.2 with preproprotein at residues 1-408, signal peptide at residues 1-19, proprotein at residues 36-276, and, in some embodiments, the mature peptide at residues 308-408), chimpanzee BMP4 (XM_509954.3, XP_509954.3, XM_003314329.1, XP_003314377.1, XM_003314330.1, and XP_003314378.1), monkey BMP4 (XM_001084801.2, XP_001084801.1, XM_001084680.2, XP_001084680.1, XM_002805069.1, XP_002805115.1, XM_001084317.1, and XP_001084317.1), dog BMP4 (NM_001287170.1 and NP_001274099.1), cow BMP4 (NM_001045877.1 and NP_001039342.1), rat BMP4 (NM_012827.2 and NP_036959.2), and zebrafish BMP4 (NM_131342.2 and NP_571417.1).

TABLE 1

```
SEQ ID NO: 1 Human RGMB cDNA Sequence
    1 atgataagga agaagaggaa gcgaaacgcg ccccccggcc catgccgcag ccacgggccc
   61 agacccacca cgacgcccgc gccgccgccc tcgccggaac ccacaagacc tgcatggacg
  121 ggcatgagct tgagagcagc accttccagc gccgccgctg ccgccgccga agttgagcag
  181 cgccgcagcc ccaggctcta ccccccgccg ctggagctac tgctactgct actgttcagc
  241 ctcgggctgc tccacgcagg tgactgccaa cagccagccc aatgtcgaat ccagaaatgc
  301 accacggact tcgtgtccct gacttctcac ctgaactctg ccgttgacgg ctttgactct
  361 gagttttgca aggccttgcg tgcctatgct ggctgcaccc agcgaacttc aaaagcctgc
  421 cgtggcaacc tggtatacca ttctgccgtg ttgggtatca gtgacctcat gagccagagg
  481 aattgttcca aggatggacc cacatcctct accaacccg aagtgaccca tgatccttgc
  541 aactatcaca gccacgctgg agccagggaa cacaggagag gggaccagaa ccctcccagt
  601 taccttttt gtggcttgtt tggagatcct cacctcagaa cttcaagga taacttccaa
  661 acatgcaaag tagaaggggc ctggccactc atagataata attatctttc agttcaagtg
  721 acaaacgtac ctgtggtccc tggatccagt gctactgcta caaataagat cactattatc
  781 ttcaaagccc accatgagtg tacagatcag aaagtctacc aagctgtgac agatgacctg
  841 ccggccgcct ttgtggatgg caccaccagt ggtggggaca gcgatgccaa gagcctgcgt
  901 atcgtggaaa gggagagtgg ccactatgtg gagatgcacg cccgctatat agggaccaca
  961 gtgtttgtgc ggcaggtggg tcgctacctg accttgcca tccgtatgcc tgaagacctg
 1021 gccatgtcct acgaggagag ccaggacctg cagctgtgcg tgaacggctg ccccctgagt
 1081 gaacgcatca tgacaggca gagccaggtg tctgccatcc tgggacacag cctacctcgc
 1141 acctccttga tgcagacctg gcctggctac acactggaga ctgccaacac tcaatgccat
 1201 gaaaagatgc cagtgaagga catctatttc cagtcctgtg tcttcgacct gctcaccact
 1261 ggtgatgcca actttactgc cacagcccac agtgccttgg aggatgtaga ggccctgcac
 1321 ccaaggaaga aacgctggca cattttcccc agcaatggca atgggactcc ccgtggaggc
 1381 agtgatttgt ctgtcagtct aggactcacc tgcttgatcc ttatcgtgtt tttgtag SEQ ID NO: 2 Human RGMb Amino Acid Sequence
    1 mirkkrkrsa ppgpcrshgp rpatapappp speptrpawt gmglraapss aaaadaeveq
   61 rrspglcppp lelllllfs lgllhagdcq qpaqcriqkc ttdfvsltsh lnsavdgfds
  121 efckalraya gctqrtskac rgnlvyhsav lgisdlmsgr ncskdgptss tnpevthdpc
  181 nyhshagare hrrgdqnpps ylfcglfgdp hlrtfkdnfq tckvegawpl idnnylsvqv
  241 tnvpvvpgss atatnkitii fkahhectdq kvyqavtddl paafvdgtts ggdsdakslr
  301 iveresghyv emharyigtt vfvrqvgryl tlairmpedl amsyeesqdl qlcvngcpls
  361 eriddgqgqv sailghslpr tslvqawpgy tletantqch ekmpvkdiyf qscvfdlltt
  421 gdanftaaah saledvealh prkerwhifp ssgngtprgg sdlsyslglt clilivfl SEQ ID NO: 3 Mouse RGMb cDNA Sequence
    1 atgggcgtga gagcagcacc ttcctgcgcc gccgcccccg ccgccgccgg ggctgagcag
   61 tcccgccgcc ccgggctctg gccgccgtcg ccccccgccg cgctgttgct gctgctgctg
  121 ctcagccttg ggctgctcca cgcaggtgat tgccaacagc ctactcaatg ccgaatccag
  181 aaatgtacca cagacttcgt ggccctgact gcacacctga actctgccgc tgatgggttt
  241 gactctgagt tttgcaadgc acttcgcgcc tatgctggct gcacccagcg aacttcaaag
  301 gcctgccgag gcaacctggt gtaccattct gctgtgttag catcagtga tctcatgagc
  361 cagaggaact gttccaagga tggacccaca tcttccacca atccggaagt gacccatgac
  421 ccctgtaact accacagcca cggggagtc agagaacatg gggagggga ccagagacct
  481 cccaattacc ttttctgtgg cttgtttgga gaccctcacc ttcgaacttt caaggatcac
  541 ttccagacat gcaaagtgga aggggcctgg ccactcatag caacaatta cctttcggtt
  601 caagtgacga acgtgcctgt ggtccccggg tccagtgcaa ctgctacaaa caaggtcacg
  661 attatcttca agcacgca cgagtgcacg gatcagaagg tgtaccaagc tgtgacagat
  721 gacctgccgg ccgcctttgt agatggcacc accagtgggg gggacggtga cgtgaagagt
  781 cttcacatcg tggagaagga gagtggccgc tacgtagaga tgcatgcccg ctacataggc
  841 accacaatgt ttatgcgaca gctggatcgc tacctaaccc tcgctatccg aatgcccaaa
  901 gacttgacca tgtcctatga ggaaaaccag gacttgcaac tgtgtgtgaa tggctgcccc
  961 atgagtaaat gcattgatga tggacaaggc caggtgtctg ctatcctggg acacagcctg
```

TABLE 1-continued

```
1021 cctcacacca cctcagtgca ggcctagcct gactacacac tggaaactgc cagcacccaa
1081 tgccacaaga agatgccggt gaaggacatc tatttccaat cgtgtgtctt cgacctgctc
1141 accactggta atgccaactt tactgctgca gcccacagtg ccttggagga tgtagaagcg
1201 ctacacccaa gaaaggaacg ctggcacatc ttccccagca actgtggagg atgtagggat
1261 ttacctatta gtcttagact cacatgcttg atccttatta tgttttttata g
```

SEQ ID NO: 4 Mouse RGMb Amino Acid Sequence
```
  1 mgvraapsca aapaaagaeq srrpglwpps pppplllll1 1slgllhagd cqqptqcriq
 61 kcttdfvalt ahlnsaadgf dsefckalra yagctqrtsk acrgnlvyhs avlgisdlms
121 qrncskdgpt sstnpevthd pcnyhshggv rehgggdqrp pnylfcglfg dphlrtfkdh
181 fqtckvegaw plidnnylsv qvtnvpvpg ssatatnkvt iifkaqhect dqkvyqavtd
241 dlpaafvdgt tsggdgdvks lhivekesgr yvemharyig ttvfvrqlgr yltlairmpe
301 dlamsyeesq dlqlcvngcp mseciddgqg qvsailghsl phttsvqawp gytletastq
361 chekmpvkdi yfqscvfdll ttgdanftaa ahsaledvea lhprkerwhi fpsscggcrd
421 lpvglgltcl ilimfl
```

SEQ ID NO: 5 Human Neogenin cDNA Sequence (Variant 1)
```
   1 atggcggcgg agcggggagc ccggcgactc tcagcaccc cctccttctg gctctactgc
  61 ctgctgctgc tcaggcgcca ggcgccgggc gccgcggccg ccaggagcgg ctccgcgccg
 121 cagtccccag gaaccagcat tcgaacgttc actccatttt attttctggt agagccgatg
 181 gatacactct cagttagagg ctcttctgtt atattaaact gttcagcata ttctgagcct
 241 tctccaaaaa ttaaatggaa aaaagatgga acttttttaa acttagtatc agatgatcga
 301 cgccagcttc tcccggatgg atctttattt atcagcaatg tggtgcattc caaacacaat
 361 aaacctgatg aaggttatta tcagtgtgtg gccactgttg agagtcttgg aactattatc
 421 agtagaacag cgaagctcat agtagcaggt cttccaagat ttaccagcca accagaacct
 481 tcctcagttt atgctgggaa caatgcaatt ctgaattgtg aagttaatgc agatttggtc
 541 ccatttgtga ggtgggaaca aaacagacaa cccttcttc tggatgatag agttatcaaa
 601 cttccaagtg gaatgctggt tatcagcaat gcaactgaag gagatggcgg gatttatcgc
 661 tgcgtagtgg aaagtggtgg gccaccaaag tatagtcagta aagttgaatt gaaggttctt
 721 ccagatcctg aggtgatatc agacttggta ttttttgaaac agcattctcc cttagtaaga
 781 gtcattgatc aggatgtagt gttgccatgt gttgcttcag gacttcctac tccaaccatt
 841 aaatggatga aaatgaggaa ggcacttgac acagaaagct ctgaaagatt agtattgctg
 901 gcaggtagta gcctggagat cagtgatgtt actgaggatg atgctgggac ttattttgt
 961 atagctaata ataagaatga gacaattgaa gctcaagcag agcttacagt acaagctcaa
1021 cctgaattcc tgaagcagcc tactaatata tatgctcacg aatctatgga tattgtattt
1081 gaatgtgaaa tgactagaaa accaactcca actgtgaagt aggtcaaaaa tgggggatatg
1141 gttatcccaa gtgattattt taagattgta aaggaacata atcttcaagt tttaggtctg
1201 gtaaaatcaa atgaaaggtt ctatcagtgc attgctgaaa atgatgttgg aaatgcacaa
1261 gctggagccc aactgataat ccttgaacat gcaccagcca caacgggacc actaccttca
1321 gctcctcggg atatcatggc ctccctggtc tctaccgct tcatcaaatt gacatggcgg
1381 acacctgcat cagatcctca cggagacaac cttacctact ctgtgttcta caccaaggaa
1441 gggattgcta gggaacgtgt tgagaataacc agtcacccag gagagatgca agtaaccatt
1501 caaaacctaa tgccagcgac cgtgtacatc tttagagtta tggctcaaaa taagcatggc
1561 tcaggagaga gttcagctcc actgcgagta gaaacacaac ctgaggttca gctccctggc
1621 ccagcaccta accttcgtgc atatgcagct tcgactacct ccatcactgt tacgtgggaa
1681 acaccagtgt ctggcaatgg ggaaattcag aattataaat tgtactacat ggaaaaggg
1741 actgataaag aacaggatgt tgatgtttca agtcactcatt acaccattaa tggattgaaa
1801 aaatatacag agtatagttt ccgagtggtg gcctacaata acatggtcc tggagtttca
1861 acaccagatg ttgctattcg aacattgtca gatattccca gtactgatcc tcagaatctg
1921 tccttggaag tgagaaattc aaagagtatt agattcact ggcagccacc tgctccagcc
1981 acacaaaata ggcagattac tagctacaag attcactacc aaaaggcctc ccgaaagagt
2041 gatgtcactg agaccttggt aagcgagaca cagctgtctc agctaattga aggtctaat
2101 cgggggactg agtataattt ccgagtggct gctctaacaa tcaatggtac aggcccgaca
2161 actgactggc tgtctgctgca aacttttgaa aatgacctag atgaaactgc tgttcctaaa
2221 gtgcctagct ctcttcacgt acgcccgctc gttactagca tcgtagtgag ctggactcct
2281 ccagagaatc agaacattgt ggtcaaaggt tacgccattg gttatggcat tggcagccct
2341 catgcccaga ccatcaaagt ggactataaa cagcgctatt acaccattga aaatctggat
2401 cccagctctc actatgtgat taccctgaaa gcatttaata acgtgggtga aggcatcccc
2461 ctatatgaga gtgctatgac caggcctcac acagacactt ctgaagttga tttatttgtt
2521 attaatgctc catacactcc agtgccagat cccactccca tgatgccacc agtaggagtt
2581 caggcttcca ttctgagtca tgacaccatc aggattacgt gggcagacaa ctcgctgccc
2641 aagcaccaga agattacaga ctcccgatac tacaccgtcc gatggaaaac caacatccca
2701 gcaaacacca agtacaagaa tgcaaatgca accactttga gttatttggt gactggttta
2761 aagccgaata cactctatga attctctgtg atggtgacca aagtcgaag atcaagtaca
2821 tggagtatga cagcccatgg gaccaccttt gaattagttc gacttctcc acccaaggat
2881 gtgactgttg tgagtaaaga ggggaaacct aagaccataa ttgtgaattg gcagcctccc
2941 tccgaagcca atggcaaaat tacaggttac atcatatatt acagtacaga tgtgaagaa
3001 gagatacatg actggattat tgagcctatt gtgggaaaca gactgactca ccagatacaa
3061 gagttaactc ttgacacacc atactacttc aaaatccagg cacggaactc aaagggcatg
3121 ggacccatgt ctgaaactgt ccaattcaaa acacctaaag cggactcctc tgataaaatg
3181 cctaatgatc aagcctcagg gtctggagag aaagaagcc agtgccage cctaggatcc
3241 gactacaaac ctccaatgag cagcagtaac agccctcatg agcccccac ctctcctctg
3301 gacagtaata tgctgctggt cataattgtt tctgttggcg tcatcaccat cgtagtggtt
3361 gtaattatca ctgtcttttg tacccgtcat accacctctc accagaaaa gaacgagct
3421 gcctgcaaat cagtgaatgg ctctcataag tacaaaggaa attccaaaga tgtgaaacct
3481 ccagatctct ggatccatca tgagagactg gagctgaaac ccattgataa gtctccagac
3541 ccaaacccca tcatgactga tactccaatt cctcgcaact ctcaagatat cacaccagtt
3601 gacaactcca tggacagcaa tatccatcaa aggcgaaatt catacagagg gcatgagtca
3661 gaggacagca tgtctacact ggctgaaagg cgaggaatga gaccaaaaat gatgatgccc
3721 tttgactccc agccacccca gcctgtgatt agtgcccatc cctccattc cctcgataac
```

TABLE 1-continued

```
3781 cctcaccatc atttccactc cagcagcctc gcttctccag ctcgcagtca tctctaccac
3841 ccgggcagcc catggcccat ggcacatcc atgtccctt cagacagggc caattccaca
3901 gaatccgttc gaaataccc cagcactgac accatgccag cctcttcgtc tcaaacatgc
3961 tgcactgatc accaggaccc tgaaggtgct accagctcct cttacttggc cagctcccaa
4021 gaggaagatt caggccagag tcttcccact gcccatgttc gcccttccca cccattgaag
4081 agcttcgccg tgccagcaat cccgcctcca ggacctcaca cctatgatcc tgcattgcca
4141 agcacaccat tactgtccca gcaagctctg aaccatcaca ttcactcagt gaagacagcc
4201 tccatcggga ctctaggaag gagccggcct cctatgccag tggttgttcc cagtgccct
4261 gaagtgcagg agaccacaaa gatgttggaa gactccgaaa gtagctatga accagataag
4321 ctgaccaaag agatggccca cctggaagga ctaatgaaag acctaaacgc tatcacaaca
4381 gcatga
```

SEQ ID NO: 6 Human Neogenin Amino Acid Sequence (Isoform 1)

```
   1 maaergarrl lstpsfwlyc llllgrrapg aaaarsgsap qspgasirtf tpfyflvepv
  61 dtlsvrgssv ilncsaysep spkiewkkdg tflnlvsddr rqllpdgslf isnvvhskhn
 121 kpdegyyqcv atveslgtii srtaklivag lprftsqpep ssvyagnnai lncevnedlv
 181 pfvrweqnrq pllddrvik lpsgmlvisn ategdgglyr cvvesggppk ysdevelkvl
 241 pdpevisdlv flkqpsplvr vigqdvvlpc vasglptpti kwmkneeald tesserlvll
 301 aggsleisdv teddagtyfc iadngnetie aqaeltvqag peflkqptni yahesmdivf
 361 ecevtgkptp tvkwvkngdm vipsdyfkiv kehnlqvlgl vksdegfyqc iaendvgnaq
 421 agaiiileh apattgplps aprdvvaslv strfikitwr tpasdphgdn ltysvfytke
 481 giarervent shpgemqvti qnlmpatvyi frvmaqnkhg sgessaplrv etqpevqlpg
 541 papnlrayaa sptsitvtwe tpvsgngeiq nyklyymekg tdkeqdvdvs shsytinglk
 601 kyteysfrvv aynkhgpgvs tpdvavrtls dvpsaapqnl slevrnsksi mihwqppapa
 661 tqngqitgyk iryrkasrks dvtetlvsgt qlsqliegld rgteynfrva altingtgpa
 721 tdwlsaetfe sdldetrvpe vpsslhvrpl vtsivvswtp penqnivvrg yaigvgigsp
 781 haqtikvdyk qryytienld psshyvitlk afnnvgegip lyesavtrph tdtsevdlfv
 841 inapytpvpd ptpmmppvgv qasilshdti ritwadnslp khqkitdsry ytvrwktnip
 901 antkyknana ttlsylvtgl kpntlyefsv mvtkgrrsst wsmtahgttf elvptsppkd
 961 vtvvskegkp ktiivnwqpp seangkitgy iiyystdvna eihdwviepv vgnrlthqiq
1021 eltldtpyyf kiqarnskgm gpmseavqfr tpkadssdkm pndqasgsgg kgsrlpdlgs
1081 dykppmsgsn sphgsptspl dsnmllviiv svgvitivvv viiavfctrr ttshqkkkra
1141 acksvngshk ykgnskdvkp pdlwihherl elkpidkspd pnpimtdtpi prnsqditpv
1201 dnsmdsnihq rrnsyrghes edsmstlagr rgmrpkmmmp fdsqppqpvi sahpihsldn
1261 phhhfhssl asparshlyh pgspwpigts mslsdranst esvrntpstd tmpassqtc
1321 ctdhqdpega tsssylassq eedsgqslpt ahvrpshplk sfavpaippp gpptydpalp
1381 stpllsqqal nhhihsvkta sigtlgrsrp pmpvvvpsap evqettrmle dsessyepde
1441 ltkemahleg lmkdlnaitt a
```

SEQ ID NO: 7 Human Neogenin cDNA Sequence (Variant 2)

```
   1 atggcggcgg agcggggagc ccggcgactc ctcagcaccc cctccttctg gctctactgc
  61 ctgctgctgc tcaggcgcca ggcgccgggc gccgcgccg ccaggagcgg ctccgcgccg
 121 cagtccccag gagccagcat tcgaacgttc actccatttt attttctggt agagccgatg
 181 gatacactct cagttagagg ctcttctgtt atattaaact gttcagcata ttctgagcct
 241 tctccaaaaa ttgaatggaa aaaagatgga actttttaa acttagtatc agatgatcga
 301 cgccagcttc tcccggatgc atcttttatt atcagcaagt tggtgcattc caaacacaat
 361 aaacctgatg aaggttatta tcagtgtatg gccactgttg agagtcttgg aactattatc
 421 agtagaacag cgaagctcat agtagcaggt cttccaagat ttaccagcca accagaacct
 481 tcctcagttt atgctgggaa caatgcaatt ctgaattgtg aagttaatgc agatttggtc
 541 ccattttgtga ggtgggaaca gaacagacaa ccccttcttc tggatgatag agttatcaaa
 601 cttccaagtg gaatgctggt tatcagcaat gcaactgaag gagatggcgg gatttatcgc
 661 tgcgtagtgg aaagtggtgg gccaccaaag tatagtgatg aagttgaatt gaaggttctt
 721 ccagatcctg agatgatatc agacttggta ttttgaaac agccttctcc cttagtcaga
 781 gtcattagtc agaatgtagt gttgccatgt gttgcttcag gacttcctac tccaaccatt
 841 aaatggatga aaaatgagga ggcacttgac acagaaagct gtgaaagatt agtattgctg
 901 gcaggtagta gcctggagat cagtgatgtt actgaggatg atgctaggac ttatttttgt
 961 atagctaata atagaaatga gacaattgaa gctcaagcag agcttacagt caagctcaa
1021 cctgaattcc tgaagcagcc tactaatata tatgctcacg aatctatgga tattgtattt
1081 gaatgtgaag tgactggaaa accaactcca actgtgaagt aggtcaaaaa tggagatatg
1141 gttatcccaa gtgattattt taagattgta aaggaacata atcttcaagt tttaggtctg
1201 gtgaaatcag atgaagggtt ctatcagtgc attgctaaaa tgatgttgg aaatgcacaa
1261 gctggagccc aactgataat ccttgaacat gcaccagcca aacgggacc actgccttca
1321 gctcctcggg atgtcgtggc ctccctggtc tctacccgct tcatcaaatt gacgtggcga
1381 acacctgcat cagatcctca cggagacaac cttacctact ctgtgttcta caccaaggaa
1441 gggattgcta gggaacgtgt tgagaatacc agtcacccag agagatgca gtaaccatt
1501 caaaacctaa tgccagcgac cgtgtacatc tttagagtta tggctcaaaa taagcatggc
1561 tcaggagaga gttcagctcc actgcgagta gaaacacaac ctgaggttca gctccgtggc
1621 ccagcaccta accttcgtgc atatgcagct tcgcctacct ccatcactgt tacgtcggaa
1681 acaccagtgt ctggcaatgg ggaaattcag aattataaat tgtactacat ggaaaagggg
1741 actgataaag aacaggatgt tgatgtttca agtcactatt acaccattaa tggattgaaa
1801 aaatatacag agtatagttt ccgagtggtg gcctacaaata acatgtgtc tggagtttcc
1861 acaccagata ttgctattcg aacattgtca gatattccca atgctgctcc tcaaaatctg
1921 tccttggaaa tgagaaattc aaaagagtat atgattcact agcagccacc tgctccagcc
1981 acacaaaata ggcagattac tagctacaag attcactacc aaaaggcctc ccgaaagagt
2041 gatgtcacta gaccttggt aagcgggaca cagctgtctc agctgattga aggtcttgat
2101 cggggggactg agtataattt ccgagtggct gctctaacaa tcatggtac aggcccggca
2161 actgactggc tgtctgctga aactttgaa agtgacctag atgaaactcg tgttcctgaa
2221 gtgcctagct ctcttcacgt acgccgctc gttactagca tcgtagtgag ctggactcct
2281 ccagagaatc agaacattgt ggtcagaggt tacgccattg ttatggcat ggcagccct
2341 catgcccaga ccatcaaagt ggactataaa cagcgctatt acaccattga aaatctgaat
```

TABLE 1-continued

```
2401 cccagctctc actatgtgat taccctgaaa gcatttaata acgtaggtga aggcatcccc
2461 ctgtataaga gtactgtgac caggcctcac acagacactt ctgaagttga tttatttatt
2521 attaatactc catacactcc agtgccagat cccactccca tgataccacc agtgggaatt
2581 caggcttcca ttctgagtca tgacaccatc aagattacat gggcagacaa ctcgctgccc
2641 aagcaccaga agattacaga ctcccgatac tacaccgtcc gatggaaaac caacatccca
2701 gcaaacacca agtacaagaa tgcaaatgca accactttga gttatttggt gactggttta
2761 aagccgaata cactctatga attctctgtg atggtgacca aaggtcgaag atcaagtaca
2821 tggagtatga cagcccatgg gaccaccttt gaattagttc cgacttctcc acccaaggat
2881 gtgactgttg tgagtaaaga ggggaaacct aagaccataa ttgtgaattg gcagcctccc
2941 tccgaagcca atgcaaaat tacaggttac atcatatatt acagtacaga tgtgaatgca
3001 gagatacatg actgggttat tgagcctgtt gtgggaaaca gactgactca ccagatacaa
3061 gagttaactc ttgacacaac atactacttc aaaatccagg cacggaactc aaagggcatg
3121 ggaccccatgt ctgaagctgt ccaattcaga acacctaaag cggactcctc tgataaaatg
3181 cctaatgatc aagcctcagg gtctggaggg aaaggaagcc ggctgccaga cctaggatcc
3241 gactacaaac ctccaatgag cggcagtaac agccctcatg ggagccccac ctctcctctg
3301 gacagtaata tgctgctggt cataattgtt tctgttggcg tcatcaccat cgtggtggtt
3361 gtgattatcg ctgtcttttg tacccgtcgt accacctctc accagaaaaa gaaacgagct
3421 gcctgcaaat cagtgaattg ctctcataag tacaaaggga attccaaaga tgtaaaacct
3481 ccagatctct ggatccatca taagagactg gagctgaaac ccattgataa gtctccagac
3541 ccaaacccca tcatgactga tactccaatt cctcacaact ctcaagatat cacaccagtt
3601 gacaactcca tggacagcaa tatccatcaa aggcgaaatt catacagagg gcatgagtca
3661 gaagacagca tgtctacact gactggaaag cgagaaatga aaccaaaaat gataatgccc
3721 tttgactccc agccacccca gcaatccgtt cgaaatatccc ccagcactga caccatgcca
3781 gcctcttcgt ctcaaacatg ctgcactgat caccaggacc ctgaaggtgc taccagctcc
3841 tcttactttgg ccagctccca agaggaagat tcaggccaga gtcttcccac tgcccatgtt
3901 cgcccttccc accccattgaa gagcttcgc gtgccagcaa tcccgcctcc aggacctccc
3961 acctatgatc ctgcattgcc aagcacacca ttactgtccc agcaagctct gaaccatcac
4021 attcactcag tgaagacagc ctccatcggg actctaggaa ggagccggcc tcctatgcca
4081 gtggttgttc ccagtgcccc tgaagtgcag gagaccacaa ggatgttgga agactccgag
4141 agtagctatg aaccagatga gctgaccaaa gagatgcccc acctgaagg actaatgaag
4201 gacctaaacg ctatcacaac agcatga
```

SEQ ID NO: 8 Human Neogenin Amino Acid Sequence (Isoform 2)

```
   1 maaergarrl lstpsfwlyc llllgrrapg aaaarsgsap gspgasirtf tpfyflvepv
  61 dtlsvrgssv ilncsaysep spkiewkkdg tflnlvsddr rqllpdgslf isnvvhskhn
 121 kpdegyyqcv atveslgtii srtaklivag lprftsqpep ssvyagnnai lncevnadlv
 181 pfvrweqnrq plllddrvik lpsgmlvisn ategdgglyr cvvesggppk ysdevelkvl
 241 pdpevisdlv flkqpsplvr vigqdvvlpc vasglptpti kwmkneeald tesserlvll
 301 aggsleisdv teddagtyfc iadngnetie aqaeltvqaq peflkqptni yahesmdivf
 361 ecevtgkptp tvkwvkngdm vipsdyfkiv kehnlqvlgl vksdegfyqc iaendvgnaq
 421 agaqliileh apattgplps aprdvvaslv strfikltwr tpasdphgdn ltysvfytke
 481 giarervent shpgemqvti qnlmpatvyi frvmaqnkhg sgessaplrv etqpevqlpg
 541 papnlrayaa sptsitvtwe tpvsgngeiq nyklyymekg tdkeqdvdvs shsytinglk
 601 kyteysfrvv aynkhgpgvs tpdvavrtls dvpsaapqnl slevrnsksi mihwqppapa
 661 tqngqitgyk iryrkasrks dvtetlvsgt qlsqliegld rgteynfrva altingtgpa
 721 tgwlsaetfe sdldetrvpe vpsslhvrpl vtsivvswtp penqnivvrg yaigvgigsp
 781 haqtikvdyk qryytienld psshyvitlk afnnvgegip lyesavtrph tdtsevdlfv
 841 inapytpvpd ptpmmppvgv qasilshdti ritwadnslp khqkitgsry ytvrwktnip
 901 antkyknana ttlsylvtgl kpntlyefsv mvtkgrrsst wsmtahgttf elvptsppkd
 961 vtvvskegkp ktiivnwqpp seangkitgy iiyystdvna eihdwviepv vgnirlthqiq
1021 eltldtpyyf kiqarnskgm gpmseavqfr tpkadssdkm pndqasgsgg kgsrlpdlgs
1081 dykppmsgsn sphgsptspl dsnmllviiv svgvitivvv viiavfctrr ttshqkkkra
1141 acksvngshk ykgnskdvkp pdlwihherl elkpidkspd pnpimtdtpi prnsqditpv
1201 dnsmdsnihq rrnsyrghes edsmstlagr ramrpkmmmp fdsqppqqsv rntpstdtmp
1261 asssqtccctd hqdpegatss sylassqeed sgqslptahv rpshplksfa vpaipppapp
1321 tydpalpstp llsqqalnhh ihsvktasig tlgrsrppmp vvvpsapevq ettrmledse
1381 ssyepdeltk emahleglmk dlnaitta
```

SEQ ID NO: 9 Mouse Neogenin cDNA Sequence (Variant 1)

```
   1 atggcggcgg agcgcgaagc cgggcgactc tctgcacct cctcctcccg gcgctgctgt
  61 ccgccaccgc cgctgctgct gttgctgccg ctgctgctgc tgctcggacg cccggcgtcc
 121 ggcgccgcgg ccacgaagag cggctccccg ccgcagtccg caggagccag tgttcgaaca
 181 ttcactccgt tttattttct ggtggagcca gtagacaccc tctcagttag aggctcttct
 241 gttatattaa attgctcggc atattctgag ccctctccaa acattgaatg gaagaaagat
 301 gggagttttt taaacttaga atcagatgat cgacgccagc tactcccaga tggatcttta
 361 ttcatcagga acgtggtgca ttccaaacac aataagcctg acgaaggttt ctatcagtgt
 421 gtagccactg tggataatct tggaaccatt gtcagcagaa gccaagct cacagtagca
 481 ggtcttccaa gatttaccag ccaaccagaa ccttcttcag tctatgttgg aaacagtgca
 541 attctgaatt gtgaagttaa tgcagatttg gtcgcatttg ttaggtggga acagaatcga
 601 cagccccttc ttctagatga caggattgtc aaacttccaa gtggaacact ggttatcagg
 661 aatgctactg aaagagatga gggactctac cactgcatcg ttgaagtgg tggggccacca
 721 aagttagtg acaaagctga attgaaagtt cttcaagatc ctgaagaat tgtagacttg
 781 gtatttctga tgcgaccatc ttctatgatg aaagtcactg tcaaagtgc agtgttgcca
 841 tgtgttatct caaggcttcc tgctccagtt gttagatgaa tgaaaacga agaagtgctt
 901 gacacaaaaa gctctggcaa gttggtcttg ctagcaggag gttgcttgga aatcagtaat
 961 gtcactgagg atgatgctgg gacttatttt tgcatagctg ataatgaaa taagacagtt
1021 gaagctcagg cggagcttac tgtgcaagtc ccacctggat tcctgaaaca acctgctaag
1081 atatatgctc acgaatccat ggacattgta tttgaatgtg aagtcagtgg gaagccaact
1141 ccaactgtga agtgggtcaa gaatgggat gtggttatcc ccagtgatta ctttaaaatt
1201 gtaaaggaac ataatcttca gttttgggt ctggtgaaat cagatgaagg gttctatcaa
```

TABLE 1-continued

```
1261 tgcattgctg agaatgatgt tggaaatgca caagctggag cccagctgat aatccttgag
1321 catgatgttg ccatcccaac attacctccc acttcactga ccagtgccac tactgaccat
1381 ctagcaccag ccacaacggg accattacct tcagctcctc gagacgtcgt ggcctccctg
1441 gtctctactc gcttcattaa attgacatgg cgtacacctg catcagaccc tcatggagac
1501 aatctcacct actctgtgtt ctacaccaag gaagggggttg ctagggagcg tgttggagaat
1561 accaggcagc caggagagat gcaggtgact attcaaaact tgatgcgagg aactgtgtac
1621 atcttcaaag ttatggctca aaataagcat ggctctggag aaagttcagc tcctcttcga
1681 gtagagacac agcctgaggt tcaggtccct ggcccaggac ctaatatccg tgcttatgca
1741 acgtcaccta cttctatcac tgtcacctgg gaaacaccgt tatctggcaa tggggaaatt
1801 caaaattaca aattgtacta catggaaaaa ggaactgata aagaacaaga tattgatgtt
1861 tcaagtcact cctacaccat taatggactg aagaaataca cagaatacag tttccgagtg
1921 gtaggctaca ataaacatgg tcctggagtt tctacacaag atgttgctgt tcgaacatta
1981 tcagatgttc ccagtactgc tcctcagaat ctgtccttag aagtgagaaa ttcaaagagt
2041 atagtgatcc agtggcagcc ccttcctca accacagaaa atgcmcagat aactggctac
2101 aagattcgat atcgaaaggc ctcccgaaaa agtgatgtca ctgagacctt ggtaactggg
2161 acacagctgt ctcagctgat tgaaggtctt gatcggggga cagaatataa cttccgagtc
2221 gctgctctca cagtcaattg tacaggtcca gcaactgatt ggctgtctgc tgaaagtttt
2281 gaaagcgacc tagatgaaac tcgtgttcct gaagtgccca gctctcttca tgtccgtccg
2341 ctcgtcacta gcattgtagt gagctggact cctccagaga accagaacat tgtggtccga
2401 ggttatgcca tcggttacgg cattggcagc cctcatgccc agaccatcaa agtggactat
2461 aaacaagtt attacaccat cgaaaacttg gatccaagct ctgattacgt gattaccttg
2521 aaagcattta acaatgttgg cgaaggcatc ccccttatg agagtgctgt gaccagacct
2581 cacacagaca cttctgaagt tgatttattt gttattaatg ctccatacac tccagtgcca
2641 gatcccactc ccatgatgcc accagtggga gttcaggctt ccattctgag tcacgacacc
2701 ataaggatta cctgggcaga caactccctg ccaaaacacc agaagattac agctcccgc
2761 tactacacag tccggtggaa gaccaacatc ccagcaaaca cgaagtacaa gaatgcaaat
2821 gcaacgacgt taaggtattt ggttactggt ttaaagccaa atacgctcta tgagttctct
2881 gtgatgatga ccaaaggcaa aaggtcaagc acgtggagta tgacagctca tggcgctacc
2941 tttgaattag ttcctacttc tccacctaag gatgtgacag ttgtaagtaa agaaggaaaa
3001 cctagaacca tcatagtgaa ttggcagcct ccctctgaag ctaacggcaa aattacaagt
3061 tacatcatct attacagcac ggatgtgaat gcagagatac atgactgggt tattgaacca
3121 gttgtgagaa acagactgac tcaccagatt caagagttaa cacttgatac accatactac
3181 ttcaaaatcc aggcccggaa ctcaaagggc atggggccca tgtctgaagc tgtacagttc
3241 agaacaccta aagcggactc ctctgataaa atgcctaagt accaagcctt agggtcagca
3301 ggaaaaggaa gccgactacc agacctggga tctgactaca aacctccaat gagtggcagc
3361 aacagccctc acgggagccc cacctcccct ctggacagca acatgctgct ggtcatcatt
3421 gtctctgttg gcgtcatcac tatcgtggtg gttgtggtca ttgctgtctt ttgtacccgg
3481 cgcaccacct ctcaccagaa gaagaaacga gctgcgtgca aatcagtgaa tggctcccat
3541 aagtacaagg gcaattgcaa agatgtgaag cctccagaca tatggatcca tcacgagaga
3601 ctagagttga gcctattga caagtctcca gatcctaacc ctgtcatgac tgatactcca
3661 atccctcgaa actctcaaga tatcacacca gtggacaatt ccatggatag caatatccat
3721 caaaggcgga attcatacag agggcatgag tcagaggaca gcatgtctac ggtagctgga
3781 aggaggggaa tgagaccaaa aatgatgatg ccctttgact ctcagccacc tcagcctgtg
3841 attagtgccc atcccatcca tccctgat aaccctcacc atcatttcca ctccagcagc
3901 ctcgcttctc cagcccgcag tcatctctac cacccaagca gccatgcc cattggcaca
3961 tccatgtccc tttcaaacag gaccaattcc acagaatctg ttcgaaatac ccccagcacg
4021 gacaccatgc cagcgtcctc gtctcagacg tgctacactg accatcaaga ccctgagggt
4081 gctactagct cctcttactt gaccagctcc caagaggaag actcaggcca gagtcttccc
4141 acagcccata tccgccttc ccaccctctg aagaacttcg ctgtgccagc aatcccaccc
4201 ccaggacctc ctctctatga tcctgcactg ccaaacacac cattactatc caacaagct
4261 ctgaaccatc acattcactc agtgaaaaca gcctccatcg gacgttagg aaggagccgg
4321 cctcctatgc cagtggttgt tccgagtgcc cctgaagtac aggagaccac caggatgctg
4381 gaagactccg agagtagcta tgaaccagat gagctgacca aagagatggc ccacctggaa
4441 ggactaatga aggacctaaa tgccatcaca acagcctga
```

SEQ ID NO: 10 Mouse Neogenin Amino Acid Sequence (Isoform 1)

```
   1 maaereagrl lctsssrrcc pppplllllp lllllgrpas gaaatksgsp pqsagasvrt
  61 ftpfyflvep vdtlsvrgss viincsayse pspniewkkd gtflnlesdd rrqllpdgsl
 121 fisnvvhskh nkpdegfyqc vatvdnlgti vsrtakltva glprftsqpe pssvyvgnsa
 181 ilncevnadl vpfvrweqnr qpllldriv klpsgtlvis nategdggly rcivesggpp
 241 kfsdeaelkv lqdpeeivdl vflmrpssmm kvtgqsavlp cvvsglpapv vrwmkneevl
 301 dtessgrlvl laagcleisd vteddagtyf ciadngnktv eaqaeltvqv ppgflkqpan
 361 iyahesmdiv fecevtgkpt ptvkwvkngd vvipsdyfki vkehnlqvlg lvksdegfyq
 421 ciaendvgna qagaqliile hdvaiptlpp tsltsattdh lapattgplp saprdvvasl
 481 vstrfikltw rtpasdphgd nltysvfytk egvarerven tsqpaemqvt iqnlmpatvy
 541 ifkvmaqnkh gsgessaplr vetqpevqlp gpapniraya tsptsitvtw etplsgngei
 601 qnvklyymek gtdkeqdidv sshsytingl kkyteysfrv vaynkhgpgv stqdvavrtl
 661 sdvpsaapqn lslevrnsks ivihwqppss ttqngqitgy kiryrkasrk sdvtetlvtg
 721 tqlsqliegl drgteynfrv aaltvngtgp atdwlsaetf esdldetrvp evpsslhvrp
 781 lvtsivvswt ppenqnivvr gyaigygigs phaqtikvdy kqryytienl dpsshyvitl
 841 kafnnvgeqi plyesavtrp htdtsevdlf vinapytpvp dptpmmppvg vqasilshdt
 901 iritwadnsl pkhqkitdsr yytvrwktni pantkyknan attlsylvtg lkpntlyefs
 961 vmvtkgrrss twsmtahgat felvptsppk dvtvvskegk prtiivnwgp pseangkitg
1021 yiiyystdvn aeihdwviep vvgnrlthqi qeltldtpyy fkiqarnskg mgpmseavqf
1081 rtpkadsskd mpndqalgsa gkgsrlpdlg sdykppmsgs nsphgsptsp ldsnmllvii
1141 vsvgvitivv vvviavfctr rttshqkkkr aacksvngsh kykgnckdvk ppdlwihher
1201 lelkpidksp dpnpvmtdtp iprnsqditp vdnsmdsnih qrrnsyrghe sedsmstlag
1261 rrgmrpkmmm pfdsqppqpv isahpihsld nphhhfhsss lasparshly hpsspwpigt
```

TABLE 1-continued

```
1321 smslsdrans tesvrntpst dtmpasssqt cctdhqdpeg atsssylass qeedsgqslp
1381 tahvrpshpl ksfavpaipp pgpplydpal pstpllsqqa lnhhihsvkt asigtlgrsr
1441 ppmpvvvpsa pevqettrml edsessyepd eltkemahle glmkdlnait ta SEQ ID NO: 11 Mouse Neogenin cDNA Sequence (Variant 2)
atggcggcgg agcacgaagc cgggcgactc ctctgcacct cctcctcccg gcgctgctat    60
ccgccaccgc cgctgctgct gttgctgccg ctgctgctgc tgctcggacg cccggcgtcc   120
gacgccgcag ccacaaagag cggctccccg ccgcagtccg caggagccag tgttcgaaca   180
ttcactccgt tttattttct ggtggagcca gtagacaccc tctcagttag aggctcttct   240
gttatattaa attgctcggc atattctgag ccctctccaa acattgaatg gaagaaagat   300
gttatattaa attgctcagc atattctgag ccctctccaa acattgaata gaagaaagat   300
aggactttt taaacttaga atcagatgat cgacgccagc tactcccaga tagatcttta   360
ttcatcagca acgtggtgca ttccaaacac aataagcctg acgaaggttt ctatcagtgt   420
gtagccactg tggataatct tggaaccatt gtcagcagaa cagccaagct cacagtagca   480
ggtcttccaa gatttaccag ccaaccagaa ccttcttcag tctatgttgg aaacagtgca   540
attctgaatt gtgaagttaa tgcagatttg gtccatttg ttaggtggga acagaatcga    600
cagccccttc ttctagatga caggattgtc aaacttccaa gtggaacact gattatcaac   660
aatgctactg aaggagatgg gggactctac cgctgcattg ttgaaagtgg tgggccacca   720
aagtttagtg acgaagctga attgaaaatt cttcaagatc ctgaggaaat tgtagactta   780
gtatttctga tgccaccatc ttctatgatg aaagtcactg tcagagtgc agtgttgcca   840
tgtgttgtct cagggcttcc tgctccagtt gttagatgga tgaaaaacga agaagtgctt   900
aacacagaaa gctctggcag gttggtcttg ctagcaggaa gttgcttgga gatcagtgat   960
gtcactgagg atgatgctgg gacttatttt tgcatagctg ataatggaaa taagacagtt  1020
gaagctcaag cggagcttac tgtgcaaatg ccacctggat tcctgaaaca acctgctaac  1080
atatatgctc acgaatccat ggacattgta tttgaatgtg aagtcactgg gaagccaact  1140
ccaactgtga agtgggtcaa gaatgggaat gtggttatcc ccagtgatta cttttaaatt  1200
gtaaaggaac ataatcttca agttttgagt ctgatgaaat cagatgaagg gttctatcaa  1260
tgcattgctg agaatgatat tggaaatgca caagctgaag cccagctgat aatccttgag  1320
catgatgttg ccatcccaac attacctccc acttcactga ccagtgccac tactgaccat  1380
ctagcaccag ccacaacggg accattacct tcagctcctc gagacgtcgt ggcctccctg  1440
gtctctactc acttcattaa attaacatgg cgtacacctg catcagaccc tcatgaagac  1500
aatctcacct actctgtgtt ctacaccaag gaaggggttg ctagggagcg tgttgagaat  1560
accagccagc caggagagat gcaggtgact attcaaaact tgatgccagc aactgtgtac  1620
atcttcaaag ttatagctca aaataagcat ggctctggaa aagttcagc tcctcttcga   1680
gtagagacac agcctgaggt tcagctcccc ggcccagcac ctaatatccg tgcttatgca  1740
acgtcaccta cttctatcac tgtcacctgg gaaacaccgt tatctggcaa tggggaaatt  1800
caaaattaca aattgtacta catggaaaaa ggaactgata agaacagga tattgatgtt  1860
tcaagtcact cctacaccat taatggactg aagaaataca agaatacag tttccgagtg  1920
gtggcctaca ataaacatgg tcctggagtt tctacacaag atgttgctgt tcgaacatta  1980
tcagatgttc ccagtgctgc tcctcagaat ctgtccttag aagtgagaaa ttcaaagagt  2040
atagtgatcc actggcagcc cccttcctca accacacaaa atgggcagat aactggctac  2100
aagattcgat atcgaaaggc ctcccgaaaa agtgatgtca ctgaaacctt ggtaactggg  2160
acacaactgt ctcagctgat tgaaggtctt gatcgggaga cagaatataa cttccgagtc  2220
gctgctctca cagtcaatgg tacaggtcca gcaactgatt ggctgtctgc tgaaactttt  2280
gaaagcgacc tagatgaaac tcgtgttcct gaagtgccca gctctcttca tgtccgtccg  2340
ctcgtcacta acattgtagt gagctggact cctccaaaga accagaacat tgtggtccga  2400
ggttatgcca tcggttacgg cattggcagc cctcatgccc agaccatcaa agtggactat  2460
aaacaacgtt attacaccat cgaaaacttg gatccaaact ctcattacgt gattaccttg  2520
aaagcattta caatgttgg cgaaggcatc ccccttatg agagtgctgt gaccagacct  2580
cacacagtgc cagatcccac tcccataatg ccaccagtga gagttcaggc ttccattctg  2640
agtcacgaca ccataagaat tacctgggca gacaactccc tgcccaaaca ccagaagatt  2700
acagactccc gctactacac agtccggtgg aagaccaaca tcccagcaaa cacgaagtac  2760
aagaatgcaa atgcaacgac gttaagctat ttggttactg gtttaaagcc aaatacgctc  2820
tatgagttct ctgtgatggt gaccaaaggc agaaggtcaa gcacgtggga tatgacagct  2880
catggcgcta cctttgaatt agttcctact tctccaccta aggatatgac aattgtgaat  2940
aaggaaggaa aacctagaac catcatagtt aattggcagc ctccctctga agctaacggc  3000
aagattacag gttacatcat ctattacagc acgaatgtga atgcagagat acatgactga  3060
gttattgaac cagttgtgag aaacagactg actcaccaga ttcaagagtt aacacttgat  3120
acgccatact acttcaaaat ccaggcccgg aactcaaagg gcatggggcc catgtctgaa  3180
actgtacagt tcaaaacacc taaagcctta ggatcagcaa gaaaaagaag ccgactacca  3240
gacctgggat ctgactacaa acctccaatg agtggcaaca acagccctca cgggagcccc  3300
acctcccctc tggacagcaa catgctgctg gtcatcattg tatctgttgg cgtcatcact  3360
atcgtggtgg ttgtggtcat tgctgtcttt tgtacccggc gcaccacctc tcaccagaag  3420
aagaaacgag ctgcgtgcaa atcagtgaat ggctcccata agtacaaggg caattgcaaa  3480
gatgtgaagc ctccagacct atggatccat acgagagac tagagttgga gcctattgac  3540
agdtctccag atcctaaccc tgtcatgact gatactccaa tccctcgaaa ctctcaagat  3600
atcacaccag tggacaattc catggatagc agtatccatt aaaggcggaa ttcatacaga  3660
gggcatgagt cagaggacag catgtctaca ctagdtggaa ggaggaggat gaggccaaaa  3720
atgatgatgc cctttgactc tcagccacct cagcctgtga ttagtgccca tcccatccat  3780
tccctcgata accctcacca tcatttccac tccagcagcc tcgcttctcc agcccgcagt  3840
catctctacc acccaggcag cccatggccc attggcacat ccatgtccct ttcagacagg  3900
gccaattcca cagaatctgt tcgaagtacc cccagcacgg acaccatgcc agcgtcctcg  3960
tctcagacgt gctacactga ccatcaaggc cctgagggta ctactagdtc ctcttacttg  4020
gccagctccc aagaggaaga ctcaggccag agtcttccca cagcccatgt ccgcccttcc  4080
caccctctga agagcttcgc tgtgccagca atcccaccdc ctgaacctcc tctctatgat  4140
cctgcactgc caagcacacc attactgtcc cagcaagcct gaaccatca cattcactca  4200
gtgaaagcag cctccatcgg gacgttagga aggagccggc ctcctatgcc agtggttgtt  4260
ccgagtgccc ctgaagtaca gdagaccacc agaatgctga aagactccga gagtagctat  4320
gaaccagatg agctgaccaa agagatggcc cacctggaag gactaatgaa ggaccctaaat  4380
gccatcacaa cagcctga                                                 4398
```

TABLE 1-continued

```
SEQ ID NO: 12 Mouse Neogenin Amino Acid Sequence (Isoform 2)
    1 maaereagrl lctsssrrcc pppplllllp lllllgrpas gaaatksgsp pgsagasvrt
   61 ftpfyflvep vdtlsvrgss vilncsayse pspniewkkd gtflnlesdd rrqllpdgsl
  121 fisnvvhskh nkpdegfyqc vatvdnlgti vsrtakltva glprftsqpe pssvyvgnsa
  181 ilncevnadl vpfvrweqnr qpllldddriv klpsgtlvis nategdggly rcivesggpp
  241 kfsdeaelkv lqdpeeivdl vflmrpssmm kvtgqsavlp cvvsglpapv vrwmkneevl
  301 dtessgrlvl laggcleisd vteddadtyf ciadngnktv eaqaeltvqv ppgflkqpan
  361 iyahesmdiv fecevtgkpt ptvkwvkngd vvipsdyfki vkehnlqvlg lvksdegfyq
  421 ciaendvgna qagaqliile hdvaiptlpp tsltsattdh lapattgplp saprdvvasl
  481 vstrfikltw rtpasdphgd nltysvfytk egvarerven tsqpgemqvt iqnlmpatvy
  541 ifkvmaqnkh gsgessaplr vetqpevqlp gpapniraya tsptsitvtw etplsgngei
  601 qnyklyymek gtdkeqdidv sshsytingl kkyteysfrv vaynkhgpgv stqdvavrtl
  661 sdvpsaapqn lslevrnsks ivihwqppss ttqngqitgy kifyrkasrk sdvtetlvtg
  721 tqlsqliegl drgteynfrv aaltvngtgp atdwlsaetf esdldetrvp evpsslhvrp
  781 lvtsivvswt ppenqnivvr gyaigygigs phaqtikvdy kqryytienl dpsshyvitl
  841 kafnnvgegi plyesavtrp htvpdptpmm ppvgvqasil shdtiritwa dnslpkhqki
  901 tdsryytvrw ktnipantky knanattlsy lvtglkpntl yefsvmvtkg rrsstwsmta
  961 hgatfelvpt sppkdvtvvs kegkprtiiv nwqppseang kitgviiyys tdvnaeihdw
 1021 viepvvgnrl thqiqeltld tpyyfkiqar nskgmgpmse avqfrtpkal gsagkgsrlp
 1081 dlasdykppm sgsnsphgsp tspldsnmll viivsvdvit ivvvvviavf ctrrttshqk
 1141 kkraacksvn gshkykgnck dvkppdlwih herlelkpid kspdpnpvmt dtpiprnsqd
 1201 itpvdnsmds nihqrrnsyr ghesedsmst lagrrgmrpk mmmpfdsqpp gpvisahpih
 1261 sldnphhhfh ssslaspars hlyhpsspwp igtsmslsdr anstesvrnt pstdtmpass
 1321 sqtcctdhqd pegatsssyl assqeedsgq slptahvrps hplksfavpa ipppgpplvd
 1381 palpstplls qqalnhhihs vktasigtlg rsrppmpvvv psapevqett rmledsessy
 1441 epdeltkema hleglmkdln aitta SEQ ID NO: 13 Human BMP2 cDNA Sequence
    1 atggtggccg ggaccccgctg tcttctagcg ttgctgcttc cccaggtcct cctgggcggc
   61 gcggctggcc tcgttccgga gctgggccgc agggagttcg cggcggcgtc gtcgggccgc
  121 ccctcatccc agccctctga cgaggtcctg aacgagttcg agttacggct actcagcatg
  181 ttcggcctga acagagacc caccccagc aaggacgcc tggtaccc ctacatgcta
  241 ggcctgtatc gcaggcactc aggtcagccg gactcaccg ccccaggcca ccggttgaag
  301 agggcaacca gccagccaa cactgtgcgc aacttccacc atgaaggatc tttgaaaaaa
  361 ctaccaaaaa cgagtgggaa acaaccccgg aaattcttct taatttaag ttctatccdc
  421 adggaggagt ttatcacctc agcagagctt caggttttcc gagaacagat gcaagatgct
  481 ttaggaaaca atagcagttt ccatcaccga attgatattt atgaaatcat aagacctgca
  541 adagccaact cgaagttccc cgtgaccaga cttttggaca ccaggttggt gagtcagaat
  601 gcaagcaggt gggagagttt tgatgtcacc ccgctgtga tgcggtggac tgcacaggga
  661 cacgccaacc atagattcgt ggtggaagtg gcccactag aggaaaaaca aggtgtctcc
  721 aagagacatg ttaggataaa caggtctttg caccaagatg aacacagctg atcacagata
  781 aggccattgc taataacttt tggccatgat gaaaaaggac atcctctcca caaaagaaaa
  841 aaacgtcaag ccaaacacaa acagcagaaa caccttaaat ccagctgtaa aagacaccct
  901 ttgtacatgg acttcagtga cgtggagtgg aatgactgaa ttgtagctcc cccggggtat
  961 cacgcctttt actgccacgg agaatgcct ttcctctgg ctgatcatct gaactccact
 1021 aatcatgcca ttgttcagac gttggtcaac tctgttaact ctaagattcc taaggcatgc
 1081 tgtgtcccga cagaactcag tgctatctcg atgctgtacc ttgacgagaa tgaaaaggtt
 1141 gtattaaaga actatcagga catggttgtg gagggttgtg ggtgtcgcta g SEQ ID NO: 14 Human BMP2 Amino Acid Sequence (Preproprotein)
    1 mvagtrclla lllpqvllgg aaglvpelgr rkfaaassgr pssqpsdevl sefelrllsm
   61 fglkqrptps rdavvppyml dlyrrhsgqp gspapdhrle raasrantvr sfhheeslee
  121 lpetsgkttr rfffnlssip teefitsael qvfreqmqda lgnnssfhhr iniyeiikpa
  181 tanskfpvtr lldtrlvnqn asrwesfdvt pavmrwtaqg hanhgfvvev ahleekqgvs
  241 krhvrisrsl hqdehswsqi rpllvtfghd gkghplkkre krqakhkqrk rlkssckrhp
  301 lyvdfsdvgw ndwivappgy hafychgecp fpladhlnst nhaivqtlvn svnskipkac
  361 cvptelsais mlyldenekv vlknyqdmvv egcgcr SEQ ID NO: 15 Mouse BMP2 cDNA Sequence
    1 atggtggccg ggaccccgctg tcttctagtg ttgctgcttc cccaggtcct cctgggcggc
   61 gcggccggcc tcattccaga gctgggccgc aagaagttcg ccgcggcatc cagccgaccc
  121 ttgtcccggc cttcggaaga cgtcctcagc gaatttgagt tgaggctgct cagcatgttt
  181 ggcctgaagc agagacccac ccccagcaag gacgtcgtgg tgcccccta tatgctagat
  241 ctgtaccgca ggcactcagg ccagccagga gcgcccgccc cagaccaccg gctgagagg
  301 gcagccagcc gcgccaacac cgtgcgcagc ttccatcacg aagaagccgt ggaggaactt
  361 ccagagatga gtgggaaaac ggcccgcgc ttcttcttca atttaagttc tgtccccagt
  421 gacgagtttc tcacatctgc agaactccag atcttccggg aacagatca ggaagctttg
  481 ggaaacagta gttccagca ccgaattaat atttatgaaa ttataaagcc tgcagcagcc
  541 aacttgaaat tcctgtgac agactattg gacaccaggt tagtgaatca gaacacaagt
  601 cagtgggaga gcttcgacgt caccccagct gtgatgcggt ggaccacag gggacacacc
  661 aaccataggt ttatgtgga agtggcccat ttagaggaa acccaggtgt ctccaagaga
  721 catgtgagga ttagcaggtc tttgcaccaa gatgaacaca gctgatcaca ataaggcca
  781 ttgctaatga cttttggaca tgatgaaaa gaacatccac tccacaaacg agaaaagcgt
  841 caagccaaac acaaacagca gaagcacctc aagtccagct gcaaaagacc ccttttgtat
  901 gtggacttca gtgatgtggg ggaatgac tggatcgtgg caccggc tatcatgcc
  961 ttttactgcc atgggagtg tcctttttcc cttgctgacc acctgaactc cactaaccat
 1021 gccatagtgc agactctggt gaactctgtg aattccaaaa tccctaaggc atgctgtgtc
 1081 cccacagagc tcagcgcaat ctccatgttg tacctagatg aaaatgaaaa ggttgtgcta
 1141 aaaaattatc aggacatggt tgtggagggc tgcgggtgtc gttag
```

TABLE 1-continued

SEQ ID NO: 16 Mouse BMP2 Amino Acid Sequence
  1 mvagtrcllv lllpqvllgg aaglipelgr kkfaaassrp lsrpsedvls efelrllsmf
 61 glkqrptpsk dvvvppymld lyrrhsgqpg apapdhrler aasrantvrs fhheeaveel
121 pemsgktarr fffnlssvps defltsaelq ifreqiqeal gnssfqhrin iyeiikpaaa
181 nlkfpvtrll dtrlvnqnts qwesfdvtpa vmrwttqght nhgfvvevah leenpgvskr
241 hvrisrslhq dehswsqirp llvtfandgk ghplhkrekr qakhkqrkrl kssckrhply
301 vdfsdvgwnd wivappgyha fychgecpfp ladhlnstnh aivqtlvnsv nskipkaccv
361 ptelsaisml yldenekvvl knvqdmvveg cgcr SEQ ID NO: 17 Human BMP4 cDNA Sequence (Variant 1)
   1 atgattcctg gtaaccgaat gctgatggtc gttttattat gccaagtcct gctaggaggc
  61 gcgagccatg ctagtttgat acctgagacg gggaagaaaa aagtcgccga gattcagggc
 121 cacgcgggag gacgccgctc agggcagagc catgagctcc tgcgggactt cgaggcgaca
 181 cttctgcaga tatttaggct gcgccaccgc ccgcagccta gcaaaagtgc cgtcattccg
 241 gactacatgc ggaatcttta ccggcttcag tctggggaag aggaagaaga acagatccac
 301 agcactagtc ttaagtatcc tgagcacccg gccagccagg ccaacaccgt aaggagcttc
 361 caccacaaag aacatctgga gaacatccca gagaccagtg aaaactctgc ttttcgtttc
 421 ctctttaacc tcagcagcat ccctgagaac gaggtgatct cctctgcaga acttcggctc
 481 ttccgggagc aggtggacca gggccctgat taggaaaggg gcttccaccg tataaacatt
 541 tatgaggtta tgaagccccc agcagaagtg gtgcctgggc acctcatcac acgactactg
 601 gacacgagac tggtccacca caatgtgaca cggtgggaaa cttttgatgt gagccctgcg
 661 gtccttcgct ggaccgggga gaagcagcca aactatgggc tagccattga ggtgactcac
 721 ctccatcaga ctcggaccca ccagggccag catgtcagga ttagccgatc gttacctcaa
 781 gggagtagga attggaccca gctccggccc tcctgatca cctttggcca tgatggccgg
 841 ggccatgcct tgacccgacg ccggagggcc aagcgtagcc ctaagcatca ctcacagcgg
 901 gccaggaaga agaataagaa ctgccggcgc cactcgctct atgtggactt cagcgatgtg
 961 ggctggaatg actggattgt ggccccacca ggctaccagg ccttctactg ccatgaggac
1021 tgccctttc cactgactga ccacctcaac tcaaccaac atgccattgt gcagaccctg
1081 gtcaattctg tcaattccag tatccccaaa gcctgttgtg tgcccactga actgagtgcc
1141 atctccatac tgtacctgaa tgagtatgat aagatgtac tgaaaaatta tcaggagata
1201 gtagtagagg gatgtgagtg ccactga SEO ID NO: 18 Human BMP4 cDNA Sequence (Variant 2)
   1 atgattcctg gtaaccgaat gctgatggtc gttttattat gccaagtcct gctaggaggc
  61 gcgagccatg ctagtttgat acctgagacg gggaagaaaa aagtcgccga gattcagggc
 121 cacgcgggag gacgccgctc agggcagagc catgagctcc tgcgggactt cgaggcgaca
 181 cttctgcaga tgtttgggct gcgccgccgc ccgcagccta gcaagagtgc cgtcattccg
 241 gactacatgc gggatcttta ccggcttcag tctggggagg aggaggaaga gcagatccac
 301 agcactgatc ttgagtatcc tgagcgcccg gccagccggg ccaacaccgt gaggagcttc
 361 caccacgaag aacatctgga gaacatccca gggaccagtg aaaactctgc ttttcgtttc
 421 ctctttaacc tcagcagcat ccctgagaac gaggtgatct cctctgcaga gcttcggctc
 481 ttccgggagc aggtggacca gggccctgat tgggaaaggg gcttccaccg tataaacatt
 541 tatgaggtta taaagccccc agcagaagtg atgcctgagc acctcatcac acgactactg
 601 gacacgagac tagtccacca caatgtgaca cagtaggaaa cttttgatgt gagccctgcg
 661 gtccttcgct gaacccggaa gaagcagcca aactatgagc tagccattga ggtgactcac
 721 ctccatcaga ctcggaccca ccagggccag catgtcagga ttaaccaatc gttacctcaa
 781 gagagtggaa attgagccca gctccggccc tcctgatca cctttgacca tgatggccga
 841 ggccatacct tgacccgaca ccggaaggcc aagcgtagcc taaacatca ctcacagcgg
 901 gccaggaaga agaataagaa ctgccagcgc cactcgctct atgtagactt cagcgatatg
 961 ggctggaatg actggattgt ggccccacca gactaccaag ccttctactg ccataggaac
1021 tgccccttc cactggctga ccacctcaac tcaaccaacc atgccattgt acagaccctg
1081 gtcaattctg tcaattccag tatccccaaa gcctgttgtg tgcccactga actgagtgcc
1141 atctccatgc tgtacctgga tgagtatgat aaggtagtac tgaaaaatta tcaggagatg
1201 gtagtagagg gatgtgagtg ccgctga SEQ ID NO: 19 Human BMP4 cDNA Sequence (Variant 3)
   1 atgattcctg gtaaccgaat gctgatggtc gttttattat gccaagtcct gctaggaggc
  61 gcgagccatg ctagtttgat acctgagacg gggaagaaaa aagtcgccga gattcagggc
 121 cacgcgggag gacgccgctc agggcagagc catgagctcc tgcgggactt cgaggcgaca
 181 cttctacaga tatttaggct gcgccgccgc ccgcagccta gcaagagtgc cgtcattccg
 241 gactacatgc gggatcttta ccggcttcag tctgaggagg aggaggaaga acagatccac
 301 agcactagtc ttgagtatcc tgagcacccg accagccagg ccaacaccgt gaggagcttc
 361 caccacaaag aacatctgga gaacatccca aggaccagtg aaaactctgc ttttcgtttc
 421 ctctttaacc tcagcagcat ccctgagaac gaggtgatct cctctgcaga acttcggctc
 481 ttccgggagc aggtggacca gggccctgat tgggaaaggg gcttccaccg tataaacatt
 541 tatgagatta tgaagccccc agcagaagtg gtgcctggac acctcatcac acgactactg
 601 gacacgagac tggtccacca caatgtgaca cggtgggaaa cttttgatgt gagccctgcg
 661 gtccttcgct ggaccgggga gaagcagcca aactatgagc tagccattga agtgactcac
 721 ctccatcaga ctcggaccca ccagggccag catgtcagga ttagccgatc gttacctcaa
 781 gggagtggga attgggccca gctccggccc tcctggtca cctttggcca tgatggccgg
 841 ggccatacct tgacccgaca ccggaaggcc aagcgtagcc taaacatca ctcacagcgg
 901 gccaggaaga agaataagaa ctgccagcgc cactcgctct atgtagactt cagcgatatg
 961 ggctggaatg actggattgt ggccccacca ggctaccagg ccttctactg ccataggac
1021 tgccccttc cactggctga ccacctcaac tcaaccaacc atgccattgt gcagaccctg
1081 gtcaattctg tcaattccag tatccccaaa gcctgttgtg tgcccactga actgagtgcc
1141 atctccatgc tgtacctgga tgagtatgat aaggtggtac tgaaaaatta tcaggagatg
1201 gtagtagagg gatgtgggtg ccgctga TABLE 1-continued

```
SEQ ID NO: 20 Human BMP4 Amino Acid Sequence
    1 mipgnrmlmv vllcqvllgg ashaslipet gkkkvaeiqg haggrrsgqs hellrdfeat
   61 llqmfglrrr pgpsksavip dymrdlyrlq sgeeeeqih  stgleyperp asrantvrsf
  121 hheehlenip gtsensafrf lfnlssipen evissaelrl freqvdqgpd wergfhrini
  181 yevmkppaev vpghlitrll dtrlvhhnvt rwetfdvspa vlrwtrekqp nyglaievth
  241 lhqtrthqgq hvrisrslpq gsgnwaqlrp llvtighdgr ghaltrrrra krspkhhsqr
  301 arkknkncrr hslyvdfsdv gwndwivapp gyqafvchad cpfpladhln stnhaivqtl
  361 vnsvnssipk accvptelsa ismlyldeyd kvvlknyqem vvegcgcr SEQ ID NO: 21 Mouse BMP4 cDNA Sequence
    1 atgattcctg gtaaccgaat gctgatggtc gttttattat gccaagtcct gctaggaggc
   61 gcgagccatg ctagtttgat acctgagacc gggaagaaaa aagtcgccga gattcagggc
  121 cacgcgggag gacgccgctc agggcagagc catgagctcc tgcgggactt cgaggcgaca
  181 cttctacaga tgtttgggct gcgccgcgct ccgcagccta gcaagagcgc cgtcattccg
  241 gattacatga gggatcttta ccggctccag tctggggagg aggaggagga agagcgagc
  301 cagggaaccg gcttgagta cccggagcgt ccgccagcc  gagccaacac tgtgaggagt
  361 ttccatcacg aagaacatct ggagaacatc ccagggacca gtgagagctc tgcttttcgt
  421 ttcctcttca acctcagcag catcccagag aatgaggtga tctcctcggc agagctccgg
  481 ctctttcggg agcaggtgga ccagggcct  gactgggaac agggcttcca ccgtataaac
  541 atttatgagg ttatgaagcc cccagcagaa atggttcctg gacacctcat cacacgacta
  601 ctggacacca gactagtcca tcacaatgtg acacggtggg aaactttcga tgtgagccct
  661 gcagtccttc gctggacccg ggaaaagcaa cccaattatg gctggccat  tgaggtgact
  721 cacctccacc agacacggac ccaccagggc cagcacgtca gaatcagccg atcgttacct
  781 caagggagtg gaaattgggc ccaactccgg cccctcctag tcactttgg  ccatgatagc
  841 cggggccata ccttgaccca cagaaaggcc aaacgtagtc ccaaacatca cccacagcgg
  901 tccaggaaga agaataagaa ctgccatcgc cattcactat acgtagactt cagtgacatg
  961 ggctggaatg attggattgt ggccccaccc gactaccaag ccttctactg ccacgggaac
 1021 tgtcccttc  cactggctga tcacctcaac tcaaccaacc atgccattgt gcagaccta
 1081 gtcaactctg ttaattctag tatccctaag gcctgttgtg tccccactga actgagtgcc
 1141 atttccatgt tgtacctgga tgagtatgac aaggtggtgt tgaaaaatta tcaggagatg
 1201 gtggtagagg ggtgtggatg ccgctga SEQ ID NO: 22 Mouse BMP4 Amino Acid Sequence
    1 mipgnrmlmv vllcqvllgg ashaslipet gkkkvaeiqg haggrrsgqs hellrdfeat
   61 llqmfglrrr pgpsksavip dymrdlyrlq sgeeeeeqs  qgtgleyper pasrantvrs
  121 fhheehleni pgtsessafr flfnlssipe nevissaelr lfreqvdqgp dweqgfhrin
  181 iyevmkppae mvpghlitrl ldtrlvhhnv trwetfdvsp avlrwtrekq pnyglaievt
  241 hlhqtrthqg qhvrisrslp qgsgdwaqlr pllvtfhdg  rghtltrrra krspkhhpqr
  301 srkknkncrr hslyvdfsdv gwndwivapp gyqafychgd cpfpladhln stnhaivqtl
  361 vnsvnssipk accvptelsa ismlyldeyd kvvlknyqem vvegcgcr
```

*Included in Table 1 are nucleic acid molecules comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a nucleic acid sequence of any SEQ ID NO listed in Table 1, or a portion thereof. Such nucleic acid molecules can encode a polypeptide having a function of the full-length polypeptide as described further herein.
*Included in Table 1 are polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

For the sake of reference and excluded from Table 1, the following human PD-L2 cDNA and amino acid sequences are provided.

```
SEQ ID NO: 23 Human PD-L2 cDNA Acid Sequence
atg atc ttc ctc ctg cta atg ttg agc ctg gaa ttg cag ctt cac cag    48
Met Ile Phe Leu Leu Leu Met Leu Ser Leu Glu Leu Gln Leu His Gln
  1               5                  10                  15 ata gca gct tta ttc aca gtg aca gtc cct aag gaa ctg tac ata ata    96
Ile Ala Ala Leu Phe Thr Val Thr Val Pro Lys Glu Leu Tyr Ile Ile
                 20                  25                  30 gag cat ggc agc aat gtg acc ctg gaa tgc aac ttt gac act gga agt   144
Glu His Gly Ser Asn Val Thr Leu Glu Cys Asn Phe Asp Thr Gly Ser
         35                  40                  45 cat gtg aac ctt gga gca ata aca gcc agt ttg caa aag gtg gaa aat   192
His Val Asn Leu Gly Ala Ile Thr Ala Ser Leu Gln Lys Val Glu Asn
     50                  55                  60 gat aca tcc cca cac cgt gaa aga gcc act ttg ctg gag gag cag ctg   240
Asp Thr Ser Pro His Arg Glu Arg Ala Thr Leu Leu Glu Glu Gln Leu
 65                  70                  75                  80
```

```
ccc cta ggg aag gcc tcg ttc cac ata cct caa gtc caa gtg agg gac    288
Pro Leu Gly Lys Ala Ser Phe His Ile Pro Gln Val Gln Val Arg Asp
            85                  90                  95 gaa gga cag tac caa tgc ata atc atc tat ggg gtc gcc tgg gac tac    336
Glu Gly Gln Tyr Gln Cys Ile Ile Ile Tyr Gly Val Ala Trp Asp Tyr
                100                 105                 110 aag tac ctg act ctg aaa gtc aaa gct tcc tac agg aaa ata aac act    384
Lys Tyr Leu Thr Leu Lys Val Lys Ala Ser Tyr Arg Lys Ile Asn Thr
            115                 120                 125 cac atc cta aag gtt cca gaa aca gat gag gta gag ctc acc tgc cag    432
His Ile Leu Lys Val Pro Glu Thr Asp Glu Val Glu Leu Thr Cys Gln
        130                 135                 140 gct aca ggt tat cct ctg gca gaa gta tcc tgg cca aac gtc agc gtt    480
Ala Thr Gly Tyr Pro Leu Ala Glu Val Ser Trp Pro Asn Val Ser Val
145                 150                 155                 160 cct gcc aac acc agc cac tcc agg acc cct gaa ggc ctc tac cag gtc    528
Pro Ala Asn Thr Ser His Ser Arg Thr Pro Glu Gly Leu Tyr Gln Val
                165                 170                 175 acc agt gtt ctg cgc cta aag cca ccc cct ggc aga aac ttc agc tgt    576
Thr Ser Val Leu Arg Leu Lys Pro Pro Pro Gly Arg Asn Phe Ser Cys
            180                 185                 190 gtg ttc tgg aat act cac gtg agg gaa ctt act ttg gcc agc att gac    624
Val Phe Trp Asn Thr His Val Arg Glu Leu Thr Leu Ala Ser Ile Asp
            195                 200                 205 ctt caa agt cag atg gaa ccc agg acc cat cca act tgg ctg ctt cac    672
Leu Gln Ser Gln Met Glu Pro Arg Thr His Pro Thr Trp Leu Leu His
        210                 215                 220 att ttc atc ccc tcc tgc atc att gct ttc att ttc ata gcc aca gtg    720
Ile Phe Ile Pro Ser Cys Ile Ile Ala Phe Ile Phe Ile Ala Thr Val
225                 230                 235                 240 ata gcc cta aga aaa caa ctc tgt caa aag ctg tat tct tca aaa gac    768
Ile Ala Leu Arg Lys Gln Leu Cys Gln Lys Leu Tyr Ser Ser Lys Asp
                245                 250                 255 aca aca aaa aga cct gtc acc aca aca aag agg gaa gtg aac agt gct    816
Thr Thr Lys Arg Pro Val Thr Thr Thr Lys Arg Glu Val Asn Ser Ala
            260                 265                 270 atc                                                                819
Ile

SEQ ID NO: 24 Human PD-L2 Amino Acid Sequence
Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160
```

-continued

```
Pro Ala Asn Thr Ser His Ser Arg Thr Pro Glu Glu Leu Try Gln Val
                165             170             175
Thr Ser Val Leu Arg Leu Lys Pro Pro Pro Gly Arg Asn Phe Ser Cys
            180             185             190
Val Phe Trp Asn Thr His Val Arg Glu Leu Thr Leu Ala Ser Ile Asp
        195             200             205
Leu Gln Ser Gln Met Glu Pro Arg Thr His Pro Thr Trp Leu Leu His
    210             215             220
Ile Phe Ile Pro Ser Cys Ile Ile Ala Phe Ile Phe Ile Ala Thr Val
225             230             235             240
Ile Ala Leu Arg Lys Gln Leu Cys Gln Lys Leu Tyr Ser Ser Lys Asp
            245             250             255
Thr Thr Lys Arg Pro Val Thr Thr Thr Lys Arg Glu Val Asn Ser Ala
        260             265             270
Ile
```

II. Agents that Modulate Respiratory Inflammation

It is demonstrated herein that the RGMb-NEO1-BMP signaling pathway regulates respiratory inflammation. Thus, the agents of the present invention described herein that modulate the interaction between members of the signaling pathway, whether directly or indirectly, can modulate respiratory inflammation to thereby treat respiratory inflammation disorders.

The interaction between RGMb, NEO1, and BMP (e.g., BMP2/BMP4) proteins results in the delivery of signals that promote respiratory inflammation. Thus, in one embodiment, agents which directly block one or more interactions between such proteins (e.g., anti-RGMb blocking antibodies) can prevent or inhibit respiratory inflammation. Exemplary agents include antibodies against RGMb. NEO1, and BMP (e.g., BMP2/BMP4); a non-activating form of RGMb, NEO1, and BMP (e.g., BMP2/BMP4) (e.g., a dominant negative polypeptide), small molecules or peptides that block the interaction between RGMb, NEO1, and/or BMP (e.g., BMP2/BMP4); fusion proteins (e.g. the extracellular portion of RGMb or NEO1 fused to the Fc portion of an antibody or immunoglobulin) that bind to and sequester components of the signaling pathway; nucleic acid molecules that block transcription or translation or RGMb, NEO1, and BMP (e.g., BMP2/BMP4); a non-activating form of a natural ligand of RGMb, NEO1, and BMP (e.g., BMP2/BMP4) or fusion protein thereof. Natural BMP2 and BMP4 ligands include, for example, chordin and noggin.

Additional agents useful in the methods of the present invention include antibodies, small molecules, peptides, peptidomimetics, natural ligands, and derivatives of natural ligands, that can either bind and/or activate or inhibit protein biomarkers of the invention, including the biomarkers listed in Table 1, or fragments thereof; RNA interference, antisense, nucleic acid aptamers. etc. that can downregulate the expression and/or activity of the biomarkers of the invention, including the biomarkers listed in Table 1, or fragments thereof.

In one embodiment, isolated nucleic acid molecules that specifically hybridize with or encode one or more biomarkers listed in Table 1 or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecules corresponding to the one or more biomarkers listed in Table 1 can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a lymphoma cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence of one or more biomarkers listed in Table 1 or a portion thereof (i.e., 100, 200, 300, 400, 450, 500, or more nucleotides), can be isolated using standard molecular biology techniques and the sequence information provided herein. For example, a human cDNA can be isolated from a human cell line (from Stratagene, LaJolla, Calif., or Clontech, Palo Alto, Calif.) using all or portion of the nucleic acid molecule, or fragment thereof, as a hybridization probe and standard hybridization techniques (i.e., as described in Sambrook, J., Fritsh, E. F., and Maniatis, T. *Molecular Cloning: A Laboratory Manual.* 2nd, ed., Cold Spring Harbor Laboratory. Cold Spring Harbor Laboratory Press, Cold Spring Harbor, N.Y., 1989). Moreover, a nucleic acid molecule encompassing all or a portion of the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence, or fragment thereof, can be isolated by the polymerase chain reaction using oligonucleotide primers designed based upon the sequence of the one or more biomarkers listed in Table 1, or fragment thereof, or the homologous nucleotide sequence. For example, mRNA can be isolated from respiratory system cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed according to well known methods in the art. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to the nucleotide sequence of one or more biomarkers listed in Table 1 can be prepared by standard synthetic techniques, i.e., using an automated DNA synthesizer.

Probes based on the nucleotide sequences of one or more biomarkers listed in Table 1 can be used to detect or confirm the desired transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express one or more biomarkers listed in Table 1, such as by measuring a level of one or more biomarkers nucleic acid in a sample of cells from a subject, i.e., detecting mRNA levels of one or more biomarkers listed in Table 1.

Nucleic acid molecules encoding proteins corresponding to one or more biomarkers listed in Table 1 from different species are also contemplated. For example, rat or monkey cDNA can be identified based on the nucleotide sequence of a human and/or mouse sequence and such sequences are well known in the art. In one embodiment, the nucleic acid molecule(s) of the invention encodes a protein or portion thereof which includes an amino acid sequence which is sufficiently homologous to an amino acid sequence of one or more biomarkers listed in Table 1, such that the protein or portion thereof modulates (e.g., enhance), one or more of the following biological activities: a) binding to the biomarker; b) modulating the copy number of the biomarker; c) modulating the expression level of the biomarker; and d) modulating the activity level of the biomarker.

As used herein, the language "sufficiently homologous" refers to proteins or portions thereof which have amino acid sequences which include a minimum number of identical or equivalent (e.g., an amino acid residue which has a similar side chain as an amino acid residue in one or more biomarkers listed in Table 1, or fragment thereof) amino acid residues to an amino acid sequence of the biomarker, or fragment thereof, such that the protein or portion thereof modulates (e.g., enhance) one or more of the following biological activities: a) binding to the biomarker; b) modulating the copy number of the biomarker; c) modulating the expression level of the biomarker; and d) modulating the activity level of the biomarker.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of the biomarker, or a fragment thereof.

Portions of proteins encoded by nucleic acid molecules of the one or more biomarkers listed in Table 1 are preferably biologically active portions of the protein. As used herein, the term "biologically active portion" of one or more biomarkers listed in Table 1 is intended to include a portion, e.g., a domain/motif, that has one or more of the biological activities of the full-length protein.

Standard binding assays, e.g., immunoprecipitations and yeast two-hybrid assays, as described herein, or functional assays, e.g., RNAi or overexpression experiments, can be performed to determine the ability of the protein or a biologically active fragment thereof to maintain a biological activity of the full-length protein.

The invention further encompasses nucleic acid molecules that differ from the nucleotide sequence of the one or more biomarkers listed in Table 1, or fragment thereof due to degeneracy of the genetic code and thus encode the same protein as that encoded by the nucleotide sequence, or fragment thereof. In another embodiment, an isolated nucleic acid molecule of the invention has a nucleotide sequence encoding a protein having an amino acid sequence of one or more biomarkers listed in Table 1, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of the one or more biomarkers listed in Table 1, or fragment thereof. In another embodiment, a nucleic acid encoding a polypeptide consists of nucleic acid sequence encoding a portion of a full-length fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of the one or more biomarkers listed in Table 1 may exist within a population (e.g., a mammalian and/or human population). Such genetic polymorphisms may exist among individuals within a population due to natural allelic variation. As used herein, the terms "gene" and "recombinant gene" refer to nucleic acid molecules comprising an open reading frame encoding one or more biomarkers listed in Table 1, preferably a mammalian, e.g., human, protein. Such natural allelic variations can typically result in 1-5% variance in the nucleotide sequence of the one or more biomarkers listed in Table 1. Any and all such nucleotide variations and resulting amino acid polymorphisms in the one or more biomarkers listed in Table 1 that are the result of natural allelic variation and that do not alter the functional activity of the one or more biomarkers listed in Table 1 are intended to be within the scope of the invention. Moreover, nucleic acid molecules encoding one or more biomarkers listed in Table 1 proteins from other species.

In addition to naturally-occurring allelic variants of the one or more biomarkers listed in Table 1 sequence that may exist in the population, the skilled artisan will further appreciate that changes can be introduced by mutation into the nucleotide sequence, or fragment thereof, thereby leading to changes in the amino acid sequence of the encoded one or more biomarkers listed in Table 1, without altering the functional ability of the one or more biomarkers listed in Table 1. For example, nucleotide substitutions leading to amino acid substitutions at "non-essential" amino acid residues can be made in the sequence, or fragment thereof. A "non-essential" amino acid residue is a residue that can be altered from the wild-type sequence of the one or more biomarkers listed in Table 1 without altering the activity of the one or more biomarkers listed in Table 1, whereas an "essential" amino acid residue is required for the activity of the one or more biomarkers listed in Table 1. Other amino acid residues, however, (e.g., those that are not conserved or only semi-conserved between mouse and human) may not be essential for activity and thus are likely to be amenable to alteration without altering the activity of the one or more biomarkers listed in Table 1.

The term "sequence identity or homology" refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions". e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (J. Mol. Biol. (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a protein homologous to one or more biomarkers listed in Table 1, or fragment thereof, can be created by introducing one or more nucleotide substitutions, additions or deletions into the nucleotide sequence, or fragment thereof, or a homologous nucleotide sequence such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in one or more biomarkers listed in Table 1 is preferably replaced with another amino acid residue from the same side chain family. Alternatively, in another embodiment, mutations can be introduced randomly along all or part of the coding sequence of the one or more biomarkers listed in Table 1, such as by saturation mutagenesis, and the resultant mutants can be screened for an activity described herein to identify mutants that retain desired activity. Following mutagenesis, the encoded protein can be expressed recombinantly according to well known methods in the art and the activity of the protein can be determined using, for example, assays described herein.

The levels of one or more biomarkers listed in Table 1 levels may be assessed by any of a wide variety of well known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, the levels of one or more biomarkers listed in Table 1 levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see. e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding One or more biomarkers listed in Table 1. Other suitable probes for use in the diagnostic assays of the invention are described herein. Hybridization of an mRNA with the probe indicates that One or more biomarkers listed in Table 1 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the One or more biomarkers listed in Table 1 mRNA expression levels.

An alternative method for determining mRNA expression level in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA.* 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the One or more biomarkers listed in Table 1 mRNA.

As an alternative to making determinations based on the absolute expression level, determinations may be based on the normalized expression level of one or more biomarkers listed in Table 1. Expression levels are normalized by correcting the absolute expression level by comparing its expression to the expression of a non-biomarker gene, e.g., a housekeeping gene that is constitutively expressed. Suitable genes for normalization include housekeeping genes such as the actin gene, or epithelial cell-specific genes. This normalization allows the comparison of the expression level in one sample. e.g., a subject sample, to another sample, e.g., a normal sample, or between samples from different sources.

The level or activity of a protein corresponding to one or more biomarkers listed in Table 1 can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express the biomarker of interest.

The present invention further provides soluble, purified and/or isolated polypeptide forms of one or more biomarkers listed in Table 1, or fragments thereof. In addition, it is to be understood that any and all attributes of the polypeptides described herein, such as percentage identities, polypeptide lengths, polypeptide fragments, biological activities, antibodies, etc. can be combined in any order or combination with respect to any biomarker listed in Table 1 and combinations thereof.

In one aspect, a polypeptide may comprise a full-length amino acid sequence corresponding to one or more biomarkers listed in Table 1 or a full-length amino acid sequence with 1 to about 20 conservative amino acid substitutions. An amino acid sequence of any described herein can also be at least 50, 55, 60, 65, 70, 75, 80, 85, 90, 91, 92, 93, 94, 95, 96, 97, 98, 99, or 99.5% identical to the full-length sequence of one or more biomarkers listed in Table 1, which is either described herein, well known in the art, or a fragment thereof. In another aspect, the present invention contemplates a composition comprising an isolated polypeptide corresponding to one or more biomarkers listed in Table 1 polypeptide and less than about 25%, or alternatively 15%, or alternatively 5%, contaminating biological macromolecules or polypeptides.

The present invention further provides compositions related to producing, detecting, or characterizing such polypeptides, or fragment thereof, such as nucleic acids, vectors, host cells, and the like. Such compositions may serve as compounds that modulate the expression and/or activity of one or more biomarkers listed in Table 1.

An isolated polypeptide or a fragment thereof (or a nucleic acid encoding such a polypeptide) corresponding to one or more biomarkers of the invention, including the biomarkers listed in Table 1 or fragments thereof, can be used as an immunogen to generate antibodies that bind to said immunogen, using standard techniques for polyclonal and monoclonal antibody preparation according to well known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In one embodiment, useful antibodies include 1) anti-RGMb antibodies that block the interaction between a BMP and RGMb without blocking the interaction between PD-L2 and RGMb, 2) anti-RGMb antibodies that block the interaction between NEO1 and RGMb without blocking the interaction between PD-L2 and RGMb, 3) anti-RGMb antibodies that block both the BMP/RGMb interaction and NEO1/RGMb interaction and without blocking the interaction between PD-L2 and RGMb, 4) anti-RGMb antibodies that block the interaction between a BMP and RGMb and block the interaction between PD-L2 and RGMb, 5) anti-RGMb antibodies that block the interaction between NEO1 and RGMb and block the interaction between PD-L2 and RGMb, and 6) anti-RGMb antibodies that block both the BMP/RGMb interaction and NEO1/RGMb interaction and further block the interaction between PD-L2 and RGMb.

For example, a polypeptide immunogen typically is used to prepare antibodies by immunizing a suitable subject (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well known protocols used for fusing lymphocytes and immortalized cell lines can be applied for the purpose of generating a monoclonal antibody against one or more biomarkers of the invention, including the biomarkers listed in Table 1, or a fragment thereof (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.*

19:4133-4137; Barbas et al. (1991) *Proc. Natl. Acad. Sci. USA* 88:7978-7982; and McCafferty et al. (1990) *Nature* 348:552-554.

Since it is well known in the art that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of the present invention (e.g., including the sequences of Table 3, or portions thereof). The antibodies further can comprise the CDR2s of variable regions of the present invention (e.g., including the sequences of Table 3, or portions thereof). The antibodies further can comprise the CDR1s of variable regions of the present invention (e.g., including the sequences of Table 3, or portions thereof). In other embodiments, the antibodies can comprise any combinations of the CDRs.

The CDR1, 2, and/or 3 regions of the engineered antibodies described above can comprise the exact amino acid sequence(s) as those of variable regions of the present invention (e.g., including the sequences of Table 3, or portions thereof) disclosed herein. However, the ordinarily skilled artisan will appreciate that some deviation from the exact CDR sequences may be possible while still retaining the ability of the antibody to bind RGMb or PD-L2 effectively (e.g., conservative sequence modifications). Accordingly. in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention (e.g., including the sequences of Table 3, or portions thereof).

The structural features of non-human or human antibodies (e.g., a rat anti-mouse/anti-human RGMb antibody described herein) can be used to create structurally related human antibodies that retain at least one functional property of the antibodies of the present invention, such as binding to RGMb. Another functional property includes inhibiting binding of the original known, non-human or human antibodies in a competition ELISA assay.

Antibodies, immunoglobulins, and polypeptides of the invention can be use in an isolated (e.g., purified) form or contained in a vector, such as a membrane or lipid vesicle (e.g. a liposome).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the antibodies of the present invention, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr et al. (1987) and by Edge et al. (1981). Enzymatic cleavage of carbohydrate moieties on antibodies can be achieved by the use of a variety of endo- and exo-glycosidases as described by Thotakura et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated antibodies can be used diagnostically or prognostically to monitor polypeptide levels in tissue as part of a clinical testing procedure, e.g., to determine the efficacy of a given treatment regimen. Detection can be facilitated by coupling (ie., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}I$, $^{131}I$, $^{35}S$, or $^{3}H$. As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, Pseudomonas exotoxin, or diphtheria toxin; a protein such as tumor necrosis factor or interferon-.gamma.; or, biological response modifiers such as, for example, lymphokines, interleukin-1 ("IL-"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

In some embodiments, conjugations can be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

Additionally, recombinant polypeptide antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Lett.* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Biotechnology* (NY) 12:396-399; Chen, S-Y. et al. (1994) *Hum. Gene Ther.* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

Additionally, fully human antibodies could be made against biomarkers of the invention, including the biomarkers listed in Table 1, or fragments thereof. Fully human antibodies can be made in mice that are transgenic for human immunoglobulin genes, e.g. according to Hogan, et al., "Manipulating the Mouse Embryo: A Laboratory Manuel," Cold Spring Harbor Laboratory. Briefly, transgenic mice are immunized with purified immunogen. Spleen cells are harvested and fused to myeloma cells to produce hybridomas. Hybridomas are selected based on their ability to produce antibodies which bind to the immunogen. Fully human antibodies would reduce the immunogenicity of such antibodies in a human.

In one embodiment, an antibody for use in the instant invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more biomarkers listed in Table 1, or a fragment thereof. In one embodiment, the bispecific antibody could specifically bind to both a polypeptide or a fragment thereof and its natural binding partner(s) or a fragment(s) thereof.

In another aspect of this invention, peptides or peptide mimetics can be used to antagonize or agonize the activity of one or more biomarkers of the invention, including one or more biomarkers listed in Table 1, or a fragment(s) thereof. In one embodiment, variants of one or more biomarkers listed in Table 1 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) *Proc. Natl. Acad. Sci. USA* 89:7811-7815; Delagrave et al. (1993) *Protein Eng.* 6(3): 327-331). In one embodiment, cell based assays can be exploited to analyze a variegated polypeptide library. For example, a library of expression vectors can be transfected into a cell line which ordinarily synthesizes one or more biomarkers of the invention, including one or more biomarkers listed in Table 1, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 1: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Peptidomimetics (Fauchere, J. (1986) *Adv. Drug Res.* 15:29; Veber and Freidinger (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —CH2S—, —CH2-CH2-, —CH=CH— (cis and trans). —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I.* 307-314 (—CH—CH—, cis and trans); Almquist. R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. European Appln. EP 45665 (1982) CA: 97:39405 (1982)(—CH(OH) CH2-); Holladay, M. W. et al. (1983) *Tetrahedron Lett.* (1983) 24:4401-4404 (—C(OH)CH2-); and Hruby. V. J.

(1982) *Lie Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivitization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., between biomarkers listed in Table 1 and their natural binding partners. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991)*J. Mol. Biol.* 222:301-310); (Ladner supra.). Compounds can be screened in cell based or non-cell based assays. Compounds can be screened in pools (e.g. multiple compounds in each testing sample) or as individual compounds.

The invention also relates to chimeric or fusion proteins of the biomarkers of the invention, including the biomarkers listed in Table 1, or fragments thereof. As used herein, a "chimeric protein" or "fusion protein" comprises one or more biomarkers of the invention, including one or more biomarkers listed in Table 1, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers of the invention, including one or more biomarkers listed in Table 1, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ4 domain (e.g., the hinge, CH2 and CH3 regions of human IgCγ1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992).

Particularly preferred Ig fusion proteins include the extracellular domain portion or variable region-like domain of human RGMb, NEO1, BMP, or other biomarker listed in Table 1, coupled to an immunoglobulin constant region (e.g., the Fc region). The immunoglobulin constant region may contain genetic modifications which reduce or eliminate effector activity inherent in the immunoglobulin structure. For example, DNA encoding the extracellular portion of a polypeptide of interest can be joined to DNA encoding the hinge, CH2 and CH3 regions of human IgGγ1 and/or IgGγ4 modified by site directed mutagenesis, e.g., as taught in WO 97/28267.

In another embodiment, the fusion protein contains a heterologous signal sequence at its N-terminus. In certain host cells (e.g., mammalian host cells), expression and/or secretion of a polypeptide can be increased through use of a heterologous signal sequence.

The fusion proteins of the invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can enhance or upregulate one or more biological activities associated with the corresponding wild-type, naturally occurring, or synthetic small nucleic acids. In another embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the invention, including one or more biomarkers listed in Table 1, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin. In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296: 550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 1). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner, R. (1994) Nature 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. 84:648-652: PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) BioTechniques 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxyti-ethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl-aminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-0-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch. Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette. Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) Nature 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloffand Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g. antibodies, small molecules, peptides, fusion proteins, or small nucleic acids) can be incorporated into pharmaceutical compositions and administered to a subject in vivo. The compositions may contain a single such molecule or agent or any combination of agents described herein. "Single active agents" described herein can be combined with other pharmacologically active compounds ("second active agents") known in the art according to the methods and compositions provided herein. It is believed that certain combinations work synergistically in the treatment of conditions that would benefit from the mouldation of immune responses. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful in this invention include proteins that reduce inflammatory responses in vitro or in vivo.

III. Methods of Selecting Agents that Modulate Respiratory Inflammation

Another aspect of the invention relates to methods of selecting agents (e.g., antibodies, fusion proteins, peptides, or small molecules) which modulate respiratory inflammation. Such methods utilize screening assays, including cell based and non-cell based assays. In one embodiment, the assays provide a method for identifying agents that inhibit the interactions between RGMb, NEO1, and/or BMPs like BMP2 and/or BMP4 (e.g., with or without inhibiting the interaction of RGMb with PD-L2).

In one embodiment, the invention relates to assays for screening candidate or test compounds that bind to, or modulate the activity of, RGMb, NEO1, and/or BMPs like BMP2 and/or BMP4 (e.g., with or without inhibiting the interaction of RGMb with PD-L2). In one embodiment, a method for identifying an agent to modulate an immune response entails determining the ability of the agent to modulate. e.g. inhibit, the interaction between RGMb, NEO1, and/or BMPs like BMP2 and/or BMP4 (e.g., with or without inhibiting the interaction of RGMb with PD-L2), and further determining the ability of the agent to modulate one or more respiratory inflammatory disorder symptoms selected from the group consisting of AHR, recurrent wheezing, coughing, trouble breathing, chest tightness, symptoms that occur or worsen at night, symptoms that are triggered by cold air, exercise or exposure to allergens, upregulated serum IgE (atopy), eosinophilia, and excessive mucus secretion in a subject. Such agents include, without limitation, antibodies, proteins, fusion proteins, small molecules, and nucleic acids.

In one embodiment, an assay is a cell-based assay, comprising contacting comprising contacting a cell expressing RGMb protein with a NEO1, BMP2, and/or BMP4 protein, and a test compound, and determining the ability of the test compound to 1) modulate the binding between the RGMb protein and the NEO1, BMP2, and/or BMP4 protein and 2) modulate one or more respiratory inflammatory disorder symptoms selected from the group consisting of AHR, recurrent wheezing, coughing, trouble breathing, chest tightness, symptoms that occur or worsen at night, symptoms that are triggered by cold air, exercise or exposure to allergens, upregulated serum IgE (atopy), eosinophilia, and excessive mucus secretion in a subject, wherein a test compound that modulates the binding of the proteins and symptoms treats the respiratory inflammatory disorder. In another embodiment, the cell-based assay comprises contacting a cell expressing NEO1 with a RGMb. BMP2, and/or BMP4 protein, and a test compound, and a test compound and determining the ability of the test compound to 1) modulate the binding between the RGMb protein and the NEO1, BMP2, and/or BMP4 protein and 2) modulate one or more respiratory inflammatory disorder symptoms selected from the group consisting of AHR, recurrent wheezing, coughing, trouble breathing, chest tightness, symptoms that occur or worsen at night, symptoms that are triggered by cold air, exercise or exposure to allergens, upregulated serum IgE (atopy), eosinophilia, and excessive mucus secretion in a subject, wherein a test compound that modulates the binding of the proteins and symptoms treats the respiratory inflammatory disorder.

Determining the ability of the polypeptides to bind to, or interact with, each other can be accomplished, e.g., by measuring direct binding or by measuring a parameter of immune cell activation or inflammation. For example, in a direct binding assay, the polypeptides can be coupled with a radioisotope or enzymatic label such that binding of the polypeptides can be determined by detecting the labeled protein in a complex. For example, the polypeptides can be labeled with $^{125}$I, $^{35}$S, $^{14}$C, or $^{3}$H, either directly or indirectly, and the radioisotope detected by direct counting of radioemmission or by scintillation counting. Alternatively, the polypeptides can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between polypeptides, without the labeling of any of the interactants. For example, a microphysiometer can be used to detect the interaction of RGMb and PD-L2 without the labeling of either polypeptide (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the blocking agents (e.g. antibodies, fusion proteins, peptides, or small molecules) to antagonize the interaction between a given set of polypeptides can be accomplished by determining the activity of one or more members of the set of polypeptides. For example, the activity of RGMb or PD-L2 can be determined by detecting induction of a cellular second messenger (e.g., see signaling cascade of FIG. 1i), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by RGMB-NEO1-BMP signaling.

In yet another embodiment, an assay of the present invention is cell-free. For example, a cell-free method for screening for compounds which treat a respiratory inflammatory disorder by modulating RGMb-NEO1-BMP signaling comprising contacting a RGMb. NEO1, BMP2, and/or BMP4 protein with at least one of the protein's natural binding partners selected from the group consisting of RGMb, NEO1, BMP2, and/or BMP4 protein, and a test compound, and determining the ability of the test compound to 1) modulate the binding between the protein(s) and 2) modulate one or more respiratory inflammatory disorder symptoms selected from the group consisting of AHR, recurrent wheezing, coughing, trouble breathing, chest tightness, symptoms that occur or worsen at night, symptoms that are triggered by cold air, exercise or exposure to allergens, upregulated serum IgE (atopy), eosinophilia, and excessive mucus secretion in a subject, wherein a test compound that modulates the binding between the protein(s) and symptoms treats the respiratory inflammatory disorder is provided.

Binding of the test compound can be determined either directly or indirectly as described above. In a preferred embodiment, the assay includes contacting the polypeptide, or biologically active portion thereof, with its binding partner to form an assay mixture, contacting the assay mixture with a test compound, and determining the ability of the test compound to interact with the polypeptide in the assay mixture, wherein determining the ability of the test compound to interact with the polypeptide comprises determining the ability of the test compound to preferentially bind to the polypeptide or biologically active portion thereof, as compared to the binding partner.

In some embodiments, whether for cell-based or cell-free assays, the test compound can further be assayed to determine whether it affects binding and/or activity of other polyppetide interactions of interest, such as that between RGMb and PD-L2. Other useful binding analysis methods include the use of real-time Biomolecular Interaction Analysis (BIA) (Sjolander, S. and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. Polypeptides of interest can be immobilized on a BIAcore chip and multiple agents (blocking antibodies, fusion proteins, peptides, or small molecules) can be tested for binding to the polypeptide of interest. An example of using the BIA technology is described by Fitz et al. (1997) *Oncogene* 15:613.

The cell-free assays of the present invention are amenable to use of both soluble and/or membrane-bound forms of proteins. In the case of cell-free assays in which a membrane-bound form protein is used (e.g., a cell surface RGMb or NEO1) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide. Triton® X-100, Triton® X-114. Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either polypeptides to facilitate separation of complexed from uncomplexed forms of one or both of the proteins, as well as to accommodate automation of the assay. Binding of a test compound to a polypeptide, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/RGMb polypeptide fusion proteins, or glutathione-S-transferase/target fusion proteins, can be adsorbed onto glutathione sepharose beads (Sigma Chemical, St. Louis, Mo.) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of polypeptide binding or activity determined using standard techniques.

This invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

IV. Pharmaceutical Compositions

A agents that modulate the interaction between RGMb, NEO1, and BMP (e.g., BMP2 and/or BMP4), with or without blocking the interaction between RGMb and PD-L2, including, e.g., blocking antibodies, peptides, fusion proteins, or small molecules, can be incorporated into pharmaceutical compositions suitable for administration to a subject. Such compositions typically comprise the antibody, peptide, fusion protein or small molecule and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by, and directly dependent on, the unique characteristics of the active compound, the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The above described modulating agents may be administered it he form of expressible nucleic acids which encode said agents. Such nucleic acids and compositions in which they are contained, are also encompassed by the present invention. For instance, the nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The modulatory agents described herein can be used according to a number of methods related to the modulation of the interaction between RGMb, NEO1, and BMP (e.g., BMP2 and/or BMP4), with or without blocking the interaction between RGMb and PD-L2. Diagnostic uses have been described above.

1. Prophylactic Methods

In one aspect, the present invention provides a method for preventing in a subject, a disease or condition associated with an unwanted or less than desirable immune response. Subjects at risk for a disease that would benefit from treatment with the claimed agents or methods can be identified, for example, by any or a combination of diagnostic or prognostic assays known in the art. Administration of a prophylactic agent can occur prior to the manifestation of symptoms associated with an unwanted or less than desirable immune response. The appropriate agent used for treatment (e.g. antibodies, peptides, fusion proteins or small molecules) can be determined based on clinical indications and can be identified, e.g., using screening assays described herein.

2. Therapeutic Methods

Another aspect of the invention pertains to therapeutic methods of modulating an immune response, e.g., by modulating the interaction between RGMb, NEO1, and BMP (e.g., BMP2 and/or BMP4), with or without blocking the interaction between RGMb and PD-L2.

Modulatory methods of the present invention involve contacting a cell with an agent that modulates the interaction between RGMb, NEO1, and BMP (e.g., BMP2 and/or BMP4), with or without blocking the interaction between RGMb and PD-L2. Exemplary agents have been described above. For example, an agent that modulates the activity or interaction between RGMb, NEO1, and BMP (e.g., BMP2 and/or BMP4), with or without blocking the interaction between RGMb and PD-L2 includes a nucleic acid or a protein molecule, a naturally-occurring target molecule of the polypeptides (e.g., PD-L2, BMP-2, BMP-4. BMP receptors), blocking antibodies, antagonist (e.g., antisense nucleic acid molecule, triplex oligonucleotide, and ribozymes), peptidomimetics of such antagonists, nucleic acid antagonists of the nucleic acid or protein expression or activity, or other small molecules. Administration with combinations of other useful immunomodulatory agents, such as anti-IL25 and/or anti-IL17RB inhibitors (e.g., blocking antibodies), are also contemplated.

In a preferred embodiment, an agent that modulates the expression of RGMb, NEO1, and BMP (e.g., BMP2 and/or BMP4) is, e.g., an antisense nucleic acid molecule, triplex oligonucleotide, a ribozyme, or a recombinant vector for expression of a RGMb or PD-L2 protein.

These modulatory agents can be administered in vitro (e.g., by contacting the cell with the agent) or, alternatively, in vivo (e.g., by administering the agent to a subject). As such, the present invention relates to methods of treating an individual afflicted with a disease or disorder that would benefit from modulation of an immune response, e.g., by modulation of the interaction between RGMb and PD-L2.

VI. Administration of Agents

The immune modulating agents of the invention are administered to subjects in a biologically compatible form suitable for pharmaceutical administration in vivo, to either enhance or suppress immune cell mediated immune responses. By "biologically compatible form suitable for administration in vivo" is meant a form of the protein to be administered in which any toxic effects are outweighed by the therapeutic effects of the protein. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of an agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The agents or the invention described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an agent of the invention (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form", as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by, and directly dependent on, (a) the unique characteristics of the active compound and the particular therapeutic effect to be achieved, and (b) the limitations inherent in the art of compounding such an active compound for the treatment of sensitivity in individuals.

In one embodiment, an agent of the invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

VII. Kits

The present invention also provides kits. The kit may comprise reagents for assessing and/or modulating expression of RGMb, NEO1, and/or BMP (e.g., BMP2 and/or BMP4) at the nucleotide and/or protein level. In one embodiment, the reagents may be an antibody or fragment thereof, wherein the antibody or fragment thereof specifically binds to a polypeptide of interest. Optionally, the kits may comprise a polynucleotide agent or probe that specifically binds to a transcribed polynucleotide corresponding to the desired biomarker. The kit may contain means for determining the amount of biomarker protein or mRNA in a sample and means for comparing the amount of the protein or mRNA in the sample with a control or standard. The compound or agent can be packaged in a suitable container. The kit can further comprise instructions for using the agents.

This invention is further illustrated by the following examples which should not be construed as limiting. The contents of all references, patents and published patent applications cited throughout this application, as well as the Figures, are incorporated herein by reference.

EXAMPLES

Example 1: Materials and Methods for Examples 2-10

A. Animals

Wild type (WT) BALB/cBy and C57BL/6 mice were purchased from the Jackson Laboratory (Bar Harbor, Me.). PD-L2$^{-/-}$ knockout mice on BALB/c background have been described (Keir et al. (2008) *Annu. Rev. Immunol.* 26:677-704). Mice were maintained and used according to institutional and National Institutes of Health guidelines in a pathogen-free facility. IL-17RB−/− mice were provided by A. L. Budelsky. The Animal Care and Use Committee at Boston Children's Hospital approved all animal protocols.

B. Antibodies

RGMb antibodies used were previously generated as described in PCT Appl. No. PCT/US13/53393. Briefly, rats were immunized 3 times via intramuscular and intravenous injection of mRGMb plasmid cDNA (Latchman et al. (2001) *Nat. Immunol.* 2:261-268), and boosted 3 times with recombinant mRGMb-HIS (R&D) via i.p. and s.c. injection. Hybridoma supernatants were screened by flow cytometry on mRGMb transfected 300 cells or ELISA on plates coated with recombinant mRGMb (R&D). Hybridomas were subcloned to stability and antibodies were purified from culture supernatants by protein G affinity chromatography, and verified to have endotoxin levels less than 2 EU/mg protein. In addition, Table 2 provides a summary of the blocking capacities of various mRGMb and mPD-L2 monoclonal antibodies. For example, clone 9D1 blocks the interaction of RGMb with BMP-2/4 and with PD-L2, and partially blocks the interaction of RGMb with neogenin. PD-L2 mAb 2C9 blocks the interaction of PD-L2 with RGMb, but does not block the interaction of PD-L2 with PD-1 (Xiao et al. (2014) *J. Exp. Med.* 211:943-959).

TABLE 2

Blocking capacities of mRGMb and mPD-L2 mAbs

| Blocking | mRGMb to mPD-L2 | mPD-L2 to mPD-1 | mRGMb to mBMP-2/4 | mRGMb to mNeogenin |
|---|---|---|---|---|
| mRGMb mAbs | | | | |
| 307.9D1, 307.8B2 | Yes | N.A. | Yes | Weak |
| 307.1H6, 307.9D3, 307.5G1 | No | N.A. | No | Weak |
| mPD.L2 mAbs | | | | |
| GF17.2C9 | Yes | No | N.A. | N.A. |
| 3.2, TY2S, MIH37 | Yes | Yes | N.A. | N.A. |

N.A.: Not applicable

The antibody specificities were determined as described in PCT Appl. No. PCT/US13/53393. Briefly, cells were stained with target antibodies and isotype controls using standard flow cytometry procedures, and analyzed on a FACSCanto (BD Biosciences) and FlowJo 9.2 software (TreeStar).

The mouse 300.19 pre-B cell line was transfected by electroporation with mRGMb, hRGMb, mNeogenin, hNeogenin, or mIL-17RB cDNA in the pEF-Puro expression vector. Cells were selected in media containing puromycin, sorted, and subcloned. Cell-surface expression of mRGMb, hRGMb or mNeogenin was verified by flow cytometry using an mRGMb polyclonal antibody (R&D), an hRGMb mAb (R&D) or mRGMb-Ig, respectively. Other transfected cells, such as 300-mPD-L2, 300-mPD-L1, 300-mPD-1, and Jurkat-hPD-1, have been made previously using similar methods. Cells were cultured in RPMI-1640 (Mediatech) supplemented with 10% heat-inactivated FBS (Invitrogen), 1% streptomycin/penicillin, 15 µg/ml gentamicin (Invitrogen), 1% glutamax (Invitrogen), and 50 µM β-mercaptoethanol (Sigma-Aldrich) at 37° C. with 5% CO₂. The cell lines used in this study were purchased from American Type Culture Collection (ATC).

In addition, various Ig fusion proteins were made as described in PCT Appl. No. PCT/US13/53393. mRGMb-Ig fusion proteins were generated by joining the extracellular domain of mRGMb to the Fc portion of mouse IgG2a protein, mutated to reduce FcR binding (Latchman et al. (2001) *Nat. Immunol.* 2:261-268). mPD-L2-hIgG/IgA fusion proteins were generated by joining the extracellular domain of PD-L2 with the Fc portion of hIgG1 and the tail piece of hIgA (Hirano et al. (2006) *Blood* 107:1528-1536). Fc fusion proteins were purified from CHO cell culture supernatants by protein A or protein G affinity chromatography and verified to have endotoxin levels less than 2 EU/mg protein. Other Ig fusion proteins used have been described previously (Latchman et al. (2001) *Nat. Immunol.* 2:261-268).

To initially verify RGMb expression on mRGMb or hRGMb transfected cells, sheep anti-mRGMb (R&D) or sheep IgG (SouthernBiotech) plus donkey anti-sheep IgG-PE (Jackson ImmunoResearch Laboratories) and mouse anti-hRGMb (mAb. R&D) plus goat anti-mouse IgG-PE (SouthernBiotech) were used, respectively, all at 10 µg/ml.

To test the binding specificities of mRGMb antibodies, mRGMb or hRGMb transfected 300 cells were incubated with serial dilutions of sera, culture supernatants or purified antibodies, then binding was detected with 5 µg/ml of goat anti-rat IgG-PE (SouthernBiotech). For biotin-conjugated mRGMb mAb 9D1, 1.4 µg/ml of streptavidin-PE was used.

For receptor-ligand binding assay, mRGMb, hRGMb, or mNeogenin transfected 300 cells and control cells (300 cells and hPD-1 transfected Jurkat T cells) were stained with serial dilutions of mPD-L2-hIgG1/IgA or control-hIgG1/IgA plus 5 µg/ml of Fab2 goat anti-hIgG-PE (mouse-absorbed. SouthernBiotech), or with serial dilutions of mPD-L1-mIgG2a or control-mIgG2a plus 10 µg/ml of goat anti-mIgG2a-PE (SouthernBiotech). mPD-L2 transfected 300 cells and 300 cells were stained with serial dilutions of mRGMb-mIgG2a or control-mIgG2a plus 5 µg/ml of Fab2 goat anti-mIgG2a-PE (SouthernBiotech).

To test the capacities of RGMb mAbs to block mRGMb binding to mNeogenin, RGMb-mIgG2a at 5 µg/ml was incubated with serial dilutions of RGMb mAbs, then added to neogenin transfected 300 cells. Binding was detected using 10 g/ml of goat anti-mIgG2a-PE (SouthernBiotech). To determine the background binding, 300-neogenin cells were stained with serial dilutions of mIgG2a isotype control.

In addition, ELISA techniques were also used as described in PCT Appl. No. PCT/US13/53393.

Briefly, to examine specificity of mRGMb mAbs, 96-well plates were coated with 2 µg/ml of recombinant mRGMa-HIS, mRGMb-HIS, or mRGMc-HIS (R&D). Then, serial dilutions of mRGMb mAbs and isotype controls were added and incubated for 1 hour (h) at 37° C. Mouse anti-rat IgG (γ-specific)-HRP (Jackson ImmunoResearch Laboratories) at 1:2500 was used for detection.

To examine RGMa/RGMb/RGMc and PD-L2 interaction, 96-well ELISA plates were coated with 2 or 5 µg/ml of recombinant mRGMa-HIS, mRGMb-HIS, mRGMc-HIS, or hRGMb-HIS (R&D). Then, serial dilutions of mPD-L2-hIgG1/IgA, mPD-L2-mIgG2a/IgA, hPD-L2-mIgG2a or control-Ig fusion proteins were added and incubated for 1 h at 37° C. Fab₂ goat anti-hIgG-HRP (Jackson ImmunoResearch Laboratories) or rat anti-mIgG2a-HRP (BD Biosciences) at 1:1000 or 1:10000 were used for detection.

To test the capacities of mRGMb antibodies and mPD-L2 fusion proteins to block RGMb binding to BMP-2/4, 96-well ELISA plates were coated with 1 g/ml of recombinant mouse BMP-2 (GIBCO) or BMP-4 (R&D). mRGMb antibodies, isotype controls, mPD-L2-hIgG1/IgA, mPD-L2-mIgG2a/IgA, or control Ig fusion proteins at the indicated concentrations were preincubated with 20 µg/ml mRGMb- HIS (R&D) for 45 min. at 4° C., then added to the plates and incubated for 1 h at 37° C. Anti-penta-HIS-HRP (Qiagen) at 1:1000 was used for detection.

To determine if RGMb binds PD-L2 and BMP-2/4 simultaneously, 96-well ELISA plates were coated with BMP-2/4 as above. mPD-L2-hIgG1/IgA, mPD-L2-hIgG (R&D), mPD-L1-hIgG (R&D) or control-Ig fusion proteins at 10 g/ml were preincubated with 10 μg/ml mRGMb-HIS (R&D) or buffer alone for 15 min. at room temperature (RT), then added to the plates and incubated for 1 h at 37° C. Alternatively, 10 μg/ml mRGMb-HIS (R&D) or buffer alone was added first to the plates and incubated for 1 h at 37° C. After wash, mPD-L2-Ig or control-Ig fusion proteins were added and incubated for 1 h at 37° C. Fab₂ goat anti-hIgG-HRP (Jackson ImmunoResearch Laboratories) at 1:10000 was used for detection.

The substrate for HRP was TMB microwell peroxidase substrate system (KPL).

Figure 2:
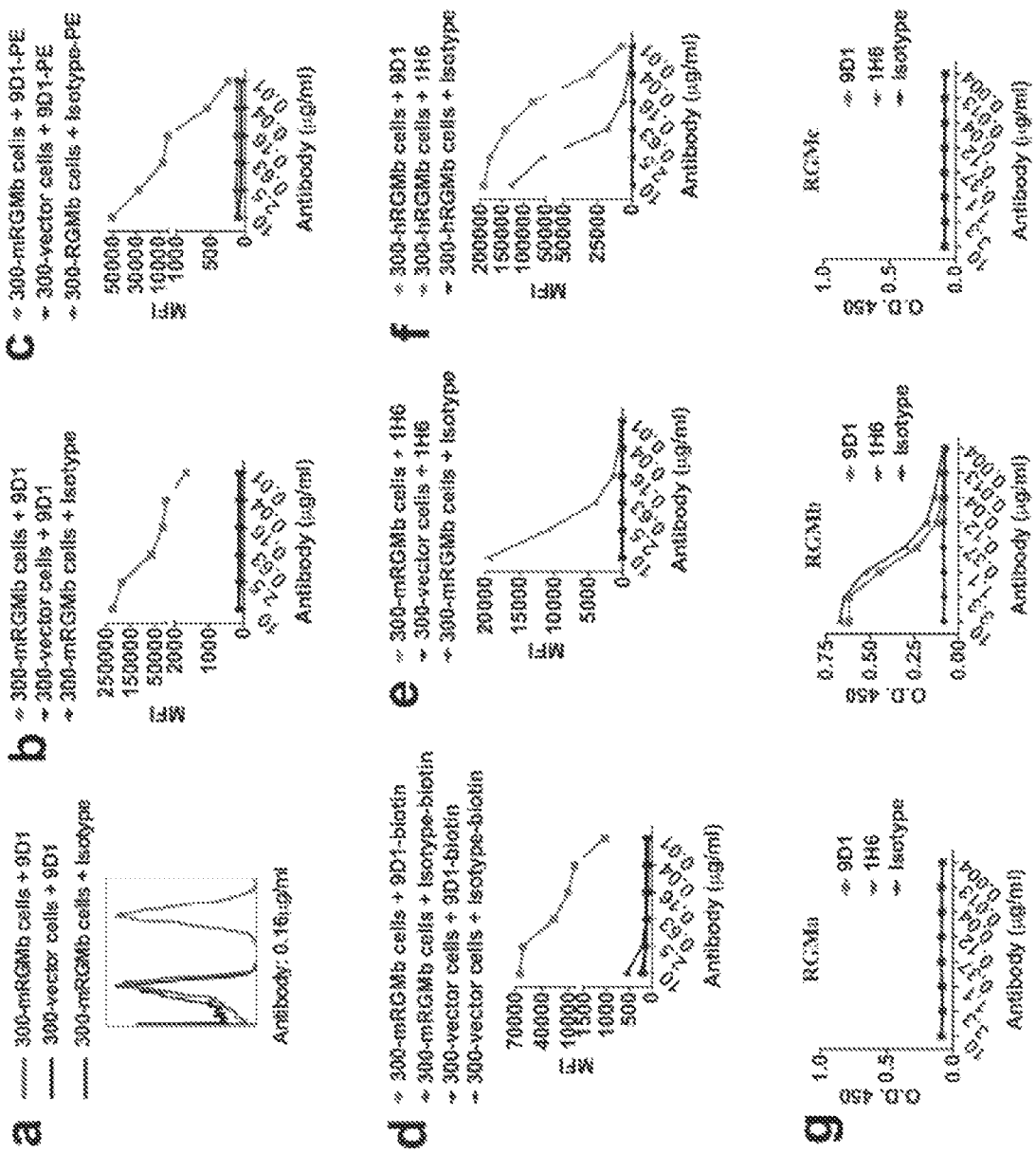
FIG. 2 includes eight panels, identified as panels (A), (B), (C), (D), (E), (F), (G), and (H), which show that RGMb mAbs bind to RGMb, but not to RGMa or RGMc. Panels A-F show the results of binding of RGMb mAbs to mouse and human RGMb transfected cells. mRGMb, hRGMb or vector (mPD-L2) transfected 300 cells were stained with the indicated concentrations of mRGMb mAbs (9D1 and 1H6 are shown) or isotype controls, and analyzed by flow cytometry. MFI: mean florescence intensity. Panel G shows the results of binding of RGMb mAbs to RGMa. RGMb or RGMc. Mouse recombinant mRGMa-HIS, mRGMb-HIS or mRGMc-HIS were coated on ELISA plates. The indicated concentrations of 5 RGMb mAbs (only 9D1 and 1H6 are shown) or the isotype control were added and binding was detected with anti-rat IgG-HRP. Panel H shows the results and specificities of anti-IL17RB and anti-NEO mAb generation. Data shown in Panels 2A-2F are representative of two or more independent experiments.
Figure 2:
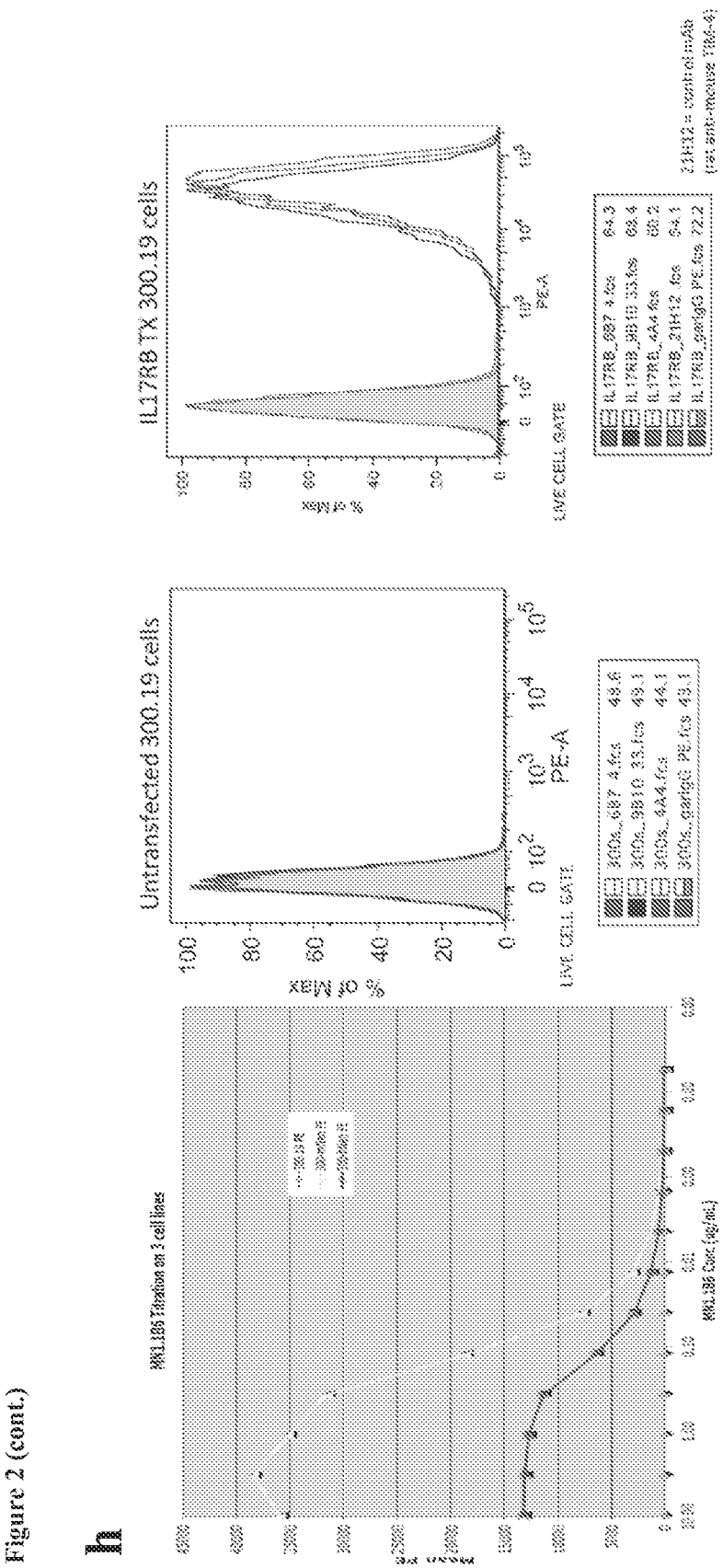
Figure 3:
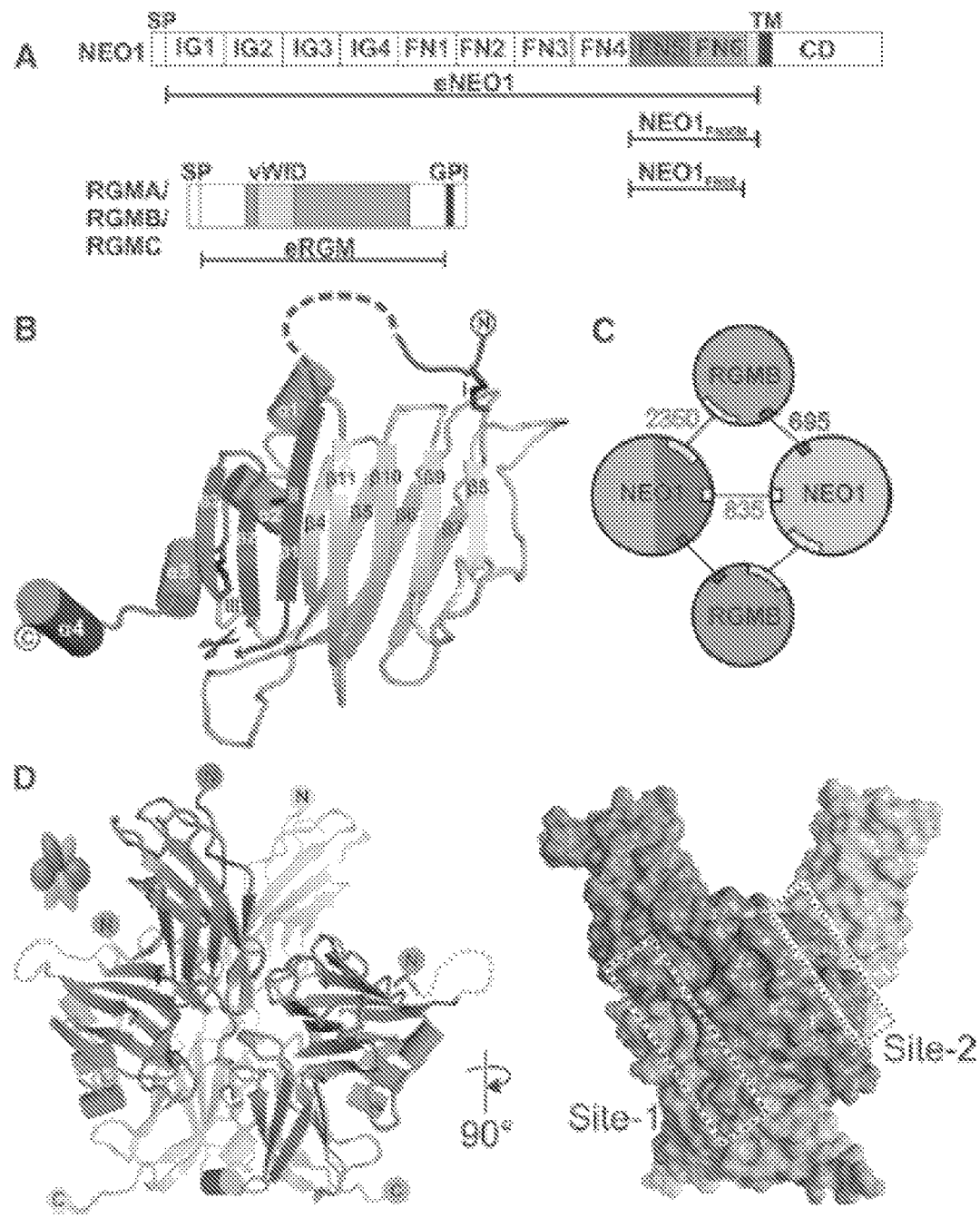
FIG. 3 includes four panels, identified as panels (A), (B), (C), and (D), which show a molecular model depicting the RGMb:neogenin binding region reproduced from FIG. 1 of Bell et al. (2013) *Science* 341:77. Panels A-D provide crystal structure data indicating that RGMb and NEO1 form a complex having a 2:2 stoichiometry and the detailed biophysical interaction faces and residues between RGMb and NEO1 have been mapped.

RGMb mAbs showing specificity by flow cytometry on mRGMb and/or hRGMb transfected 300-cells, ELISA and Western blotting were identified. For example, two mRGMb mAbs, 9D1 and 8B2, were identified that blocked interaction of RGMb with PD-L2 (FIG. 1A). These RGMb antibodies do not bind to mRGMa or mRGMc (FIG. 2G).

It was also determined whether mPD-L2 mAbs would block PD-L2 interactions with RGMb since RGMb is known to bind directly to BMP-2/4 (Samad et al. (2005) *J. Biol. Chem.* 280:14122-14129; Wu et al. (2012) *PLoS One* 7:e46307). mPD-L2 mAb, 2C9, blocked PD-L2:RGMb but not PD-L2:PD-1 interactions, and three mPD-L2 mAbs, 3.2, TY25 and MIH37, blocked both PD-L2:RGMb and PD-L2:PD-1 interactions (FIGS. 1B-1C). TY25 and 3.2 share the same epitope, while 2C9 recognizes a different epitope. The existence of both single and double blocker PD-L2 mAbs indicates that the PD-1 and RGMb binding sites on PD-L2 are close but distinct. As described above, the properties of RGMb and PD-L2 mAbs are summarized in Table 2.

The capacities of RGMb antibodies to block RGMb binding to BMP-2/4. 9D1 and 8B2 blocked RGMb binding to BMP-2/4 in an ELISA were also tested (FIG. 1D) and thus are dual blockers of RGMb interactions with PD-L2 and BMP-2/4. However. PD-L2-Ig fusion protein did not block RGMb binding to BMP-2/4 in an ELISA (FIG. 1D). These data suggest that the binding sites on RGMb for PD-L2 and BMP are close but distinct.

To test if RGMb can bind both PD-L2 and BMP at the same time, an ELISA was performed to analyze the binding of PD-L2-Ig fusion protein to immobilized BMP-2/4 in the presence or absence of RGMb. PD-L2 could not directly bind to BMP-2/4, but in the presence of RGMb could form a complex with BMP when RGMb and PD-L2-Ig were added simultaneously or sequentially to BMP-2/4 (FIG. 1E). These data are consistent with RGMb having distinct sites for PD-L2 and BMP binding, and show that RGMb has the capacity to form a trimeric complex with BMP and PD-L2.

RGMb also binds to neogenin (Bell et al. (2013) *Science* 341:77-80; Conrad et al. (2010) Mol. Cell Neurosci. 43:222-231). Furthermore, neogenin has been shown to directly bind BMP-2/4/6/7, and modulate BMP signaling (Hagihara et al. (2011) *J. Biol. Chem.* 286:5157-5165; Tian and Liu (2013) Mol. Reprod. Dev. 80:700-717). It was found that soluble RGMb-mIgG2a bound to neogenin transfected 300 cells (FIG. 1F). RGMb mAbs weakly blocked RGMb-mIgG2a binding to neogenin (FIG. 1G). Cell conjugation assays showed that 300-mRGMb cells did not bind to 300-neogenin cells, suggesting that the structural orientation of RGMb and neogenin binding is not compatible with cell to cell binding but can support binding in cis on the same cell surface or of soluble RGMb to cell surface neogenin.

Finally, Table 3 provides sequences for the isolated rat anti-mouse/anti-human RGMb 9D1 monoclonal antibody. Briefly, the variable domain of the light and heavy chains of the 9D1 mAb have been sequenced and the complementarity determining regions (CDR) domains thereof are provided. Numbering is shown according to nucleic acid positions and the corresponding amino acid residues, corresponding to CDRs, for example, can easily be identified based on the provided translations.

TABLE 3

9D1 mAb sequence

```
9D1 Light Chain Variable (vK) DNA and Amino Acid Sequences
LOCUS         9D1_LS-VK         378 bp    DNA     linear
DEFINITION    9D1, DNA 378 bases.
FEATURES           Location/Qualifiers
    J_segment      349 . . . 378
                   /label = JK
    V_segment      325 . . . 348
                   /label = CDR3
    V_region       229 . . . 324
                   /label = FWR3
    V_segment      208 . . . 228
                   /label = CDR2
    V_region       163 . . . 207
                   /label = FWR2
    V_segment      130 . . . 162
                   /label = CDR1
    V_region       61 . . . 129
                   /label = JK
    sig_peptide    1 . . . 60
                   /vntifkey = "94"
                   /label = LS
    CDS            1 . . . 378
                   /label = 9D1\LS-VK
```

TABLE 3-continued

9D1 mAb sequence

/translation = "MMAAVQLLGLLLLCLRAMRCSIQMTQSPSHLSASVGDRVTLSCKVSQNIYKYL
NWYQQKLGEAPKLLIYYTSFLQTGIPSRFSGSGSGTDYTLTISSLQPEDVATYFCQKYYSGQTFGGGTK
LEIK" (SEQ ID NO: 25)

BASE COUNT    103 a     91 c     89 g     95 t
ORIGIN

```
  1 atgatggctg cagttcagct cttagggctt ttgctgctct gcctccgagc catgagatgt
 61 gacatccaga tgacccagtc tccttcacac ctgtcagcat ctgtgggaga cagagtcact
121 ctcagctgca aagtaagtca gaatatttac aagtacttaa actggtatca gcaaaaactt
181 ggagaagctc ccaaactcct gatatattat acaagctttt tgcaaacggg catcccgtca
241 aggttcagtg gcagtggatc tggtacagat tacacactca ccatcagcag cctgcagcct
301 gaagatgttg ccacatattt ctgccagaag tattatagcg ggtggacgtt cggtggaggc
361 accaagctgg aattgaaa
```
(SEQ ID NO: 26)

```
9D1 Heavy Chain Variable DNA and Amino Acid Sequences
LOCUS        9D1_LS-VH          408 bp    DNA        linear
DEFINITION   9D1, DNA 408 bases.
FEATURES          Location/Qualifiers
     J_segment    376 . . . 408
                  /label = JH
     V_segment    352 . . . 375
                  /label = CDR3
     V_region     256 . . . 351
                  /label = FWR3
     V_segment    205 . . . 255
                  /label = CDR2
     V_region     163 . . . 204
                  /label = FWR2
     V_segment    148 . . . 162
                  /label = CDR1
     V_region      88 . . . 147
                  /label = FWR1
     sig_peptide    1 . . .  87
                  /label = LS
     CDS            1 . . . 408
                  /label = 9D1\LS-VH
```

/translation = "MGWSQIILFLVAATTCVHSQVQLQQSGTELVKPGSSVKISCKASGDTFTSDYM
HWIRQQPGSGLEWIGWIYPGNGNTKYNQKFDGKATLTADKSSSTAYLQLSLLTSEDYAVYFCARQTEGY
FDYWGQGVMVTVSS" (SEQ ID NO: 27)

BASE COUNT    107 a     97 c    106 g     98 t
ORIGIN

```
  1 atgggatgga gccagatcat tctctttctg gtggcagcaa ctacatgtgt ccactcccag
 61 gtacagctac agcaatcagg gactgaactg gtgaagcctg ggtcctcagt gaaaatttcc
121 tgcaaggctt ctggcgacac cttcaccagt gactatatgc actggataag gcagcagcct
181 ggaagtggcc ttgagtggat tgggtggatt tatcctggaa atggtaatac taagtacaat
241 caaaagttcg atgggaaggc aacactcact gcagacaaat cctccagcac agcctatttg
301 cagctcagcc tcctgacatc tgaggactat gcagtctatt tctgtgcaag acagacggag
361 gggtactttg attactgggg ccaaggagtc atggtcacag tctcctca
```
(SEQ ID NO: 28)

The mAbs were conjugated with biotin using a standard protocol, or with Alexa 594 by BioLegend Inc.

In addition, monoclonal antibodies specific for IL17RB, the IL-25 receptor subunit which confers specificity for IL-25, were generated by subcutaneous immunization of female Lewis strain rats (Harlan Sprague-Dawley) with mouse IL17RB-Ig. Rats were boosted multiple times with mouse IL17RB-Ig in PBS or IFA. At 1 day (d) following the last boost, lymph node cells were depleted of T cells using MACS beads (Miltenyi), fused with NS1 myeloma cells, and cloned. MAbs specific for neogenin were generated by immunization of rats with mouse neogenin-Ig using a similar protocol. Hybridoma supernatants were screened for cell surface staining of mouse IL-17RB-transfected 300.19 cells or neogenin-transfected cells and for lack of reactivity with untransfected cells (FIG. 2H). Neogenein (NEO) mAb clone 1B6 was selected for further use since it also specifically stained tissue sections of murine NEO-transfected but not control-transfected cells. MAbs were purified using protein G-agarose (Pierce Biotechnology, Rockford, Ill.), and coupled to Alexa 647 (IL17RB clone 9B10) or Brilliant Violet 421 (Neogenin clone 1B6) by Biolegend, Inc.

C. Measurement of Airway Hyperreactivity

To induce AHR, mice were immunized with 100 μg OVA (ICN Biomedical) adsorbed in 2 mg ALUM intraperitoneally (i.p.) and were given intranasal OVA (100 μg i.n.) or saline on day 7, 8 and 9. In some experiments, mice were treated with RGMb mAb 9D1, PD-L2 mAb 2C9 or control mAb i.p. One day after the final dose of OVA, mice were sedated, tracheostomized and ventilated. Direct measurement of airway resistance and dynamic compliance was performed by invasive plethysmography (BUXCO systems). Mice were anesthetized with pentobarbital (50 mg per kg body weight), then tracheotomised, intubated and mechanically ventilated at a tidal volume of 0.2 ml and a frequency of 150 breaths per minute as described in (Akbari et al. (2003) *Nat. Med.* 9:582-588). Baseline lung resistance and responses to aerosolized saline (0.9% NaCl) were measured first, followed by measurement of responses to increasing doses of aerosolized acetyl-β-methylcholine chloride methacholine (0.125-40 mg/ml; Sigma-Aldrich). The three highest values of lung resistance obtained after each dose of methacholine were averaged to obtain the final values for each 3 minute dose of methacholine.

D. BAL Fluid and Histopathology

Following measurement of AHR and euthanasia, the lungs were lavaged three times with 1 ml of PBS 2% FCS and the fluid pooled. The relative number of different types of leukocytes was determined from slide preparations of BAL fluid stained with hematoxylin and eosin (H&E). For histopathology, lungs were flushed with PBS to remove blood, infused with 10% (vol/vol) formalin, and embedded in paraffin. Lung sections 5 µm in thickness were cut and stained with H&E.

E. Immunofluorescence Microscopy Staining

Figure 9:
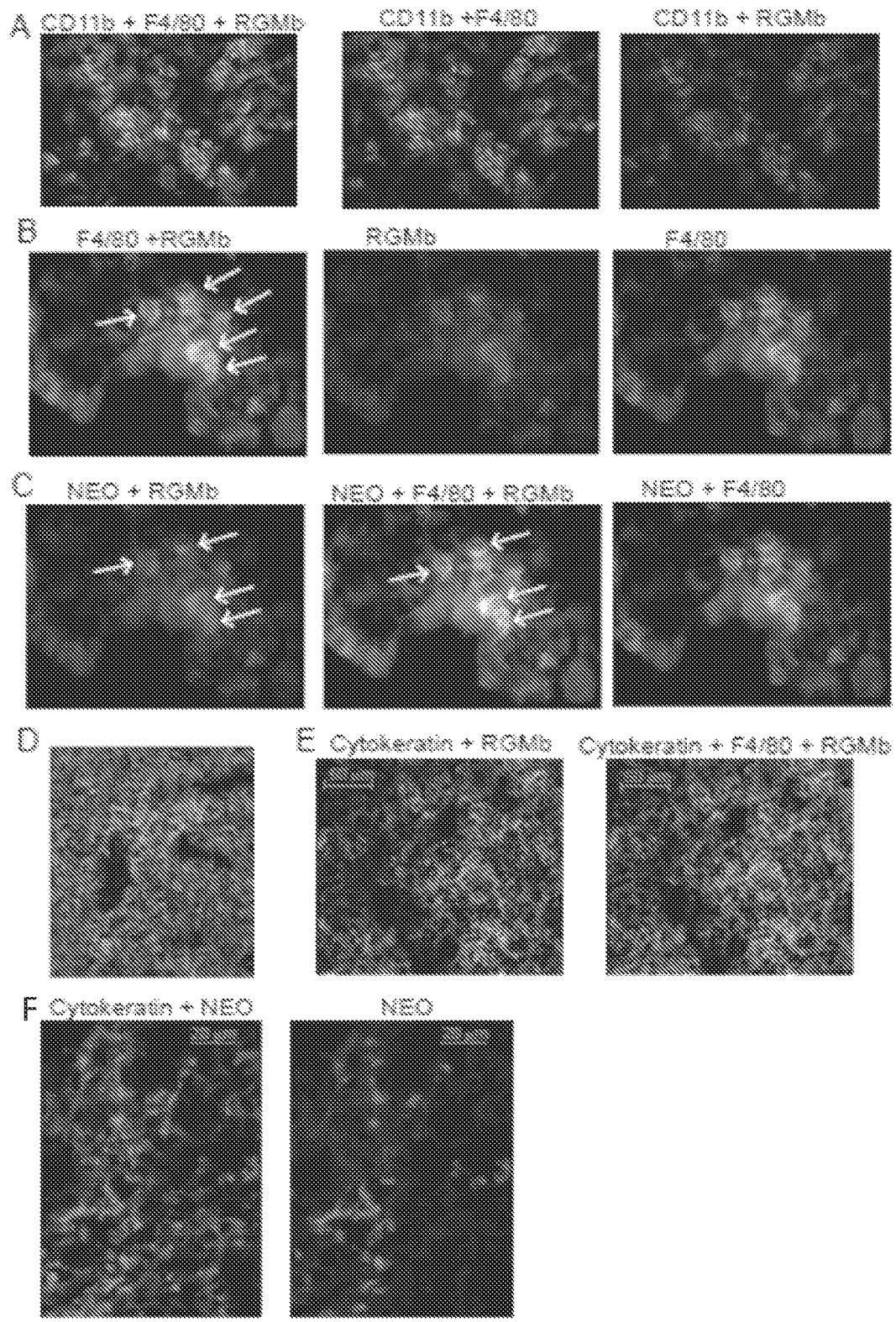
FIG. 9 includes six panels, identified as panels (A), (B), (C), (D), (E), and (F), which show that RGMb and neogenin are expressed on CD11b$^+$F4/80$^+$ myeloid cells in the lungs following allergen sensitization and challenge, and are located adjacent to epithelial cells. Lungs of mice sensitized and challenged with OVA were removed on day 10 and frozen sections prepared. Panel A shows immunofluoresence images showing colocalization of CD11b, F4/80, and RGMb. Co-localization can be determined from the images. The white arrows of panel B indicate co-localization of F4/80 mAb with RGMb mAb in overlay. Panel C shows the results of sections stained with neogenin mAb, RGMb mAb, and F4/80 mAb. The left sub-panel shows co-localization of neogenin with RGMb, shown with white arrows. The right sub-panel shows co-localization of F4/80 and neogenin. The center sub-panel shows triple co-localization of NEO, RGMb and F4/80, shown with white arrows. Images shown are representative of at least 4 animals. Panel D shows the results of sections stained with pan-cytokeratin mAb and F4/80 mAb. Panel E shows the results of sections stained with pan-cytokeratin mAb, RGMb mAb, and F4/80 mAb. Panel F shows the results of sections stained with pan-cytokeratin mAb.

Lung samples were mounted in OCT Tissue-Tek® compound (Sakura Finetek). Seven µm frozen sections were cut and affixed to glass slides. Sections were fixed in acetone for 10 minutes and slides were blocked with 10 µg/mL Fc block, 10% rat serum, 2.5% BSA. Slides were then stained with combinations of antibodies as follows: FIG. 9A: CD11b Pacific Blue, anti-F4/80 Alexa Fluor 488, and anti-RGMb Alexa Fluor 594; FIG. 9B: F4/80 Alexa 488 and anti-RGMb Alexa Fluor 594; and FIG. 9C: anti-NEO 1B6 BV421, F4/80 Alexa 488, RGMb Alexa Fluor 594 in 2% rat serum, 0.5% BSA. For detection of epithelial cells (FIG. 9D), lung sections were stained with anti-pan-cytokeratin (PCK-26, Abcam), followed by staining with Alexa Fluor 488 F(ab')$_2$ fragment of goat anti-mouse IgG, followed by staining with anti-F4/80 Pacific Orange. In FIG. 9E, slides were stained with mouse anti-pan cytokeratin in 2% goat serum, followed by staining with Alexa Fluor 488 F(ab')$_2$ fragment of goat anti-mouse IgG, followed by staining with anti-RGMb Alexa 594 and anti-F4/80 Pacific Blue. For FIG. 9F, slides were stained with anti-pan cytokeratin, followed by staining with Alexa Fluor 594 F(ab')$_2$ fragment of goat anti-mouse IgG, followed by anti-NEO1B6 Alexa 488.

Anti-CD11b pacific blue, anti-CD11c Alexa Fluor 488 (BioLegend, Inc.), anti-F4/80 pacific orange (Life Technologies), or anti-F4/80 pacific blue (BioLegend, Inc.) were used as indicated in the figure legends.

Secondary antibodies were obtained from Molecular Probes. Image dimensions and resolution were then adjusted for publication using Adobe Photoshop®.

F. Cell Isolation and Stimulation

Spleen cells were isolated by mechanically disrupting the tissues, depleted of B cells and restimulated in vitro with OVA. Culture supernatants were collected after 4 days for analysis of cytokines by ELISA.

G. FACS Antibodies and Analysis

For FACS analysis of lung cells, the lung was perfused with PBS, cut into small pieces, digested in RPMI 1640 with 5% FBS, 1.6 mg/ml collagenase IV (Worthington Biochemical Corporation, MA) and 200 u/ml DNase I (Roche) and then treated with red blood cell lysing buffer (Sigma). The following antibody cocktail was used for staining: CD11c APC-eFluor 780, CD11b PerCP/Cy5.5, F4/80 Alexa Fluor 700, CD45 PE-Texas-Red, Gr-1 PE-Cy7 (all from BioLegend, Inc.), IL-17RB Alexa Fluore 647, RGMb-biotin or rIgG2a-biotin with streptavidin-PE, and RGMb 9D3-biotin or rIgG2a-biotin, with streptavidin-PE.

H. qRT-PCR

Total RNA was isolated from lung tissues using a RNeasy mini kit (QIAGEN), and cDNA was synthesized using iScript™ cDNA synthesis kit (Invitrogen, CA). qPCR using TaqMan® universal master mix (Applied Biosystems) and gene-specific TaqMan® probe was carried out in a 7500 Sequence Detection System (Applied Biosystems). The levels of target gene expression were normalized to GAPDH expression using the $2^{-\Delta\Delta Ct}$ m method. The following primers and probes were purchased from Applied Biosystems: mouse GAPDH (4352339E), IL-4 (Mm00445258_g1), IL-5 (Mm00439645_m1), and IL-13 (Mm00434204_m1).

I. Microarray

Total RNA was extracted and assessed by using the RNeasy) Kit (Qiagen). In order to obtain genome-wide expression profiles, RNA samples were sent to the Microarray Core Facility at the Dana Farber Cancer Institute (Boston, Mass.) for amplification and hybridization on the Mouse Gene 1.0 ST array (Affymetrix; Santa Clara, Calif.). Raw data for sample populations were preprocessed and normalized using the RMA algorithm in the ExpressionFileCreator module in GenePattern® (Reich et al. (2006) *Nat. Genet.* 38:500-501). The resulting data were subsequently analyzed in the Multiplot Suite in GenePattern by first filtering out genes with low expression value (<100 in all subsets) and noisy genes (CV>0.8), and then selecting for genes upregulated or downregulated (fold change (FC) less than or equal to 0.6 or FC greater than or equal to 1.6, respectively). One-way ANOVA Tukey HSD p-value<0.05) in the inflamed lung (isotype) relative to the naive lung (saline group) was used. These genes of interest were subsequently divided into further subgroups based on the degree of upregulation or downregulation resulting from treatment with aRGMb. The heat maps were generated with the GENE-E module (available on the World Wide Web at broadinstitute.org/cancer/software/GENE-E/) in GenePatterncite and compiled for publication using Adobe Illustrator.

Example 2: Treatment with Anti-RGMb mAb Inhibits the Development of AHR

Figure 4:
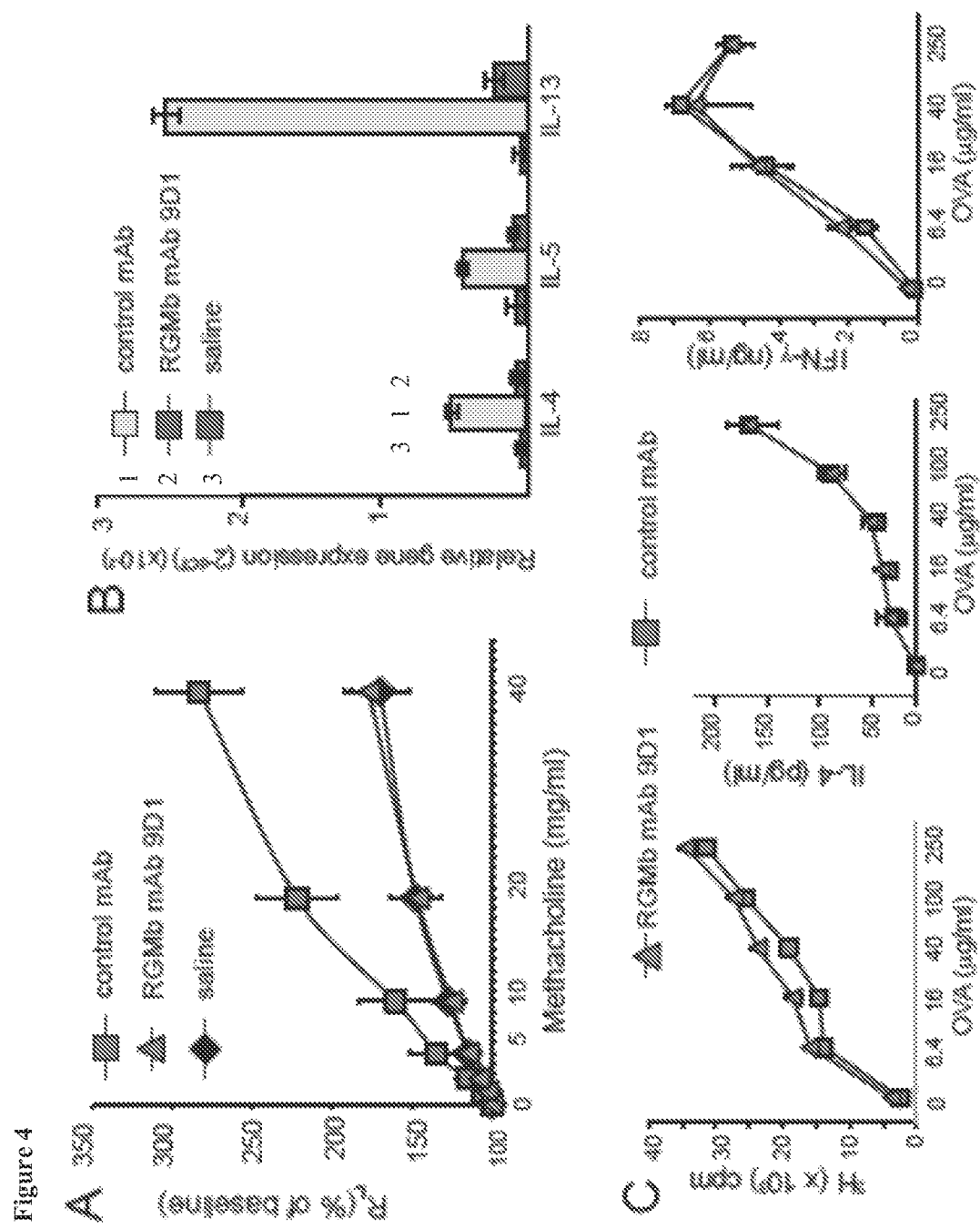
FIG. 4 includes six panels, identified as panels (A), (B), (C), (D), (E), and (F), which show that the development of induced airway hypersensitivity reactions (AHR) is blocked using a blocking RGMb mAb. Panel A shows the results of mice sensitized and challenged with OVA or saline on days 7, 8, and 9, and assessed for the development of AHR on day 10. Mice were treated with RGMb mAb or isotype control (500 μg) on days 0, 4, and 8. Panel B shows the level of target gene expression in mRNA from lung tissue as expressed relative to GAPDH. Panel C shows the results of B cell-depleted splenocytes prepared from mice immunized with OVA in alum i.p and restimulated with OVA for 4 days. Culture supernatants were examined for cytokine production by ELISA. Panel D shows the results of mice sensitized and challenged with OVA as in Panel 4A and treated with RGMb mAb or isotype control (500 μg) on days 6 and 8 and assessed for AHR on day 10. Panel E shows the results of lung tissue from the mice in Panel D stained with H&E and analyzed for cell infiltration. Panel F shows the results of BAL fluid from the mice in Panel 4 analyzed following AHR measurement.
Figure 4:
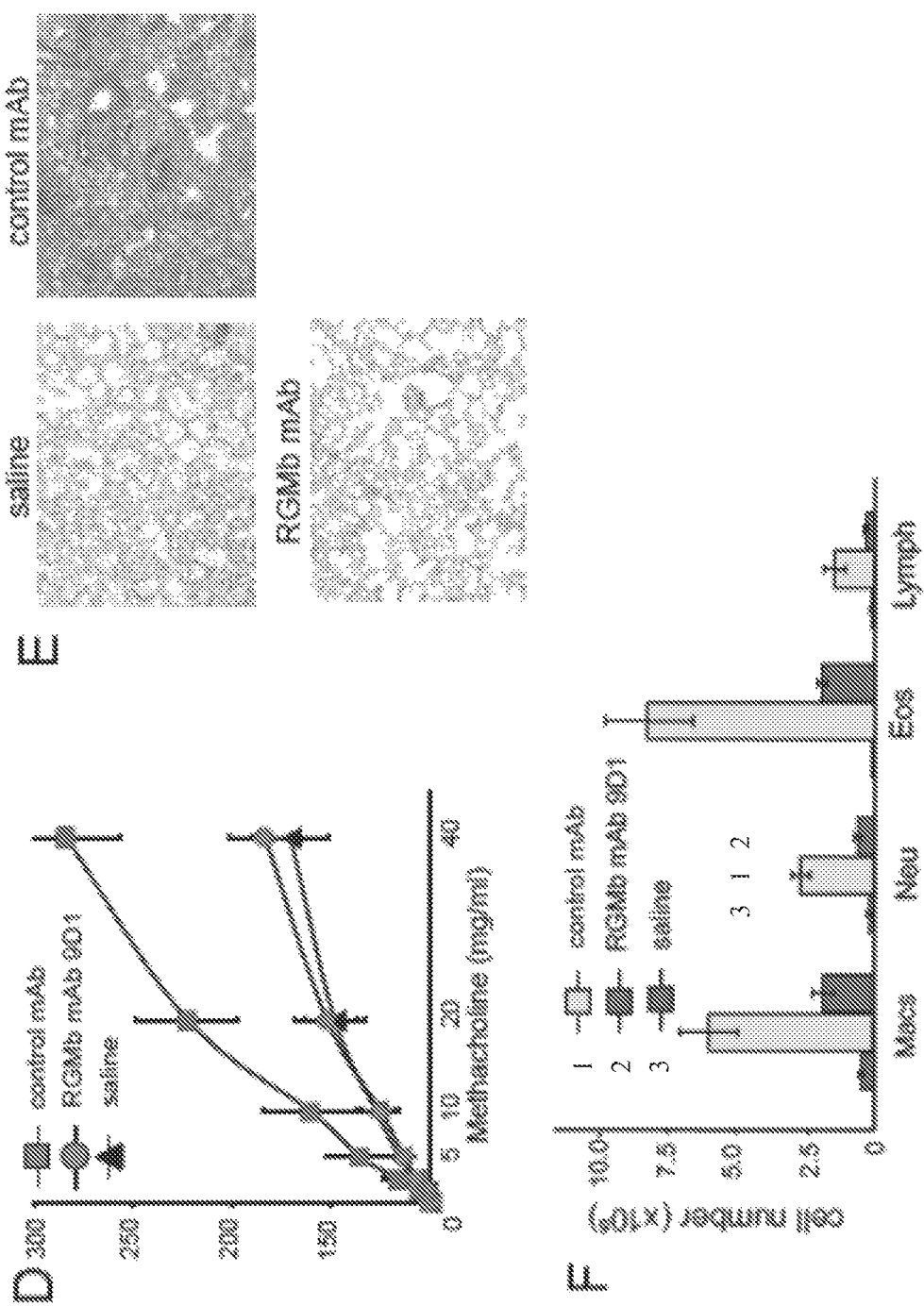

To determine the role of RGMb in the development of allergen-induced AHR an experimental mouse model of allergic asthma was used and the mice were treated with RGMb blocking antibody. BALB/c mice sensitized with OVA in alum were challenged with OVA intranasally to induce AHR. Mice were treated with RGMb mAb or control mAb throughout the protocol, both at the time of sensitization with OVA/alum i.p. and prior to challenge with OVA i.n. OVA-sensitized and challenged mice treated with control mAb developed severe AHR as expected compared with control saline challenged mice (FIG. 4A). In contrast, treatment with RGMb mAb inhibited the development of AHR, such that mice treated with RGMb mAb developed only mild AHR, similar to that of saline control mice. Moreover, levels of IL-4, -5 and -13 were substantially reduced in the lungs of mice treated with RGMb mAb as measured by real-time RT-PCR (FIG. 4B).

Example 3: RGMb mAb Inhibits AHR at the Effector Stage but not at the Sensitization Stage RGMb mAb treatment could inhibit development of AHR by acting at the effector stage in the lung or by acting at the initiation of the response during the sensitization to allergen. To determine if treatment with RGMb mAb inhibited the sensitization to OVA, mice were given RGMb mAb i.p. one day prior to sensitization with OVA in alum. Eight days later, splenic T cell responses upon restimulation with OVA in vitro were examined. T cells from OVA sensitized, control mAb-treated mice proliferated vigorously in response to in vitro restimulation with OVA and produced IL-4 and IFN-γ. Responses of mice treated with RGMb mAb did not differ from those of control mAb treated mice (FIG. 4C). This indicates that treatment with RGMb mAb does not inhibit sensitization of the mice with OVA in alum.

To determine if RGMb was acting at the effector stage during the response to OVA in the lung, mice sensitized with OVA/alum were treated with RGMb mAb on day 6 and 8, prior to the intranasal challenge with OVA. Mice treated with control mAb had high levels of AHR as expected, but administration of RGMb mAb greatly inhibited the development of AHR in the previously sensitized mice (FIG. 4D). Lung tissue of mice treated with control mAb demonstrated allergen-induced airway inflammation characterized by extensive cellular infiltration surrounding the airways and increased numbers of eosinophils in the BAL fluid compared with saline challenged mice. In contrast, lungs of mice treated with RGMb mAb had significantly reduced lung inflammation (FIGS. 4E-4F).

Figure 5:
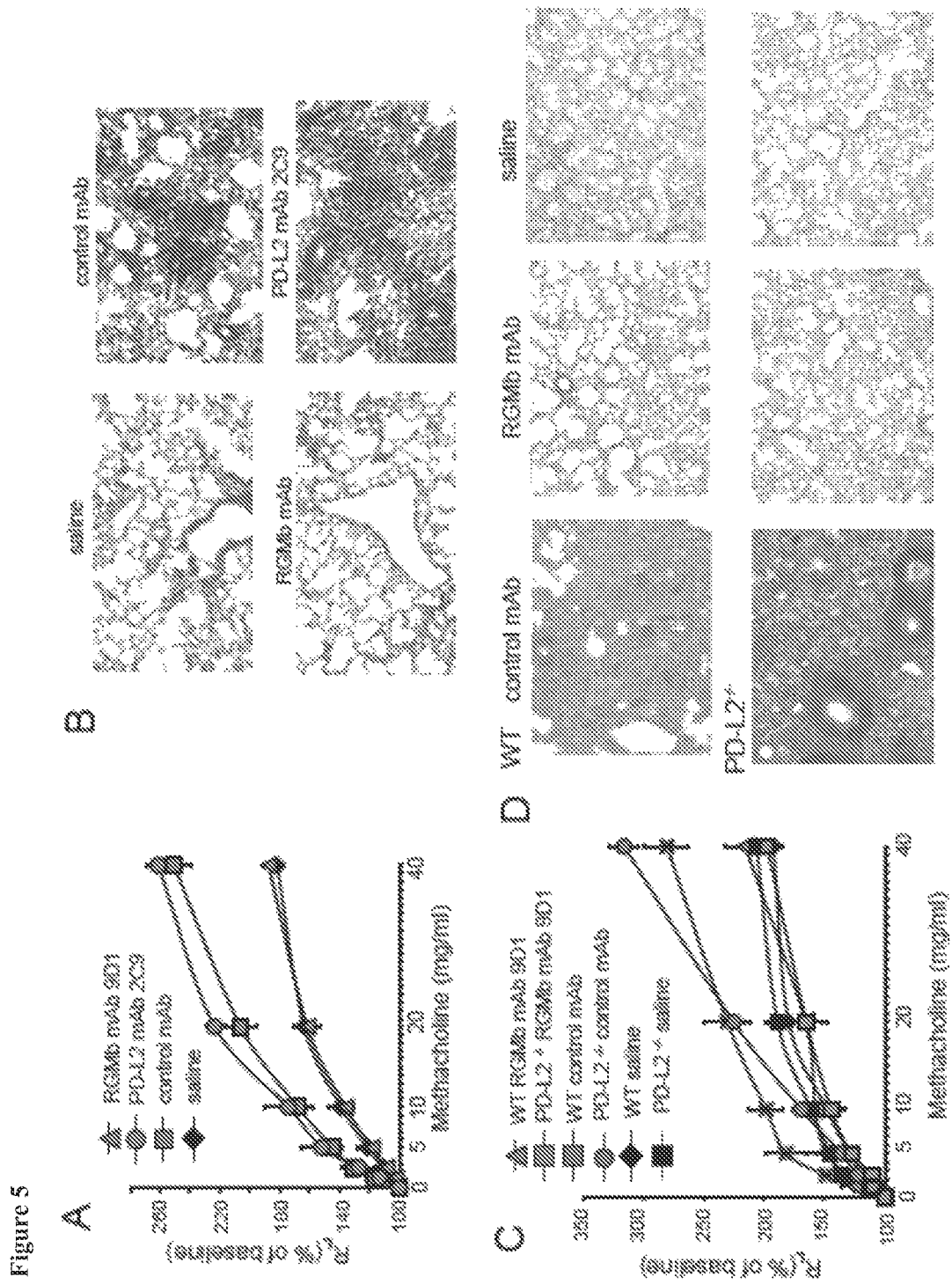
FIG. 5 includes five panels, identified as panels (A), (B), (C), (D), and (E), which show that RGMb blockade of AHR and lung inflammation does not involve RGMb:PD-L2 interaction. Panel A shows the results of mice sensitized and challenged with OVA as in FIG. 4 treated with RGMb mAb 9D1, PD-L2 mAb 2C9 or isotype control on days 0, 4, and 8. Panel B shows the results of lung tissue from the mice in Panel 5A stained with H&E and analyzed for cell infiltration. Panel C shows the results of PD-L2-deficient or WT mice sensitized and challenged with OVA treated with RGMb mAb or isotype control (500 μg) on days 0, 4, and 8 and assessed for AHR on day 10. Panel D shows the results of lung tissue from the mice in Panel C stained with H&E and analyzed for cell infiltration. Panel E shows the results of BAL fluid from the mice in Panel C analyzed following AHR measurement.
Figure 5:
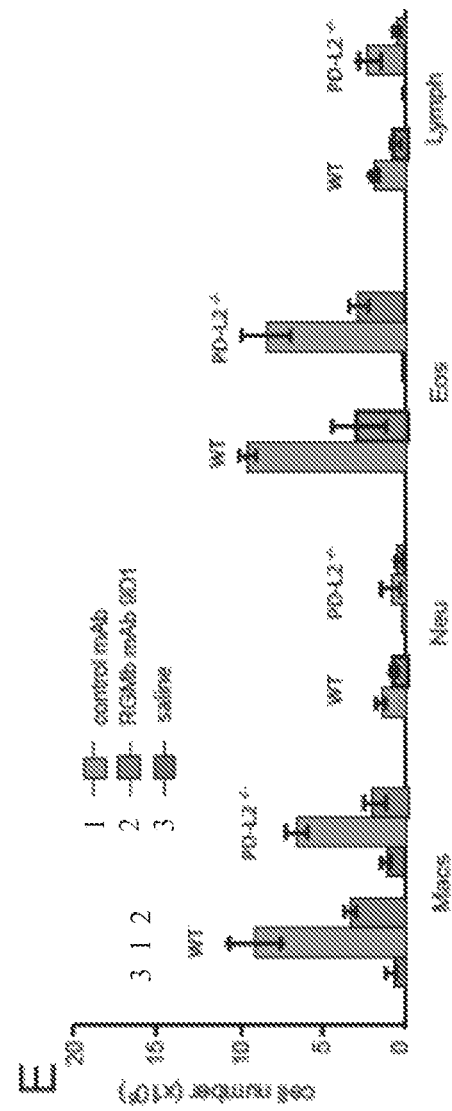

Example 4: Blockade of RGMb Interaction with PD-L2 does not Inhibit Development of AHR FIG. 1 provides data indicating that PD-L2 is a ligand of RGMb in addition to the previously identified RGMb ligands, neogenin and BMPs and that RGMb binding to PD-L2 in the lung promotes respiratory tolerance (Xiao et al. (2014) *J. Exp. Med.* 211:943-959). To examine a possible role of RGMb:PD-L2 interaction in the model, the effect of treatment with anti PD-L2 mAb 2C9, which blocks the interaction of PD-L2 with RGMb but does not inhibit PD-L2:PD-1 interaction, was examined. While development of AHR was blocked in mice treated with RGMb mAb, mice treated with PD-L2 mAb 2C9 developed AHR, similar to that in mice treated with control mAb (FIG. 5A). The lung histology of mice shown in FIG. 5A was analyzed by hematoxylin and eosin to determine cellular infiltration. Consistent with their development of AHR, lung tissue of OVA sensitized and challenged mice treated with PD-L2 mAb 2C9 demonstrated extensive cellular infiltration surrounding the airways and thickened membrane. Mice treated with PD-L2 mAb 2C9 demonstrated levels of cellular infiltration in lung tissue similar to that of mice treated with control mAb. In contrast, lung tissue of mice treated with RGMb mAb showed little cellular infiltration and was similar to that of saline treated mice (FIG. 5B). These results demonstrate that treatment with RGMb mAb prevents the development of lung inflammation and indicate that interaction of RGMb with PD-L2 does not affect the development of AHR.

To further rule out an involvement of RGMb interaction with PD-L2, the effect of treatment with RGMb mAb in PD-L2$^{-/-}$ mice was examined. OVA-sensitized and challenged PD-L2$^{-/-}$ mice developed robust AHR and airway inflammation as expected (Akbari et al. (2010) *Mucosal Immunol.* 3:81-91), and this was blocked by treatment with RGMb mAb (FIGS. 5C-5D). These results confirm that an interaction of RGMb with PD-L2 does not contribute to the role of RGMb in AHR and airway inflammation.

Example 5: Lung Gene Expression Analysis Following RGMb mAb Treatment

Figure 6:
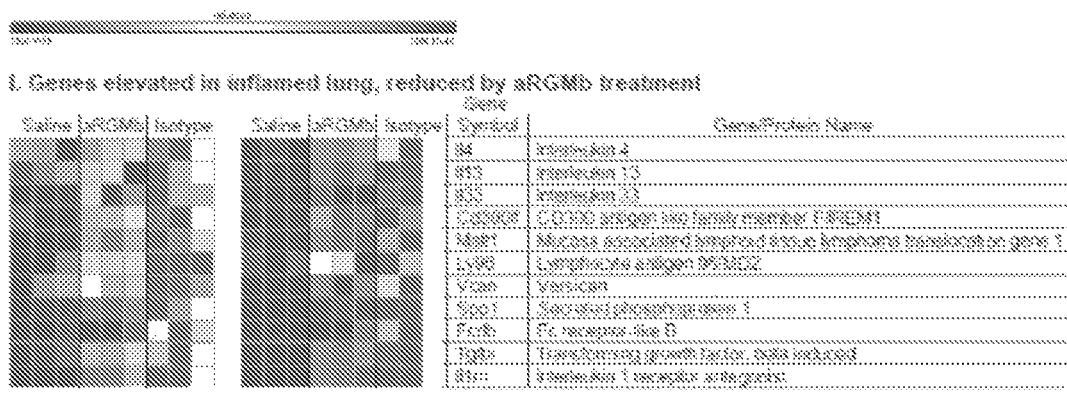
FIG. 6 shows the results of microarray experiments described in Example 5. For Groups I, II, and III, Saline represents row min. expression, aRGMb represents intermediate expression, and Isotype represents row max. expression. For Group IV, Saline represents row max. expression, aRGMb represents intermediate expression, and Isotype represents row min. expression.
Figure 6:
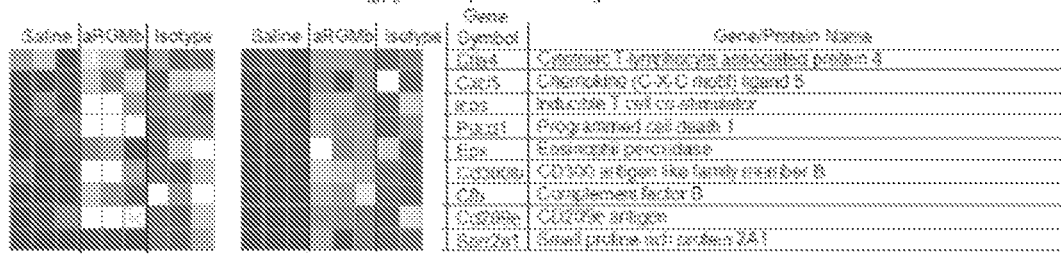
Figure 6:
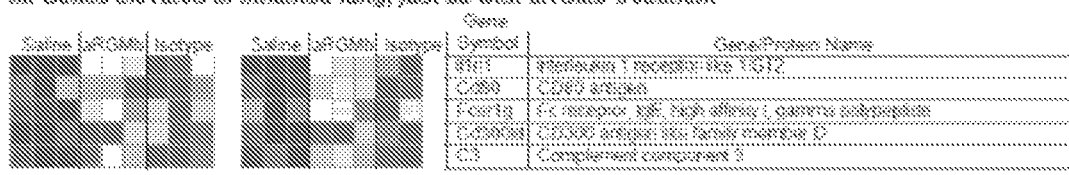
Figure 6:
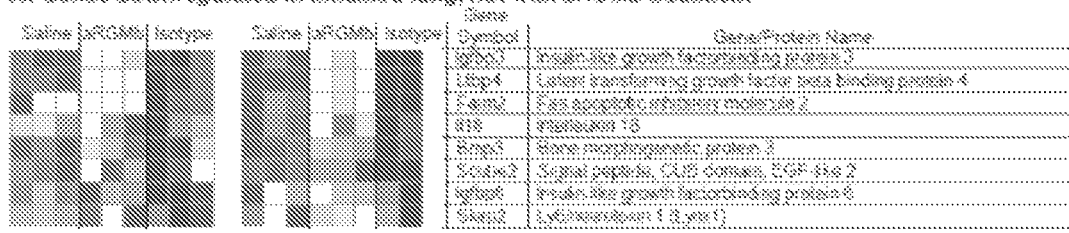

To investigate the molecular basis for the effects of anti-RGMb treatment, mice sensitized and challenged with OVA or saline were treated with RGMb or control mAb. Gene expression microarray analysis was performed on whole lung tissue harvested 24 hr after the last intranasal challenge. Allergen sensitization and challenge induced a set of genes, many of which are known to be associated with type 2 immune responses including IL-13, IL-33 and IL1RL1 (ST2, the IL-33 receptor), which have been identified as asthma-associated genes in genome-wide association studies (Moffatt et al. (2010) *N. Engl. J. Med* 363:1211-1221). Also upregulated are T cell activation molecules, including CTLA4, ICOS and other inflammation-associated molecules and receptors (FIG. 6, Groups I-III). Treatment with RGMb mAb inhibited expression of a subset of these genes including IL-13, IL-4 and IL-33 (FIG. 6, Group 1) and reduced those in another subset (FIG. 6, Group II). Overall, these data show that treatment with RGMb mAb in a model of allergen-driven asthma inhibits expression of a set of genes that is critical for the allergic asthma response and supports our finding that RGMb treatment inhibits the development of lung inflammation and AHR.

Example 6: IL-25 is Required for Allergen-Induced Airway Hyperreactivity

Figure 7:
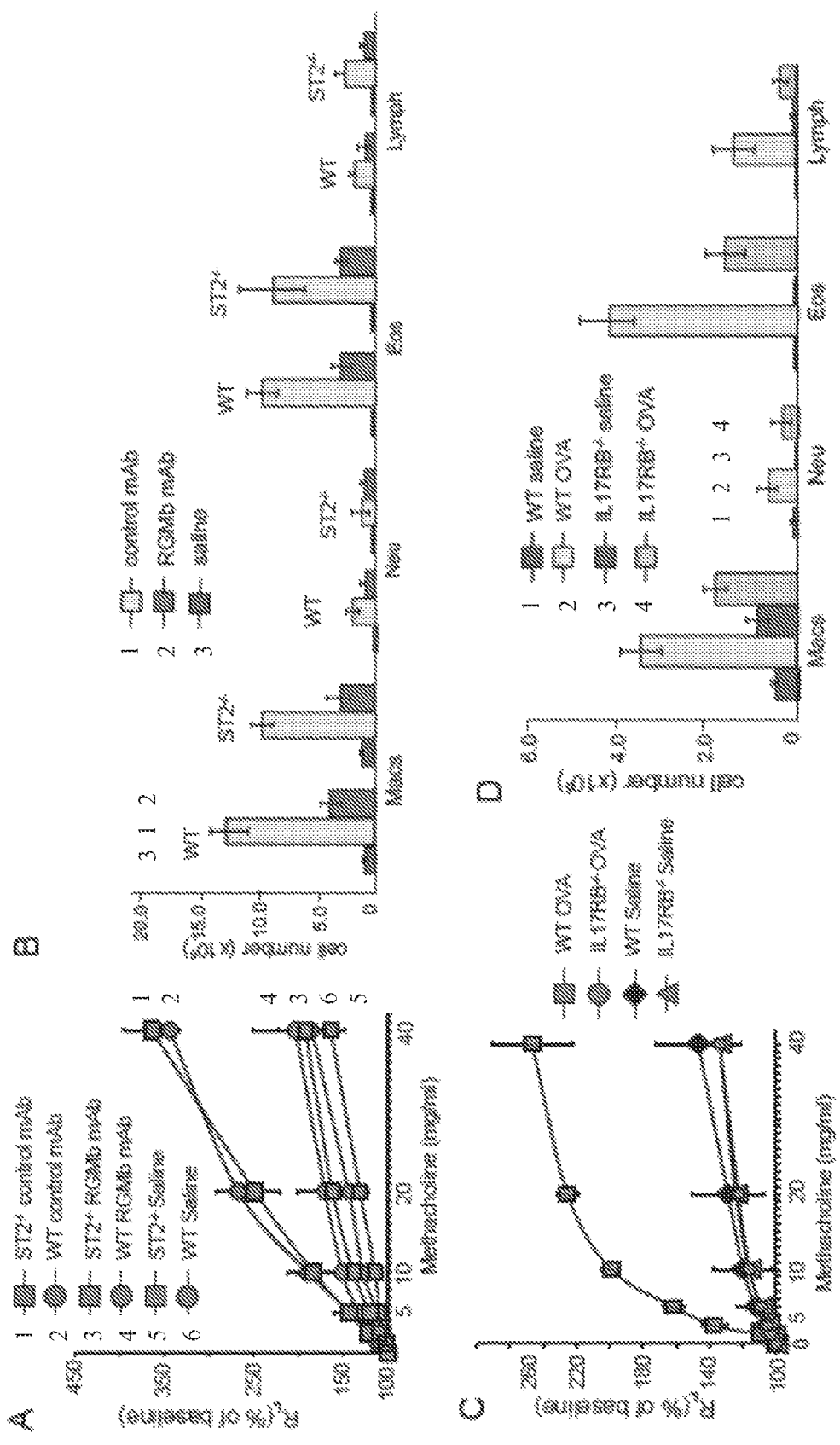
FIG. 7 includes four panels, identified as panels (A), (B), (C), and (D), which show that IL-25, but not IL-33, signaling is required for development of OVA-induced AHR. Panels A and C show the results of IL-17RB$^{-/-}$ (Panel A), ST2$^{-/-}$ (Panel C) or WT mice sensitized and challenged with OVA following the protocol in FIG. 4 were assessed for AHR on day 10. Panels B and D show the results of BAL fluid from the mice in Panels A and C analyzed following AHR measurement.

The epithelial cell-derived cytokines IL-25 (Fort et al. (2001) *Immunity* 15:985-995; Hurst et al. (2002) *J. Immunol.* 169:443-453) and IL-33 (Coyle et al. (1999) *J. Exp. Med* 190:895-902; Schmitz et al. (2005) *Immunity* 23:479-490) are potent type 2-inducing cytokines that have been implicated in the pathogenesis of airway inflammation. To elucidate possible pathways whereby RGMb might modulate lung inflammation, the importance of these cytokine pathways in the AHR model was examined by analyzing the response of IL-25 receptor deficient (IL-17RB$^{-/-}$) or IL-33 receptor (ST2$^{-/-}$) mice to OVA sensitization and challenge. ST2$^{-/-}$ mice sensitized and challenged with OVA developed similar levels of AHR and lung inflammation as wild type (WT) mice (FIGS. 7A-7B), indicating that IL-33 signaling is not required for allergen-induced lung inflammation in the AHR model. Treatment with RGMb mAb inhibited the development of AHR and lung inflammation in both the WT and ST2$^{-/-}$ mice. In contrast, IL-17RB$^{-/-}$ mice failed to develop AHR following OVA sensitization and challenge, while WT mice developed a robust AHR response (FIG. 7C). Lungs of WT mice had airway inflammation characterized by increased numbers of macrophages and eosinophils in the BAL fluid compared with saline challenged mice, while lungs of IL-17RB$^{-/-}$ had significantly reduced lung inflammation (FIG. 7D), indicating that IL-25 was required for the development of allergen-induced AHR.

Example 7: F4/80$^+$CD11b$^+$IL17RB$^+$ Cells Express RGMb

IL-25 promotes type 2 inflammation by inducing production of the type 2 cytokines IL-4, IL-5 and IL-13 following binding to its receptor IL17RB, a subunit of the heterodimeric IL-25 receptor that confers specificity for IL-25 (Rickel et al. (2008) *J. Immunol.* 181:4299-4310). IL17RB is expressed on ILC2 cells, a subset of iNKT cells, Th2 cells and a recently described CD11b$^+$GR1$^+$ myeloid cell population in the lung termed T2M. These T2M cells have been shown to expand in the lung following allergen challenge and exacerbate asthma pathology (Petersen et al. (2012) *Nat. Med.* 18:751-758). To determine which of these cell types was primarily responsible for the IL-25-induced pathology in the AHR model, the relative abundance of these cells in the lungs of OVA sensitized and challenged mice was determined. It was found that the most abundant cell types in the inflamed lung were CD4 T cells and F4/80+CD11b+ myeloid cells. ILC2 cells and iNKT cells were present in the lungs but in much lower numbers. An anti-IL17RB mAb that was generated as described herein was used to determine which cells expressed the IL-25 receptor (FIG. 2H). Approximately 25% of the F4/80+CD11b+ cells expressed IL-17RB, while only 1.5% of the CD4 T cells expressed the IL-17RB. Since IL-25 is required in this model, the results indicate the importance of the F4/80+CD11b+ myeloid cell in the AHR model.

Figure 8:
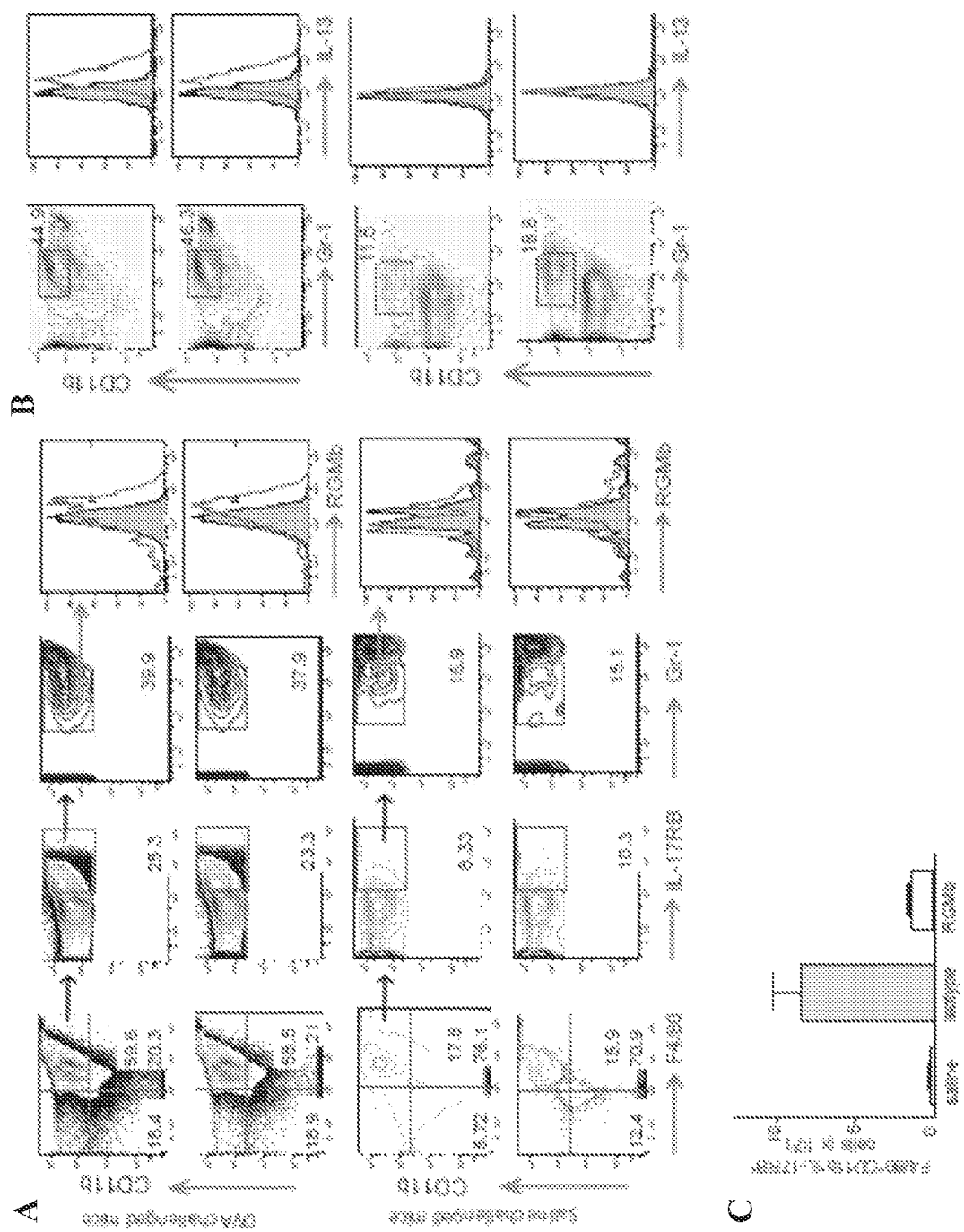
FIG. 8 includes three panels, identified as panels (A), (B), and (C), which show that F4/80$^+$ NEO$^+$ RGMb+ myeloid cells expand in the lung following allergen exposure, express the IL-25 receptor, and produce IL-13. Panels A and B show the results of lungs from mice challenged with OVA (upper sub-panel) or saline (lower sub-panel) were harvested, collagenase digested, and stained for IL17RB, F4/80, CD11b and Gr-1 expression. IL-17RB$^+$ myeloid cells were identified as IL-17RB$^+$ CD11b$^+$Gr-1$^{mid}$. Panel A shows the results of cells stained for expression of RGMb or isotype. Panel B shows the results of total lung cells cultured in the presence of Golgi stop for 6 hours. Cells were fixed, permeabilized, stained for IL-13 or isotype and analyzed by FACS. IL-17RB$^+$ myeloid cells were identified as in panel A and stained with RGMb or isotype. Numbers on the plots reflect the percentage of cells on each plot that are present within the gated area. Panel C shows the results of mice sensitized and challenged with OVA as in FIG. 4 treated with RGMb mAb or isotype control (500 μg) on days 0, 4 and 8 and the numbers of ILC2, iNKT, CD4 T and myeloid cells were determined in the lung on day 10 by flow cytometry.

A recently described myeloid population termed type 2 myeloid (T2M) cells, with the surface phenotype IL-17RB$^+$ F4/80$^+$CD11b$^+$Gr-1$^{mid}$, has been shown to exacerbate asthma pathology through production of IL-13 and IL-4. T2M cells in the lung of OVA sensitized and challenged mice were analyzed for RGMb expression by flow cytometry. It was found that RGMb was expressed on IL-17RB$^+$ F4/80$^+$CD11b$^+$Gr-1$^{mid}$ cells in lungs of mice sensitized and challenged with OVA, while little or no RGMB expression was seen in saline challenged mice (FIG. 8A). The IL-17RB$^+$F4/80$^+$CD11b$^+$Gr-1$^{mid}$ cells from inflamed lung produced IL-13, while those present in naïve lung did not produce IL-13 (FIG. 8B). Moreover, IL-17RB$^+$F4/80$^+$ CD11b$^+$Gr-1$^{mid}$ cells were present in much higher numbers in the lungs of OVA challenged mice than in the lungs of saline challenged mice.

To understand how treatment of mice with RGMb mAb inhibits the development of AHR, the numbers of T2M cells in lungs of RGMb and isotype treated mice were determined. It was found that the number of T2M cells were greatly reduced in RGMb treated compared with isotype treated mice (FIG. 8A), indicating that treatment with RGMb inhibits the expansion and/or accumulation of RGMb+T2M cells during exposure to allergen.

Example 8: RGMb Protein is Expressed by F4/80$^+$ CD11b$^+$ Cells in Lungs of Sensitized Mice To further characterize and visualize the cells expressing RGMb in the lungs of OVA sensitized and challenged mice, immunofluorescence microscopy experiments were performed. As expected from the flow cytometry data, RGMb was highly expressed on CD11b$^+$ F4/80$^+$ cells (FIG. 9A, left panel, overlay). Although some CD11b$^+$ cells that did not express F4/80 were observed (FIG. 9A, center panel), RGMb expression was only detected on cells that expressed both F4/80 and CD11b. RGMb was coexpressed with F4/80 (arrows) by most F4/80+ cells. Some F4/80$^+$ cells did not express RGMb (single arrow).

Example 9: Neogenin is Expressed by F4/80+CD11b+ Cells

Binding of RGMb to its receptor NEO has been shown to be critical in differentiation, including directing axonal migration and activating the BMP-regulated signaling pathway in bone morphogenesis. It was hypothesized that the effects of RGMb on development of AHR may involve RGMb binding to NEO in the lung. To determine where NEO was expressed in the lung, anti-NEO mAbs were generated that specifically stained cells transfected with murine neogenin but not control-transfected cells (FIG. 2H). It was found that NEO was expressed in the lung tissue of OVA sensitized and challenged mice (FIG. 9C, left panel), and NEO expression colocalized with expression of RGMb (FIG. 9C, second panel). Although F4/80+ cells were observed that did not express NEO, NEO$^+$ cells coexpressed F4/80 (FIG. 9C, third panel). Numerous cells were observed that coexpressed F4/80, NEO and RGMb (FIG. 9C, right panel), indicated by arrows. These findings indicate that RGMb binding to NEO expressed on the same cell or an adjacent cell may activate BMP signaling and orchestrate cytokine responses of the cell.

Figure 10:
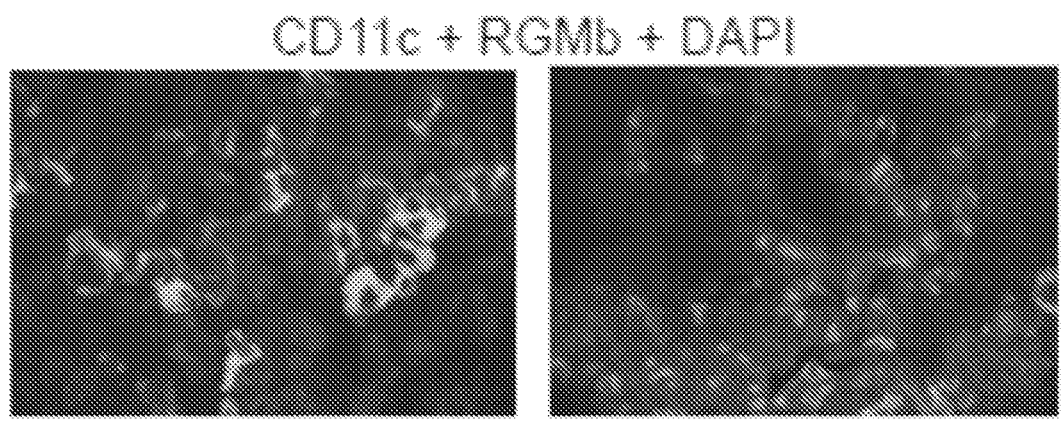
FIG. 10 shows that RGMb expression does not co-localize with CD11c. Lung sections were stained with anti-CD11c, anti-RGMb, and DAPI. The left image shows very few RGMb$^+$ cells in an optic field containing large numbers of CD11c$^+$ cells. The right image shows very few CD11c$^+$ cells and many RGMb cells in a different optic field of the same section as shown in the left image.

RGMb expression was not observed on CD11c$^+$ cells in the lung. Although RGMb expression was high in some areas of the lung, only a few cells in these areas expressed CD11c and these CD11c$^+$ cells did not express RGMb (FIG. 10). In contrast, CD11c expression was high in other sections of the lung. However, only a few cells that expressed RGMb were observed in these areas and these cells did not express CD11c (FIG. 10). This finding is consistent with previous studies of RGMb mRNA expression in naïve lung, which showed highest RGMb expression in F4/80$^+$CD11c$^-$ cells (Xiao et al. (2014) *J. Exp. Med* 211:943-959).

Example 10: RGMb+F4/80+ Cells are Located Adjacent to Lung Epithelial Cells

RGMb and NEO were expressed by IL-17RB$^+$F4/80$^+$ CD11b$^+$ cells with the surface phenotype of T2M cells. Since inflamed epithelial cells are a critical source of IL-25 responsible for driving the allergic airway response, the proximity of F4/80$^+$RGMb$^+$ cells to epithelial cells was analyzed, as identified by staining for cytokeratin in the lungs of mice sensitized and challenged with OVA. Numerous F4/80+ cells were localized directly adjacent to airway epithelial cells, as identified by staining with pan-cytokeratin mAb (FIG. 9D). RGMb was highly expressed on F4/80+ cells localized adjacent to epithelial cells (FIG. 9E, right panel). Cells expressing NEO were also observed in close proximity to epithelial cells, but NEO was not co-expressed by cells that expressed cytokeratin (FIG. 9F).

Based on the results described herein, a role for RGMb in the development of allergen-induced AHR has been determined. Treatment with RGMb mAb inhibited the development of AHR even when given after sensitization, prior to airway challenge of OVA-sensitized mice. RGMb mAb treatment did not affect priming of T cells. It has been demonstrated herein that RGMb is highly expressed in the lung on a recently characterized IL-17RB$^+$ myeloid cell termed T2M that accumulates in the lung following repeated allergen exposure, and produces IL-4 and IL-13 in response to IL-25 (Petersen et al. (2012) *Nat. Med.* 18:751-758). It is further demonstrated that RGMb-expressing cells also express NEO, a ligand of RGMb. Co-crystal studies show that a dimer of RGMb can join two molecules of NEO. The RGMb-expressing cells are located adjacent to cytokeratin$^+$ epithelial cells, which have been shown to be a critical source of IL-25 responsible for airway inflammation (Suzukawa et al. (2012) *J. Immunol.* 189:3641-3652). These results indicate that RGMb and NEO expressed on T2M cells in inflamed lung form a signaling hub that modulates the response of these cells. These studies are important because they describe a novel pathway that regulates the development of AHR, a cardinal feature of allergic asthma.

IL-25 has been shown to play a key role as a mediator of type 2 immunity in allergen-driven AHR (Ballantyne et al. (2007) *J. Allerg. Clin. Immunol.* 120:1324-1331; Rickel et al. (2008) *J. Immunol.* 181:4299-4310). Our mouse model of allergen-driven AHR is dependent on IL-25, since mice deficient in IL-17RB (the receptor for IL-25) did not develop AHR when immunized and challenged with OVA. IL-25 acts upstream of IL-5 and IL-13, since administration of IL-13 in vivo induces type 2 cytokine production with accompanying inflammation (Rickel et al. (2008) *J. Immunol.* 181:4299-4310; Fort et al. (2001) *Immunity* 15:985-995). Blocking IL-25 with IL-25 mAb prevents AHR even if given in the challenge phase. In our model, treatment with RGMb mAb also inhibits AHR when given in the challenge phase, suggesting that it controls the response to IL-25 of the IL-13-producing myeloid cell.

RGMb, a GPI anchored protein, is a member of the RGM family of membrane proteins that do not signal directly but act as co-receptors that modulate the activity of signaling receptors. RGMb has been shown to bind NEO (Bell et al. (2013) *Science* 341:77-80; Conrad et al. (2009) *Mol. Cell Neurosci.* 43:222-231). Neogenin (NEO1), a critical receptor for axonal guidance and endochondral bone formation during embryonic development (Zhou et al. (2010) *Dev. Cell* 19:90-102, Cole et al. (2007) *Int. J. Biochem. Cell Biol.* 39:1569-1575), is abundantly expressed outside the nervous system, and has been associated with pulmonary inflammation during lung injury (Mirakaj et al. (2012) *FASEB J.* 26:1549-1558). Recent elucidation of the RGMb crystal structure showed that two RGMB ectodomains conformationally stabilize two NEO1 receptors, and this structure forms a "hub" that represents the core of multiple signaling pathways. It was found that RGMb and NEO are both expressed on T2M cells, indicating that they may interact in cis orientation. However, RGMb+NEO+ cells were often observed in groups, indicating a trans interaction between two such cells is also possible.

RGMb-NEO interaction in the lung could signal directly or could also involve activation of BMP signaling pathways. The co-crystal structure suggests that RGMb-NEO forms a signaling "hub" in which BMP proteins or other ligands of NEO or RGMb could participate (Bell et al. (2013) *Science* 341:77-80). In support of this notion, RGM binding to NEO has been shown to activate the BMP-regulated signaling involved in bone morphogenesis (Zhou et al. (2010) *Dev. Cell* 19:90-102) and iron homeostasis (Zhang et al. (2007) *J. Biol. Chem.* 282:12547-12556). RGMb binds BMP2 and BMP4 (Samad et al. (2005) *J. Biol. Chem.* 280:14122-14129; Xia et al. (2010). *J. Am. Soc. Nephrol.* 21:666-677). Induction of BMP 2, 4 and 6 and activation of BMP/Smad signaling was observed in bronchial epithelial cells during allergic airway inflammation (Rosendahl et al. (2002) *Am. J. Respir. Cell Mol. Biol.* 27:160-169).

While it was recently demonstrated that RGMb binds PD-L2 and the interaction of PD-L2 and RGMb promotes respiratory tolerance (Xiao et al. (2014) *J. Exp. Med.* 211: 943-959), it is demonstrated herein that RGMb modulates the development of allergen-driven AHR is independent of PD-L2. Treatment with a PD-L2 mAb that blocks the interaction of PD-L2 with RGMb had no effect on development of AHR. Moreover. RGMb mAb blocked the development of AHR in PD-L2 deficient mice, further demonstrating that an RGMb:PD-L2 interaction is not involved.

What is claimed is:

1. A method of treating a subject, having a respiratory inflammatory disorder comprising administering to the subject a therapeutically effective amount of an anti-RGMb blocking monoclonal antibody, or antigen-binding fragment thereof, that inhibits the repulsive guidance molecule b (RGMb)-neogenin (NEO1)-bone morphogenetic protein (BMP) signaling pathway to thereby treat the respiratory inflammatory disorder, wherein the respiratory inflammatory disorder is respiratory allergy, chronic obstructive pulmonary disease (COPD), emphysema, chronic bronchitis, chronic sinusitis, or cystic fibrosis, and further wherein the anti-RGMb blocking monoclonal antibody, or antigen-binding fragment thereof, comprises a) a heavy chain variable sequence comprising complementarity-determining regions (CDR)-H1, CDR-H2, and CDR-H3 amino acid sequences that are those encoded by nucleotides 148-162, 205-255, and 352-375, respectively, of SEQ ID NO: 28, and b) a light chain variable sequence comprising CDR-L1, CDR-L2, and CDR-L3 amino acid sequences that are those encoded by nucleotides 130-162, 208-228, and 325-348, respectively, of SEQ ID NO: 26.

2. The method of claim 1, wherein the anti-RGMb blocking monoclonal antibody, or antigen-binding fragment thereof, comprises a) a heavy chain variable sequence of SEQ ID NO: 27, and b) a light chain variable sequence of SEQ ID NO: 25.

3. The method of claim 1, wherein said anti-RGMb blocking monoclonal antibody, or antigen binding fragment thereof, is murine, chimeric, humanized, composite, or human.

4. The method of claim 1, wherein said anti-RGMb blocking monoclonal antibody, or antigen binding fragment thereof, is detectably labeled.

5. The method of claim 1, wherein said anti-RGMb blocking monoclonal antibody, or antigen binding fragment thereof, comprises an effector domain.

6. The method of claim 1, wherein said anti-RGMb blocking monoclonal antibody, or antigen binding fragment thereof, comprises an Fc domain.

7. The method of claim 1, wherein said anti-RGMb blocking monoclonal antibody, or antigen binding fragment thereof, is selected from the group consisting of Fv, Fav, F(ab')2), Fab', dsFv, scFv, sc(Fv)2, and diabodies fragments.

8. The method of claim 1, wherein said anti-RGMb blocking monoclonal antibody, or antigen binding fragment thereof, is conjugated to a heterologous agent.

9. The method of claim 8, wherein the heterologous agent is selected from the group consisting of a biologic agent, a toxin, and a radioactive isotope.

10. The method of claim 1, wherein said anti-RGMb blocking monoclonal antibody, or antigen binding fragment thereof, is administered in a pharmaceutically acceptable formulation.

11. The method of claim 1, further comprising administering to the subject an additional therapeutic agent for treating the respiratory inflammatory disorder.

12. The method of claim 11, wherein the additional therapeutic is selected from the group consisting of bronchodilators, corticosteroids, glucocorticoids, mast-cell stabilizers, oxygen, cytokine inhibitors, immunomodulatory inhibitors, and leukotriene inhibitors, anticholinergic agents, antihistamines, and IgE inhibitors.

13. The method of claim 1, wherein said anti-RGMb blocking monoclonal antibody, or antigen binding fragment thereof, wherein said at least one agent is administered systemically, orally, nasally, or pulmonarily.

14. The method of claim 1, wherein said subject is a mammal.

15. The method of claim 14, wherein the mammal is an animal model of the respiratory inflammatory disorder or is a human.

16. The method of claim 15, wherein the subject has an observable reduction in or absence of one or more of the following: acute hyperreactivity (AHR), recurrent wheezing, coughing, trouble breathing, chest tightness, symptoms that occur or worsen at night, symptoms that are triggered by cold air, exercise or exposure to allergens, upregulated serum IgE (atopy), eosinophilia, and excessive mucus secretion.

* * * * *

SEQUENCE LISTING

```
<160> NUMBER OF SEQ ID NOS: 28

<210> SEQ ID NO 1
<211> LENGTH: 1437
<212> TYPE: DNA
<213> ORGANISM: Homo sapiens

<400> SEQUENCE: 1
atgataagga agaagaggaa gcgaagcgcg ccccccggcc catgccgcag ccacgggccc      60 agaccccgcca cggcgcccgc gccgccgccc tcgccggagc ccacgagacc tgcatggacg     120
ggcatgggct tgagagcagc accttccagc gccgccgctg ccgccgccga ggttgagcag     180
cgccgcagcc ccgggctctg ccccccgccg ctggagctgc tgctgctgct gctgttcagc     240
ctcgggctgc tccacgcagg tgactgccaa cagccagccc aatgtcgaat ccagaaatgc     300
accacggact tcgtgtccct gacttctcac ctgaactctg ccgttgacgg ctttgactct     360
gagttttgca aggccttgcg tgcctatgct ggctgcaccc agcgaacttc aaaagcctgc     420
cgtggcaacc tggtatacca ttctgccgtg ttgggtatca gtgacctcat gagccagagg     480
aattgttcca aggatggacc cacatcctct accaacccccg aagtgaccca tgatccttgc     540
aactatcaca gccacgctgg agccagggaa cacaggagag gggaccagaa ccctcccagt     600 taccttttt gtggcttgtt tggagatcct cacctcagaa ctttcaagga taacttccaa     660
acatgcaaag tagaagggc ctggccactc atagataata attatctttc agttcaagtg     720
acaaacgtac ctgtggtccc tggatccagt gctactgcta caaataagat cactattatc     780
ttcaaagccc accatgagtg tacagatcag aaagtctacc aagctgtgac agatgacctg     840
ccggccgcct ttgtggatgg caccaccagt ggtggggaca gcgatgccaa gagcctgcgt     900
atcgtggaaa gggagagtgg ccactatgtg gagatgcacg cccgctatat agggaccaca     960
gtgtttgtgc ggcaggtggg tcgctacctg accccttgcca tccgtatgcc tgaagacctg    1020
```

```
gccatgtcct acgaggagag ccaggacctg cagctgtgcg tgaacggctg ccccctgagt    1080
gaacgcatcg atgacgggca gggccaggtg tctgccatcc tgggacacag cctgcctcgc    1140
acctccttgg tgcaggcctg gcctggctac acactggaga ctgccaacac tcaatgccat    1200
gagaagatgc cagtgaagga catctatttc cagtcctgtg tcttcgacct gctcaccact    1260
ggtgatgcca actttactgc cgcagcccac agtgccttgg aggatgtgga ggccctgcac    1320
ccaaggaagg aacgctggca cattttcccc agcagtggca atgggactcc ccgtggaggc    1380
agtgatttgt ctgtcagtct aggactcacc tgcttgatcc ttatcgtgtt tttgtag       1437
```

<210> SEQ ID NO 2
<211> LENGTH: 478
<212> TYPE: PRT
<213> ORGANISM: Homo sapiens

<400> SEQUENCE: 2

```
Met Ile Arg Lys Lys Arg Lys Ser Ala Pro Pro Gly Pro Cys Arg
1               5                   10                  15

Ser His Gly Pro Arg Pro Ala Thr Ala Pro Ala Pro Pro Ser Pro
                20                  25                  30

Glu Pro Thr Arg Pro Ala Trp Thr Gly Met Gly Leu Arg Ala Pro
                35                  40                  45

Ser Ser Ala Ala Ala Ala Ala Glu Val Glu Gln Arg Arg Ser Pro
    50                  55                  60

Gly Leu Cys Pro Pro Leu Glu Leu Leu Leu Leu Leu Leu Phe Ser
65                  70                  75                  80

Leu Gly Leu Leu His Ala Gly Asp Cys Gln Gln Pro Ala Gln Cys Arg
                85                  90                  95

Ile Gln Lys Cys Thr Thr Asp Phe Val Ser Leu Thr Ser His Leu Asn
                100                 105                 110

Ser Ala Val Asp Gly Phe Asp Ser Glu Phe Cys Lys Ala Leu Arg Ala
                115                 120                 125

Tyr Ala Gly Cys Thr Gln Arg Thr Ser Lys Ala Cys Arg Gly Asn Leu
                130                 135                 140

Val Tyr His Ser Ala Val Leu Gly Ile Ser Asp Leu Met Ser Gln Arg
145                 150                 155                 160

Asn Cys Ser Lys Asp Gly Pro Thr Ser Ser Thr Asn Pro Glu Val Thr
                165                 170                 175

His Asp Pro Cys Asn Tyr His Ser His Ala Gly Ala Arg Glu His Arg
                180                 185                 190

Arg Gly Asp Gln Asn Pro Pro Ser Tyr Leu Phe Cys Gly Leu Phe Gly
                195                 200                 205

Asp Pro His Leu Arg Thr Phe Lys Asp Asn Phe Gln Thr Cys Lys Val
                210                 215                 220

Glu Gly Ala Trp Pro Leu Ile Asp Asn Asn Tyr Leu Ser Val Gln Val
225                 230                 235                 240

Thr Asn Val Pro Val Val Pro Gly Ser Ser Ala Thr Ala Thr Asn Lys
                245                 250                 255

Ile Thr Ile Ile Phe Lys Ala His His Glu Cys Thr Asp Gln Lys Val
                260                 265                 270

Tyr Gln Ala Val Thr Asp Asp Leu Pro Ala Ala Phe Val Asp Gly Thr
                275                 280                 285

Thr Ser Gly Gly Asp Ser Asp Ala Lys Ser Leu Arg Ile Val Glu Arg
                290                 295                 300
```

```
Glu Ser Gly His Tyr Val Glu Met His Ala Arg Tyr Ile Gly Thr Thr
305                 310                 315                 320

Val Phe Val Arg Gln Val Gly Arg Tyr Leu Thr Leu Ala Ile Arg Met
            325                 330                 335

Pro Glu Asp Leu Ala Met Ser Tyr Glu Ser Gln Asp Leu Gln Leu
        340                 345                 350

Cys Val Asn Gly Cys Pro Leu Ser Glu Arg Ile Asp Asp Gly Gln Gly
        355                 360                 365

Gln Val Ser Ala Ile Leu Gly His Ser Leu Pro Arg Thr Ser Leu Val
    370                 375                 380

Gln Ala Trp Pro Gly Tyr Thr Leu Glu Thr Ala Asn Thr Gln Cys His
385                 390                 395                 400

Glu Lys Met Pro Val Lys Asp Ile Tyr Phe Gln Ser Cys Val Phe Asp
            405                 410                 415

Leu Leu Thr Thr Gly Asp Ala Asn Phe Thr Ala Ala His Ser Ala
        420                 425                 430

Leu Glu Asp Val Glu Ala Leu His Pro Arg Lys Glu Arg Trp His Ile
        435                 440                 445

Phe Pro Ser Ser Gly Asn Gly Thr Pro Arg Gly Gly Ser Asp Leu Ser
    450                 455                 460

Val Ser Leu Gly Leu Thr Cys Leu Ile Leu Ile Val Phe Leu
465                 470                 475

<210> SEQ ID NO 3
<211> LENGTH: 1311
<212> TYPE: DNA
<213> ORGANISM: Mus musculus

<400> SEQUENCE: 3
atgggcgtga gagcagcacc ttcctgcgcc gccgccccg ccgccgccgg ggctgagcag      60
tcccgccgcc ccgggctctg gccgccgtcg ccccgccgc cgctgttgct gctgctgctg     120
ctcagccttg gctgctcca cgcaggtgat gccaacagc ctactcaatg ccgaatccag     180
aaatgtacca cagacttcgt ggccctgact gcacacctga actctgccgc tgatgggttt     240
gactctgagt tttgcaaggc acttcgcgcc tatgctggct gcacccagcg aacttcaaag     300
gcctgccgag caacctggt gtaccattct gctgtgttag catcagtga tctcatgagc     360 cagaggaact gttccaagga tggacccaca tcttccacca atccggaagt gacccatgac     420
ccctgtaact accacagcca cgggggagtc agagaacatg ggggagggga ccagagacct     480
cccaattacc tttctgtgg cttgtttgga gaccctcacc ttcgaacttt caaggatcac     540
ttccagacat gcaaagtgga aggggcctgg ccactcatag acaacaatta cctttcggtt     600
caagtgacga acgtgcctgt ggtccccggg tccagtgcaa ctgctacaaa caaggtcacg     660
attatcttca agcacagca cgagtgcacg atcagaagg tgtaccaagc tgtgacagat     720
gacctgccgg ccgcctttgt agatggcacc accagtgggg gggacggtga cgtgaagagt     780
cttcacatcg tggagaagga gagtggccgc tacgtagaga tgcatgcccg ctacataggc     840
accacagtgt ttgtgcgaca gctgggtcgc tacctaaccc tcgctatccg gatgccgaa     900 gacttggcca tgtcctatga ggaaagccag gacttgcagc tgtgtgtgaa tggctgcccc     960
atgagtgaat gcattgatga tggacaaggc caggtgtctg ctatcctggg cacagcctg    1020 cctcacacca cctcagtgca ggcctggcct ggctacacac tggagactgc cagcacccaa    1080
tgccacgaga agatgccggt gaaggacatc tatttccaat cgtgtgtctt cgacctgctc    1140
```

-continued

```
accactggtg atgccaactt tactgctgca gcccacagtg ccttggagga tgtggaagcg   1200
ctgcacccaa gaaaggaacg ctggcacatc ttccccagca gctgtggggg atgtagggat   1260
ttgcctgttg gtcttggact cacatgcttg atccttatta tgttttgta g              1311
```

<210> SEQ ID NO 4
<211> LENGTH: 436
<212> TYPE: PRT
<213> ORGANISM: Mus musculus

<400> SEQUENCE: 4

```
Met Gly Val Arg Ala Ala Pro Ser Cys Ala Ala Pro Ala Ala Ala
1               5                   10                  15

Gly Ala Glu Gln Ser Arg Arg Pro Gly Leu Trp Pro Pro Ser Pro Pro
            20                  25                  30

Pro Pro Leu Leu Leu Leu Leu Leu Ser Leu Gly Leu Leu His Ala
        35                  40                  45

Gly Asp Cys Gln Gln Pro Thr Gln Cys Arg Ile Gln Lys Cys Thr Thr
50                  55                  60

Asp Phe Val Ala Leu Thr Ala His Leu Asn Ser Ala Ala Asp Gly Phe
65                  70                  75                  80

Asp Ser Glu Phe Cys Lys Ala Leu Arg Ala Tyr Ala Gly Cys Thr Gln
                85                  90                  95

Arg Thr Ser Lys Ala Cys Arg Gly Asn Leu Val Tyr His Ser Ala Val
            100                 105                 110

Leu Gly Ile Ser Asp Leu Met Ser Gln Arg Asn Cys Ser Lys Asp Gly
        115                 120                 125

Pro Thr Ser Ser Thr Asn Pro Glu Val Thr His Asp Pro Cys Asn Tyr
130                 135                 140

His Ser His Gly Gly Val Arg Glu His Gly Gly Asp Gln Arg Pro
145                 150                 155                 160

Pro Asn Tyr Leu Phe Cys Gly Leu Phe Gly Asp Pro His Leu Arg Thr
                165                 170                 175

Phe Lys Asp His Phe Gln Thr Cys Lys Val Glu Gly Ala Trp Pro Leu
            180                 185                 190

Ile Asp Asn Asn Tyr Leu Ser Val Gln Val Thr Asn Val Pro Val Val
        195                 200                 205

Pro Gly Ser Ser Ala Thr Ala Thr Asn Lys Val Thr Ile Ile Phe Lys
210                 215                 220

Ala Gln His Glu Cys Thr Asp Gln Lys Val Tyr Gln Ala Val Thr Asp
225                 230                 235                 240

Asp Leu Pro Ala Ala Phe Val Asp Gly Thr Thr Ser Gly Gly Asp Gly
                245                 250                 255

Asp Val Lys Ser Leu His Ile Val Glu Lys Glu Ser Gly Arg Tyr Val
            260                 265                 270

Glu Met His Ala Arg Tyr Ile Gly Thr Thr Val Phe Val Arg Gln Leu
        275                 280                 285

Gly Arg Tyr Leu Thr Leu Ala Ile Arg Met Pro Glu Asp Leu Ala Met
290                 295                 300

Ser Tyr Glu Glu Ser Gln Asp Leu Gln Leu Cys Val Asn Gly Cys Pro
305                 310                 315                 320

Met Ser Glu Cys Ile Asp Asp Gly Gln Gly Gln Val Ser Ala Ile Leu
                325                 330                 335

Gly His Ser Leu Pro His Thr Thr Ser Val Gln Ala Trp Pro Gly Tyr
```

```
                340              345                 350
Thr Leu Glu Thr Ala Ser Thr Gln Cys His Glu Lys Met Pro Val Lys
            355                 360                 365

Asp Ile Tyr Phe Gln Ser Cys Val Phe Asp Leu Leu Thr Thr Gly Asp
            370                 375                 380

Ala Asn Phe Thr Ala Ala His Ser Ala Leu Glu Asp Val Glu Ala
385                 390                 395                 400

Leu His Pro Arg Lys Glu Arg Trp His Ile Phe Pro Ser Ser Cys Gly
            405                 410                 415

Gly Cys Arg Asp Leu Pro Val Gly Leu Gly Leu Thr Cys Leu Ile Leu
            420                 425                 430

Ile Met Phe Leu
            435

<210> SEQ ID NO 5
<211> LENGTH: 4386
<212> TYPE: DNA
<213> ORGANISM: Homo sapiens

<400> SEQUENCE: 5
atggcggcgg agcggggagc ccggcgactc ctcagcaccc cctccttctg gctctactgc      60
ctgctgctgc tcgggcgccg ggcgccgggc gccgcggccg ccaggagcgg ctccgcgccg     120
cagtccccag gagccagcat tcgaacgttc actccatttt attttctggt ggagccggtg     180
gatacactct cagttagagg ctcttctgtt atattaaact gttcagcata ttctgagcct     240
tctccaaaaa ttgaatggaa aaagatgga acttttttaa acttagtatc agatgatcga     300
cgccagcttc tcccggatgg atctttattt atcagcaatg tggtgcattc caaacacaat     360
aaacctgatg aaggttatta tcagtgtgtg ccactgttg agagtcttgg aactattatc     420
agtagaacag cgaagctcat agtagcaggt cttccaagat ttaccagcca accagaacct     480
tcctcagttt atgctgggaa caatgcaatt ctgaattgtg aagttaatgc agatttggtc     540
ccatttgtga ggtgggaaca gaacagacaa cccttcttc tggatgatag agttatcaaa     600
cttccaagtg gaatgctggt tatcagcaat gcaactgaag gagatggcgg gctttatcgc     660
tgcgtagtgg aaagtggtgg gccaccaaag tatagtgatg aagttgaatt gaaggttctt     720
ccagatcctg aggtgatatc agacttggta tttttgaaac agccttctcc cttagtcaga     780
gtcattggtc aggatgtagt gttgccatgt gttgcttcag acttcctac tccaaccatt     840 aaatggatga aaatgagga ggcacttgac acagaaagct ctgaaagatt ggtattgctg     900
gcaggtggta gcctggagat cagtgatgtt actgaggatg atgctgggac ttattttgt     960 atagctgata tggaaatga gacaattgaa gctcaagcag agcttacagt gcaagctcaa    1020
cctgaattcc tgaagcagcc tactaatata tatgctcacg aatctatgga tattgtattt    1080
gaatgtgaag tgactggaaa accaactcca actgtgaagt gggtcaaaaa tgggatatg    1140 gttatcccaa gtgattattt taagattgta aaggaacata atcttcaagt tttgggtctg    1200
gtgaaatcag atgaagggtt ctatcagtgc attgctgaaa atgatgttgg aaatgcacaa    1260
gctggagccc aactgataat ccttgaacat gcaccagcca aacgggacc actgccttca    1320 gctcctcggg atgtcgtggc ctccctggtc tctacccgct tcatcaaatt gacgtggcgg    1380
acacctgcat cagatcctca cggagacaac cttacctact ctgtgttcta caccaaggaa    1440
gggattgcta gggaacgtgt tgagaatacc agtcacccag agagatgca agtaaccatt    1500 caaaacctaa tgccagcgac cgtgtacatc tttagagtta tggctcaaaa taagcatggc    1560
```

```
tcaggagaga gttcagctcc actgcgagta gaaacacaac ctgaggttca gctccctggc     1620
ccagcaccta accttcgtgc atatgcagct tcgcctacct ccatcactgt tacgtgggaa     1680
acaccagtgt ctggcaatgg ggaaattcag aattataaat tgtactacat ggaaaagggg    1740
actgataaag aacaggatgt tgatgtttca agtcactctt acaccattaa tgggttgaaa    1800
aaatatacag agtatagttt ccgagtggtg gcctacaata acatggtcc tggagtttcc     1860 acaccagatg ttgctgttcg aacattgtca gatgttccca gtgctgctcc tcagaatctg    1920
tccttggaag tgagaaattc aaagagtatt atgattcact ggcagccacc tgctccagcc    1980
acacaaaatg gcagattac tggctacaag attcgctacc gaaaggcctc ccgaaagagt     2040
gatgtcactg agaccttggt aagcgggaca cagctgtctc agctgattga aggtcttgat    2100
cgggggactg agtataattt ccgagtggct gctctaacaa tcaatggtac aggcccggca    2160
actgactggc tgtctgctga aacttttgaa agtgacctag atgaaactcg tgttcctgaa    2220
gtgcctagct ctcttcacgt acgcccgctc gttactagca tcgtagtgag ctggactcct    2280
ccagagaatc agaacattgt ggtcagaggt tacgccattg gttatggcat ggcagccct    2340 catgcccaga ccatcaaagt ggactataaa cagcgctatt acaccattga aaatctggat    2400
cccagctctc actatgtgat taccctgaaa gcatttaata acgtgggtga aggcatcccc    2460
ctgtatgaga gtgctgtgac caggcctcac acagacactt ctgaagttga tttatttgtt    2520
attaatgctc catacactcc agtgccagat cccactccca tgatgccacc agtgggagtt    2580
caggcttcca ttctgagtca tgacaccatc aggattacgt gggcagacaa ctcgctgccc    2640
aagcaccaga agattacaga ctcccgatac tacaccgtcc gatggaaaac caacatccca    2700
gcaaacacca gtacaagaa tgcaaatgca accactttga gttatttggt gactggttta    2760
aagccgaata cactctatga attctctgtg atggtgacca aaggtcgaag atcaagtaca    2820
tggagtatga cagcccatgg gaccacccttt gaattagttc cgacttctcc acccaaggat    2880
gtgactgttg tgagtaaaga ggggaaacct aagaccataa ttgtgaattg gcagcctccc    2940
tccgaagcca atggcaaaat tacaggttac atcatatatt acagtacaga tgtgaatgca    3000
gagatacatg actgggttat tgagcctgtt gtgggaaaca gactgactca ccagatacaa    3060
gagttaactc ttgacacacc atactacttc aaaatccagg cacggaactc aaagggcatg    3120
ggacccatgt ctgaagctgt ccaattcaga acacctaaag cggactcctc tgataaaatg    3180
cctaatgatc aagcctcagg gtctggaggg aaaggaagcc ggctgccaga cctaggatcc    3240
gactacaaac ctccaatgag cggcagtaac agccctcatg ggagcccac ctctcctctg     3300 gacagtaata tgctgctggt cataattgtt tctgttggcg tcatcaccat cgtggtggtt    3360
gtgattatcg ctgtcttttg tacccgtcgt accacctctc accagaaaaa gaaacgagct    3420
gcctgcaaat cagtgaatgg ctctcataag tacaaaggga attccaaaga tgtgaaacct    3480
ccagatctct ggatccatca tgagagactg gagctgaaac ccattgataa gtctccagac    3540
ccaaacccca tcatgactga tactccaatt cctcgcaact ctcaagatat cacaccagtt    3600
gacaactcca tggacagcaa tatccatcaa aggcgaaatt catacagagg gcatgagtca    3660
gaggacagca tgtctacact ggctggaagg cgaggaatga ccaaaaaat gatgatgccc    3720 tttgactccc agccacccca gcctgtgatt agtgcccatc ccatccattc cctcgataac    3780
cctcaccatc atttccactc cagcagcctc gcttctccag ctcgcagtca tctctaccac    3840
ccgggcagcc catggcccat tggcacatcc atgtcccttt cagacagggc caattccaca    3900
```

-continued

```
gaatccgttc gaaataccec cagcactgac accatgccag cctcttcgtc tcaaacatgc    3960
tgcactgatc accaggaccc tgaaggtgct accagctcct cttacttggc cagctcccaa    4020
gaggaagatt caggccagag tcttcccact gcccatgttc gcccttccca cccattgaag    4080
agcttcgccg tgccagcaat cccgcctcca ggacctccca cctatgatcc tgcattgcca    4140
agcacaccat tactgtccca gcaagctctg aaccatcaca ttcactcagt gaagacagcc    4200
tccatcggga ctctaggaag gagccggcct cctatgccag tggttgttcc cagtgccct    4260 gaagtgcagg agaccacaag gatgttggaa gactccgaga gtagctatga accagatgag    4320
ctgaccaaag agatggccca cctggaagga ctaatgaagg acctaaacgc tatcacaaca    4380
gcatga                                                                4386
```

<210> SEQ ID NO 6
<211> LENGTH: 1461
<212> TYPE: PRT
<213> ORGANISM: Homo sapiens

<400> SEQUENCE: 6

```
Met Ala Ala Glu Arg Gly Ala Arg Arg Leu Leu Ser Thr Pro Ser Phe
1               5                   10                  15

Trp Leu Tyr Cys Leu Leu Leu Gly Arg Arg Ala Pro Gly Ala Ala
            20                  25                  30

Ala Ala Arg Ser Gly Ser Ala Pro Gln Ser Pro Gly Ala Ser Ile Arg
        35                  40                  45

Thr Phe Thr Pro Phe Tyr Phe Leu Val Glu Pro Val Asp Thr Leu Ser
    50                  55                  60

Val Arg Gly Ser Ser Val Ile Leu Asn Cys Ser Ala Tyr Ser Glu Pro
65                  70                  75                  80

Ser Pro Lys Ile Glu Trp Lys Lys Asp Gly Thr Phe Leu Asn Leu Val
                85                  90                  95

Ser Asp Asp Arg Arg Gln Leu Leu Pro Asp Gly Ser Leu Phe Ile Ser
            100                 105                 110

Asn Val Val His Ser Lys His Asn Lys Pro Asp Glu Gly Tyr Tyr Gln
        115                 120                 125

Cys Val Ala Thr Val Glu Ser Leu Gly Thr Ile Ile Ser Arg Thr Ala
    130                 135                 140

Lys Leu Ile Val Ala Gly Leu Pro Arg Phe Thr Ser Gln Pro Glu Pro
145                 150                 155                 160

Ser Ser Val Tyr Ala Gly Asn Asn Ala Ile Leu Asn Cys Glu Val Asn
                165                 170                 175

Ala Asp Leu Val Pro Phe Val Arg Trp Glu Gln Asn Arg Gln Pro Leu
            180                 185                 190

Leu Leu Asp Asp Arg Val Ile Lys Leu Pro Ser Gly Met Leu Val Ile
        195                 200                 205

Ser Asn Ala Thr Glu Gly Asp Gly Gly Leu Tyr Arg Cys Val Val Glu
    210                 215                 220

Ser Gly Gly Pro Pro Lys Tyr Ser Asp Glu Val Glu Leu Lys Val Leu
225                 230                 235                 240

Pro Asp Pro Glu Val Ile Ser Asp Leu Val Phe Leu Lys Gln Pro Ser
                245                 250                 255

Pro Leu Val Arg Val Ile Gly Gln Asp Val Leu Pro Cys Val Ala
            260                 265                 270

Ser Gly Leu Pro Thr Pro Thr Ile Lys Trp Met Lys Asn Glu Glu Ala
    275                 280                 285
```

```
Leu Asp Thr Glu Ser Ser Glu Arg Leu Val Leu Ala Gly Gly Ser
    290                 295                 300

Leu Glu Ile Ser Asp Val Thr Glu Asp Ala Gly Thr Tyr Phe Cys
305                 310                 315                 320

Ile Ala Asp Asn Gly Asn Glu Thr Ile Glu Ala Gln Ala Glu Leu Thr
                325                 330                 335

Val Gln Ala Gln Pro Glu Phe Leu Lys Gln Pro Thr Asn Ile Tyr Ala
            340                 345                 350

His Glu Ser Met Asp Ile Val Phe Glu Cys Glu Val Thr Gly Lys Pro
        355                 360                 365

Thr Pro Thr Val Lys Trp Val Lys Asn Gly Asp Met Val Ile Pro Ser
370                 375                 380

Asp Tyr Phe Lys Ile Val Lys Glu His Asn Leu Gln Val Leu Gly Leu
385                 390                 395                 400

Val Lys Ser Asp Glu Gly Phe Tyr Gln Cys Ile Ala Glu Asn Asp Val
                405                 410                 415

Gly Asn Ala Gln Ala Gly Ala Gln Leu Ile Ile Leu Glu His Ala Pro
            420                 425                 430

Ala Thr Thr Gly Pro Leu Pro Ser Ala Pro Arg Asp Val Val Ala Ser
        435                 440                 445

Leu Val Ser Thr Arg Phe Ile Lys Leu Thr Trp Arg Thr Pro Ala Ser
450                 455                 460

Asp Pro His Gly Asp Asn Leu Thr Tyr Ser Val Phe Tyr Thr Lys Glu
465                 470                 475                 480

Gly Ile Ala Arg Glu Arg Val Glu Asn Thr Ser His Pro Gly Glu Met
                485                 490                 495

Gln Val Thr Ile Gln Asn Leu Met Pro Ala Thr Val Tyr Ile Phe Arg
            500                 505                 510

Val Met Ala Gln Asn Lys His Gly Ser Gly Glu Ser Ser Ala Pro Leu
        515                 520                 525

Arg Val Glu Thr Gln Pro Glu Val Gln Leu Pro Gly Pro Ala Pro Asn
530                 535                 540

Leu Arg Ala Tyr Ala Ala Ser Pro Thr Ser Ile Thr Val Thr Trp Glu
545                 550                 555                 560

Thr Pro Val Ser Gly Asn Gly Glu Ile Gln Asn Tyr Lys Leu Tyr Tyr
                565                 570                 575

Met Glu Lys Gly Thr Asp Lys Glu Gln Asp Val Asp Val Ser Ser His
            580                 585                 590

Ser Tyr Thr Ile Asn Gly Leu Lys Lys Tyr Thr Glu Tyr Ser Phe Arg
        595                 600                 605

Val Val Ala Tyr Asn Lys His Gly Pro Gly Val Ser Thr Pro Asp Val
610                 615                 620

Ala Val Arg Thr Leu Ser Asp Val Pro Ser Ala Pro Gln Asn Leu
625                 630                 635                 640

Ser Leu Glu Val Arg Asn Ser Lys Ser Ile Met Ile His Trp Gln Pro
                645                 650                 655

Pro Ala Pro Ala Thr Gln Asn Gly Gln Ile Thr Gly Tyr Lys Ile Arg
            660                 665                 670

Tyr Arg Lys Ala Ser Arg Lys Ser Asp Val Thr Glu Thr Leu Val Ser
        675                 680                 685

Gly Thr Gln Leu Ser Gln Leu Ile Glu Gly Leu Asp Arg Gly Thr Glu
690                 695                 700
```

```
Tyr Asn Phe Arg Val Ala Ala Leu Thr Ile Asn Gly Thr Gly Pro Ala
705                 710                 715                 720

Thr Asp Trp Leu Ser Ala Glu Thr Phe Glu Ser Asp Leu Asp Glu Thr
            725                 730                 735

Arg Val Pro Glu Val Pro Ser Ser Leu His Val Arg Pro Leu Val Thr
        740                 745                 750

Ser Ile Val Val Ser Trp Thr Pro Pro Glu Asn Gln Asn Ile Val Val
    755                 760                 765

Arg Gly Tyr Ala Ile Gly Tyr Gly Ile Gly Ser Pro His Ala Gln Thr
770                 775                 780

Ile Lys Val Asp Tyr Lys Gln Arg Tyr Thr Ile Glu Asn Leu Asp
785                 790                 795                 800

Pro Ser Ser His Tyr Val Ile Thr Leu Lys Ala Phe Asn Asn Val Gly
            805                 810                 815

Glu Gly Ile Pro Leu Tyr Glu Ser Ala Val Thr Arg Pro His Thr Asp
        820                 825                 830

Thr Ser Glu Val Asp Leu Phe Val Ile Asn Ala Pro Tyr Thr Pro Val
    835                 840                 845

Pro Asp Pro Thr Pro Met Met Pro Pro Val Gly Val Gln Ala Ser Ile
850                 855                 860

Leu Ser His Asp Thr Ile Arg Ile Thr Trp Ala Asp Asn Ser Leu Pro
865                 870                 875                 880

Lys His Gln Lys Ile Thr Asp Ser Arg Tyr Tyr Thr Val Arg Trp Lys
            885                 890                 895

Thr Asn Ile Pro Ala Asn Thr Lys Tyr Lys Asn Ala Asn Ala Thr Thr
        900                 905                 910

Leu Ser Tyr Leu Val Thr Gly Leu Lys Pro Asn Thr Leu Tyr Glu Phe
    915                 920                 925

Ser Val Met Val Thr Lys Gly Arg Arg Ser Ser Thr Trp Ser Met Thr
930                 935                 940

Ala His Gly Thr Thr Phe Glu Leu Val Pro Thr Ser Pro Pro Lys Asp
945                 950                 955                 960

Val Thr Val Val Ser Lys Glu Gly Lys Pro Lys Thr Ile Ile Val Asn
            965                 970                 975

Trp Gln Pro Pro Ser Glu Ala Asn Gly Lys Ile Thr Gly Tyr Ile Ile
        980                 985                 990

Tyr Tyr Ser Thr Asp Val Asn Ala Glu Ile His Asp Trp Val Ile Glu
    995                 1000                1005

Pro Val Val Gly Asn Arg Leu Thr His Gln Ile Gln Glu Leu Thr
1010                 1015                1020

Leu Asp Thr Pro Tyr Tyr Phe Lys Ile Gln Ala Arg Asn Ser Lys
1025                1030                 1035

Gly Met Gly Pro Met Ser Glu Ala Val Gln Phe Arg Thr Pro Lys
1040                1045                 1050

Ala Asp Ser Ser Asp Lys Met Pro Asn Asp Gln Ala Ser Gly Ser
1055                1060                 1065

Gly Gly Lys Gly Ser Arg Leu Pro Asp Leu Gly Ser Asp Tyr Lys
1070                1075                 1080

Pro Pro Met Ser Gly Ser Asn Ser Pro His Gly Ser Pro Thr Ser
1085                1090                 1095

Pro Leu Asp Ser Asn Met Leu Leu Val Ile Ile Val Ser Val Gly
1100                1105                 1110

Val Ile Thr Ile Val Val Val Val Ile Ile Ala Val Phe Cys Thr
```

|  |  |  | 1115 |  |  |  | 1120 |  |  |  | 1125 |  |

Arg Arg Thr Thr Ser His Gln Lys Lys Arg Ala Ala Cys Lys
1130                1135                1140

Ser Val Asn Gly Ser His Lys Tyr Lys Gly Asn Ser Lys Asp Val
1145                1150                1155

Lys Pro Pro Asp Leu Trp Ile His His Glu Arg Leu Glu Leu Lys
1160                1165                1170

Pro Ile Asp Lys Ser Pro Asp Pro Asn Pro Ile Met Thr Asp Thr
1175                1180                1185

Pro Ile Pro Arg Asn Ser Gln Asp Ile Thr Pro Val Asp Asn Ser
1190                1195                1200

Met Asp Ser Asn Ile His Gln Arg Arg Asn Ser Tyr Arg Gly His
1205                1210                1215

Glu Ser Glu Asp Ser Met Ser Thr Leu Ala Gly Arg Arg Gly Met
1220                1225                1230

Arg Pro Lys Met Met Met Pro Phe Asp Ser Gln Pro Pro Gln Pro
1235                1240                1245

Val Ile Ser Ala His Pro Ile His Ser Leu Asp Asn Pro His His
1250                1255                1260

His Phe His Ser Ser Ser Leu Ala Ser Pro Ala Arg Ser His Leu
1265                1270                1275

Tyr His Pro Gly Ser Pro Trp Pro Ile Gly Thr Ser Met Ser Leu
1280                1285                1290

Ser Asp Arg Ala Asn Ser Thr Glu Ser Val Arg Asn Thr Pro Ser
1295                1300                1305

Thr Asp Thr Met Pro Ala Ser Ser Ser Gln Thr Cys Cys Thr Asp
1310                1315                1320

His Gln Asp Pro Glu Gly Ala Thr Ser Ser Ser Tyr Leu Ala Ser
1325                1330                1335

Ser Gln Glu Glu Asp Ser Gly Gln Ser Leu Pro Thr Ala His Val
1340                1345                1350

Arg Pro Ser His Pro Leu Lys Ser Phe Ala Val Pro Ala Ile Pro
1355                1360                1365

Pro Pro Gly Pro Pro Thr Tyr Asp Pro Ala Leu Pro Ser Thr Pro
1370                1375                1380

Leu Leu Ser Gln Gln Ala Leu Asn His His Ile His Ser Val Lys
1385                1390                1395

Thr Ala Ser Ile Gly Thr Leu Gly Arg Ser Arg Pro Pro Met Pro
1400                1405                1410

Val Val Val Pro Ser Ala Pro Glu Val Gln Glu Thr Thr Arg Met
1415                1420                1425

Leu Glu Asp Ser Glu Ser Ser Tyr Glu Pro Asp Glu Leu Thr Lys
1430                1435                1440

Glu Met Ala His Leu Glu Gly Leu Met Lys Asp Leu Asn Ala Ile
1445                1450                1455

Thr Thr Ala
1460

<210> SEQ ID NO 7
<211> LENGTH: 4227
<212> TYPE: DNA
<213> ORGANISM: Homo sapiens

<400> SEQUENCE: 7

```
atggcggcgg agcggggagc ccggcgactc ctcagcaccc cctccttctg gctctactgc    60
ctgctgctgc tcgggcgccg ggcgccgggc gccgcggccg ccaggagcgg ctccgcgccg   120
cagtccccag gagccagcat tcgaacgttc actccatttt attttctggt ggagccggtg   180
gatacactct cagttagagg ctcttctgtt atattaaact gttcagcata ttctgagcct   240
tctccaaaaa ttgaatggaa aaagatgga acttttttaa acttagtatc agatgatcga   300
cgccagcttc tcccggatgg atctttattt atcagcaatg tggtgcattc caaacacaat   360
aaacctgatg aaggttatta tcagtgtgtg ccactgttg agagtcttgg aactattatc   420
agtagaacag cgaagctcat agtagcaggt cttccaagat ttaccagcca accagaacct   480
tcctcagttt atgctgggaa caatgcaatt ctgaattgtg aagttaatgc agatttggtc   540
ccatttgtga ggtgggaaca aacagacaa ccccttcttc tggatgatag agttatcaaa   600
cttccaagtg gaatgctggt tatcagcaat gcaactgaag gagatggcgg gctttatcgc   660
tgcgtagtgg aaagtggtgg gccaccaaag tatagtgatg aagttgaatt gaaggttctt   720
ccagatcctg aggtgatatc agacttggta tttttgaaac agccttctcc cttagtcaga   780
gtcattggtc aggatgtagt gttgccatgt gttgcttcag acttcctac tccaaccatt   840
aaatggatga aaaatgagga ggcacttgac acagaaagct ctgaaagatt ggtattgctg   900
gcaggtggta gcctggagat cagtgatgtt actgaggatg atgctgggac ttattttgt   960
atagctgata atgaaaatga gacaattgaa gctcaagcag agcttacagt gcaagctcaa  1020
cctgaattcc tgaagcagcc tactaatata tatgctcacg aatctatgga tattgtattt  1080
gaatgtgaag tgactggaaa accaactcca actgtgaagt gggtcaaaaa tggggatatg  1140
gttatcccaa gtgattattt taagattgta aaggaacata atcttcaagt tttgggtctg  1200
gtgaaatcag atgaagggtt ctatcagtgc attgctgaaa atgatgttgg aaatgcacaa  1260
gctggagccc aactgataat ccttgaacat gcaccagcca caacgggacc actgccttca  1320
gctcctcggg atgtcgtggc ctccctggtc tctacccgct tcatcaaatt gacgtggcgg  1380
acacctgcat cagatcctca cggagacaac cttacctact ctgtgttcta caccaaggaa  1440
gggattgcta gggaacgtgt tgagaatacc agtcacccag agagatgca agtaaccatt  1500
caaaacctaa tgccagcgac cgtgtacatc tttagagtta tggctcaaaa taagcatggc  1560
tcaggagaga gttcagctcc actgcgagta gaaacacaac ctgaggttca gctccctggc  1620
ccagcaccta accttcgtgc atatgcagct tcgcctacct ccatcactgt tacgtgggaa  1680
acaccagtgt ctggcaatgg ggaaattcag aattataaat tgtactacat ggaaaagggg  1740
actgataaag aacaggatgt tgatgtttca agtcactctt acaccattaa tgggttgaaa  1800
aaatatacag agtatagttt ccgagtggtg gcctacaata acatggtcc tggagtttcc  1860
acaccagatg ttgctgttcg aacattgtca gatgttccca gtgctgctcc tcagaatctg  1920
tccttggaag tgagaaattc aaaagagtatt atgattcact ggcagccacc tgctccagcc  1980
acacaaaatg ggcagattac tggctacaag attcgctacc gaaaggcctc ccgaaagagt  2040
gatgtcactg agaccttggt aagcgggaca cagctgtctc agctgattga aggtcttgat  2100
cgggggactg agtataattt ccgagtggct gctctaacaa tcaatggtac aggcccggca  2160
actgactggc tgtctgctga aactttgaa agtgacctag atgaaactcg tgttcctgaa  2220
gtgcctagct ctcttcacgt acgcccgctc gttactagca tcgtagtgag ctggactcct  2280
ccagagaatc agaacattgt ggtcagaggt tacgccattg ttatggcat ggcagcccc  2340
catgcccaga ccatcaaagt ggactataaa cagcgctatt acaccattga aaatctggat  2400
```

```
cccagctctc actatgtgat taccctgaaa gcatttaata acgtgggtga aggcatcccc    2460
ctgtatgaga gtgctgtgac caggcctcac acagacactt ctgaagttga tttatttgtt    2520
attaatgctc catacactcc agtgccagat cccactccca tgatgccacc agtgggagtt    2580
caggcttcca ttctgagtca tgacaccatc aggattacgt gggcagacaa ctcgctgccc    2640
aagcaccaga agattacaga ctcccgatac taccgtcc gatggaaaac caacatccca    2700
gcaaacacca agtacaagaa tgcaaatgca accactttga gttatttggt gactggttta    2760
aagccgaata cactctatga attctctgtg atggtgacca aggtcgaag atcaagtaca    2820 tggagtatga cagcccatgg gaccacccttt gaattagttc cgacttctcc acccaaggat    2880
gtgactgttg tgagtaaaga ggggaaacct aagaccataa ttgtgaattg cagcctccc    2940 tccgaagcca atggcaaaat tacaggttac atcatatatt acagtacaga gtgaatgca    3000 gagatacatg actgggttat tgagcctgtt gtgggaaaca gactgactca ccagatacaa    3060
gagttaactc ttgacacacc atactacttc aaaatccagg cacggaactc aaagggcatg    3120
ggacccatgt ctgaagctgt ccaattcaga acacctaaag cggactcctc tgataaaatg    3180
cctaatgatc aagcctcagg gtctggaggg aaaggaagcc ggctgccaga cctaggatcc    3240
gactacaaac ctccaatgag cggcagtaac agccctcatg ggagccccac ctctcctctg    3300
gacagtaata tgctgctggt cataattgtt tctgttggcg tcatcaccat cgtggtggtt    3360
gtgattatcg ctgtcttttg taccccgtcgt accacctctc accagaaaaa gaaacgagct    3420
gcctgcaaat cagtgaatgg ctctcataag tacaaaggga attccaaaga tgtgaaacct    3480
ccagatctct ggatccatca tgagagactg gagctgaaac ccattgataa gtctccagac    3540 ccaaaccca tcatgactga tactccaatt cctcgcaact tcaagatat cacaccagtt    3600 gacaactcca tggacagcaa tatccatcaa aggcgaaatt catacagagg gcatgagtca    3660
gaggacagca tgtctacact ggctggaagg cgaggaatga gaccaaaaat gatgatgccc    3720
tttgactccc agccaccca gcaatccgtt cgaaataccc ccagcactga caccatgcca    3780
gcctcttcgt ctcaaacatg ctgcactgat caccaggacc ctgaaggtgc taccagctcc    3840
tcttacttgg ccagctccca agaggaagat tcaggccaga gtcttcccac tgcccatgtt    3900
cgcccttccc acccattgaa gagcttcgcc gtgccagcaa tcccgcctcc aggacctccc    3960
acctatgatc ctgcattgcc aagcacacca ttactgtccc agcaagctct gaaccatcac    4020
attcactcag tgaagacagc ctccatcggg actctaggaa ggagccggcc tcctatgcca    4080
gtggttgttc ccagtgcccc tgaagtgcag gagaccacca ggatgttgga agactccgag    4140
agtagctatg aaccagatga gctgaccaaa gagatggccc acctggaagg actaatgaag    4200
gacctaaacg ctatcacaac agcatga                                        4227
```

<210> SEQ ID NO 8
<211> LENGTH: 1408
<212> TYPE: PRT
<213> ORGANISM: Homo sapiens

<400> SEQUENCE: 8

Met Ala Ala Glu Arg Gly Ala Arg Arg Leu Leu Ser Thr Pro Ser Phe
1               5                   10                  15

Trp Leu Tyr Cys Leu Leu Leu Leu Gly Arg Arg Ala Pro Gly Ala Ala
                20                  25                  30

Ala Ala Arg Ser Gly Ser Ala Pro Gln Ser Pro Gly Ala Ser Ile Arg
            35                  40                  45

```
Thr Phe Thr Pro Phe Tyr Phe Leu Val Glu Pro Val Asp Thr Leu Ser
         50                  55                  60

Val Arg Gly Ser Ser Val Ile Leu Asn Cys Ser Ala Tyr Ser Glu Pro
 65                  70                  75                  80

Ser Pro Lys Ile Glu Trp Lys Lys Asp Gly Thr Phe Leu Asn Leu Val
                 85                  90                  95

Ser Asp Asp Arg Arg Gln Leu Leu Pro Asp Gly Ser Leu Phe Ile Ser
                100                 105                 110

Asn Val Val His Ser Lys His Asn Lys Pro Asp Glu Gly Tyr Tyr Gln
             115                 120                 125

Cys Val Ala Thr Val Glu Ser Leu Gly Thr Ile Ile Ser Arg Thr Ala
         130                 135                 140

Lys Leu Ile Val Ala Gly Leu Pro Arg Phe Thr Ser Gln Pro Glu Pro
145                 150                 155                 160

Ser Ser Val Tyr Ala Gly Asn Asn Ala Ile Leu Asn Cys Glu Val Asn
                 165                 170                 175

Ala Asp Leu Val Pro Phe Val Arg Trp Glu Gln Asn Arg Gln Pro Leu
             180                 185                 190

Leu Leu Asp Asp Arg Val Ile Lys Leu Pro Ser Gly Met Leu Val Ile
         195                 200                 205

Ser Asn Ala Thr Glu Gly Asp Gly Gly Leu Tyr Arg Cys Val Val Glu
210                 215                 220

Ser Gly Gly Pro Pro Lys Tyr Ser Asp Glu Val Glu Leu Lys Val Leu
225                 230                 235                 240

Pro Asp Pro Glu Val Ile Ser Asp Leu Val Phe Leu Lys Gln Pro Ser
                245                 250                 255

Pro Leu Val Arg Val Ile Gly Gln Asp Val Val Leu Pro Cys Val Ala
             260                 265                 270

Ser Gly Leu Pro Thr Pro Thr Ile Lys Trp Met Lys Asn Glu Glu Ala
         275                 280                 285

Leu Asp Thr Glu Ser Ser Glu Arg Leu Val Leu Leu Ala Gly Gly Ser
     290                 295                 300

Leu Glu Ile Ser Asp Val Thr Glu Asp Ala Gly Thr Tyr Phe Cys
305                 310                 315                 320

Ile Ala Asp Asn Gly Asn Glu Thr Ile Glu Ala Gln Ala Glu Leu Thr
                325                 330                 335

Val Gln Ala Gln Pro Glu Phe Leu Lys Gln Pro Thr Asn Ile Tyr Ala
             340                 345                 350

His Glu Ser Met Asp Ile Val Phe Glu Cys Glu Val Thr Gly Lys Pro
         355                 360                 365

Thr Pro Thr Val Lys Trp Val Lys Asn Gly Asp Met Val Ile Pro Ser
     370                 375                 380

Asp Tyr Phe Lys Ile Val Lys Glu His Asn Leu Gln Val Leu Gly Leu
385                 390                 395                 400

Val Lys Ser Asp Glu Gly Phe Tyr Gln Cys Ile Ala Glu Asn Asp Val
                405                 410                 415

Gly Asn Ala Gln Ala Gly Ala Gln Leu Ile Ile Leu Glu His Ala Pro
             420                 425                 430

Ala Thr Thr Gly Pro Leu Pro Ser Ala Pro Arg Asp Val Val Ala Ser
         435                 440                 445

Leu Val Ser Thr Arg Phe Ile Lys Leu Thr Trp Arg Thr Pro Ala Ser
     450                 455                 460
```

-continued

```
Asp Pro His Gly Asp Asn Leu Thr Tyr Ser Val Phe Tyr Thr Lys Glu
465                 470                 475                 480

Gly Ile Ala Arg Glu Arg Val Glu Asn Thr Ser His Pro Gly Glu Met
            485                 490                 495

Gln Val Thr Ile Gln Asn Leu Met Pro Ala Thr Val Tyr Ile Phe Arg
        500                 505                 510

Val Met Ala Gln Asn Lys His Gly Ser Gly Glu Ser Ser Ala Pro Leu
    515                 520                 525

Arg Val Glu Thr Gln Pro Glu Val Gln Leu Pro Gly Pro Ala Pro Asn
530                 535                 540

Leu Arg Ala Tyr Ala Ala Ser Pro Thr Ser Ile Thr Val Thr Trp Glu
545                 550                 555                 560

Thr Pro Val Ser Gly Asn Gly Glu Ile Gln Asn Tyr Lys Leu Tyr Tyr
            565                 570                 575

Met Glu Lys Gly Thr Asp Lys Glu Gln Asp Val Asp Val Ser Ser His
        580                 585                 590

Ser Tyr Thr Ile Asn Gly Leu Lys Lys Tyr Thr Glu Tyr Ser Phe Arg
    595                 600                 605

Val Val Ala Tyr Asn Lys His Gly Pro Gly Val Ser Thr Pro Asp Val
610                 615                 620

Ala Val Arg Thr Leu Ser Asp Val Pro Ser Ala Ala Pro Gln Asn Leu
625                 630                 635                 640

Ser Leu Glu Val Arg Asn Ser Lys Ser Ile Met Ile His Trp Gln Pro
            645                 650                 655

Pro Ala Pro Ala Thr Gln Asn Gly Gln Ile Thr Gly Tyr Lys Ile Arg
        660                 665                 670

Tyr Arg Lys Ala Ser Arg Lys Ser Asp Val Thr Glu Thr Leu Val Ser
    675                 680                 685

Gly Thr Gln Leu Ser Gln Leu Ile Glu Gly Leu Asp Arg Gly Thr Glu
690                 695                 700

Tyr Asn Phe Arg Val Ala Ala Leu Thr Ile Asn Gly Thr Gly Pro Ala
705                 710                 715                 720

Thr Asp Trp Leu Ser Ala Glu Thr Phe Glu Ser Asp Leu Asp Glu Thr
            725                 730                 735

Arg Val Pro Glu Val Pro Ser Ser Leu His Val Arg Pro Leu Val Thr
        740                 745                 750

Ser Ile Val Val Ser Trp Thr Pro Pro Glu Asn Gln Asn Ile Val Val
    755                 760                 765

Arg Gly Tyr Ala Ile Gly Tyr Gly Ile Gly Ser Pro His Ala Gln Thr
770                 775                 780

Ile Lys Val Asp Tyr Lys Gln Arg Tyr Tyr Thr Ile Glu Asn Leu Asp
785                 790                 795                 800

Pro Ser Ser His Tyr Val Ile Thr Leu Lys Ala Phe Asn Asn Val Gly
            805                 810                 815

Glu Gly Ile Pro Leu Tyr Glu Ser Ala Val Thr Arg Pro His Thr Asp
        820                 825                 830

Thr Ser Glu Val Asp Leu Phe Val Ile Asn Ala Pro Tyr Thr Pro Val
    835                 840                 845

Pro Asp Pro Thr Pro Met Met Pro Pro Val Gly Val Gln Ala Ser Ile
850                 855                 860

Leu Ser His Asp Thr Ile Arg Ile Thr Trp Ala Asp Asn Ser Leu Pro
865                 870                 875                 880

Lys His Gln Lys Ile Thr Asp Ser Arg Tyr Tyr Thr Val Arg Trp Lys
```

```
                  885                 890                 895
Thr Asn Ile Pro Ala Asn Thr Lys Tyr Lys Asn Ala Asn Ala Thr Thr
                900                 905                 910
Leu Ser Tyr Leu Val Thr Gly Leu Lys Pro Asn Thr Leu Tyr Glu Phe
                915                 920                 925
Ser Val Met Val Thr Lys Gly Arg Arg Ser Ser Thr Trp Ser Met Thr
                930                 935                 940
Ala His Gly Thr Thr Phe Glu Leu Val Pro Thr Ser Pro Pro Lys Asp
945                 950                 955                 960
Val Thr Val Val Ser Lys Glu Gly Lys Pro Lys Thr Ile Ile Val Asn
                965                 970                 975
Trp Gln Pro Pro Ser Glu Ala Asn Gly Lys Ile Thr Gly Tyr Ile Ile
                980                 985                 990
Tyr Tyr Ser Thr Asp Val Asn Ala Glu Ile His Asp Trp Val Ile Glu
                995                 1000                1005
Pro Val Val Gly Asn Arg Leu Thr His Gln Ile Gln Glu Leu Thr
            1010                1015                1020
Leu Asp Thr Pro Tyr Tyr Phe Lys Ile Gln Ala Arg Asn Ser Lys
            1025                1030                1035
Gly Met Gly Pro Met Ser Glu Ala Val Gln Phe Arg Thr Pro Lys
            1040                1045                1050
Ala Asp Ser Ser Asp Lys Met Pro Asn Asp Gln Ala Ser Gly Ser
            1055                1060                1065
Gly Gly Lys Gly Ser Arg Leu Pro Asp Leu Gly Ser Asp Tyr Lys
            1070                1075                1080
Pro Pro Met Ser Gly Ser Asn Ser Pro His Gly Ser Pro Thr Ser
            1085                1090                1095
Pro Leu Asp Ser Asn Met Leu Leu Val Ile Ile Val Ser Val Gly
            1100                1105                1110
Val Ile Thr Ile Val Val Val Ile Ile Ala Val Phe Cys Thr
            1115                1120                1125
Arg Arg Thr Thr Ser His Gln Lys Lys Lys Arg Ala Ala Cys Lys
            1130                1135                1140
Ser Val Asn Gly Ser His Lys Tyr Lys Gly Asn Ser Lys Asp Val
            1145                1150                1155
Lys Pro Pro Asp Leu Trp Ile His His Glu Arg Leu Glu Leu Lys
            1160                1165                1170
Pro Ile Asp Lys Ser Pro Asp Pro Asn Pro Ile Met Thr Asp Thr
            1175                1180                1185
Pro Ile Pro Arg Asn Ser Gln Asp Ile Thr Pro Val Asp Asn Ser
            1190                1195                1200
Met Asp Ser Asn Ile His Gln Arg Arg Asn Ser Tyr Arg Gly His
            1205                1210                1215
Glu Ser Glu Asp Ser Met Ser Thr Leu Ala Gly Arg Arg Gly Met
            1220                1225                1230
Arg Pro Lys Met Met Met Pro Phe Asp Ser Gln Pro Pro Gln Gln
            1235                1240                1245
Ser Val Arg Asn Thr Pro Ser Thr Asp Thr Met Pro Ala Ser Ser
            1250                1255                1260
Ser Gln Thr Cys Cys Thr Asp His Gln Asp Pro Glu Gly Ala Thr
            1265                1270                1275
Ser Ser Ser Tyr Leu Ala Ser Ser Gln Glu Glu Asp Ser Gly Gln
            1280                1285                1290
```

```
Ser Leu Pro Thr Ala His Val Arg Pro Ser His Pro Leu Lys Ser
    1295                1300                1305

Phe Ala Val Pro Ala Ile Pro Pro Gly Pro Pro Thr Tyr Asp
    1310                1315                1320

Pro Ala Leu Pro Ser Thr Pro Leu Leu Ser Gln Gln Ala Leu Asn
    1325                1330                1335

His His Ile His Ser Val Lys Thr Ala Ser Ile Gly Thr Leu Gly
    1340                1345                1350

Arg Ser Arg Pro Pro Met Pro Val Val Pro Ser Ala Pro Glu
    1355                1360                1365

Val Gln Glu Thr Thr Arg Met Leu Glu Asp Ser Glu Ser Ser Tyr
    1370                1375                1380

Glu Pro Asp Glu Leu Thr Lys Glu Met Ala His Leu Glu Gly Leu
    1385                1390                1395

Met Lys Asp Leu Asn Ala Ile Thr Thr Ala
    1400                1405

<210> SEQ ID NO 9
<211> LENGTH: 4479
<212> TYPE: DNA
<213> ORGANISM: Mus musculus

<400> SEQUENCE: 9
atggcggcgg agcgcgaagc cgggcgactc ctctgcacct cctcctcccg gcgctgctgt        60
ccgccaccgc cgctgctgct gttgctgccg ctgctgctgc tgctcggacg cccggcgtcc       120
ggcgccgcgg ccacgaagag cggctccccg ccgcagtccg caggagccag tgttcgaaca       180
ttcactccgt tttattttct ggtggagcca gtagacaccc tctcagttag aggctcttct       240
gttatattaa attgctcggc atattctgag ccctctccaa acattgaatg gaagaaagat       300
gggacttttt taaacttaga atcagatgat cgacgccagc tactcccaga tggatcttta       360
ttcatcagca acgtggtgca ttccaaacac aataagcctg acgaaggttt ctatcagtgt       420
gtagccactg tggataatct tggaaccatt gtcagcagaa cagccaagct cacagtagca       480
ggtcttccaa gatttaccag ccaaccagaa ccttcttcag tctatgttgg aaacagtgca       540
attctgaatt gtgaagttaa tgcagatttg gtcccatttg ttaggtggga acagaatcga       600
cagccccttc ttctagatga caggattgtc aaacttccaa gtggaacact ggttatcagc       660
aatgctactg aaggagatgg gggactctac cgctgcattg ttgaaagtgg tgggccacca       720
aagtttagtg acgaagctga attgaaagtt cttcaagatc ctgaggaaat tgtagacttg       780
gtatttctga tgcgaccatc ttctatgatg aaagtcactg gtcagagtgc agtgttgcca       840
tgtgttgtct cagggcttcc tgctccagtt gttagatgga tgaaaaacga agaagtgctt       900
gacacagaaa gctctggcag gttggtcttg ctagcaggag gttgcttgga gatcagtgat       960
gtcactgagg atgatgctgg gacttatttt tgcatagctg ataatggaaa taagacagtt      1020
gaagctcagg cggagcttac tgtgcaagtg ccacctggat tcctgaaaca acctgctaac      1080
atatatgctc acgaatccat ggacattgta tttgaatgtg aagtcactgg gaagccaact      1140
ccaactgtga agtgggtcaa gatggggat gtggttatcc ccagtgatta ctttaaaatt      1200
gtaaaggaac ataatcttca agttttgggt ctggtgaaat cagatgaagg ttctatcaa      1260 tgcattgctg agaatgatgt tggaaatgca caagctggag cccagctgat aatccttgag      1320
catgatgttg ccatcccaac attacctccc acttcactga ccagtgccac tactgaccat      1380
```

```
ctagcaccag ccacaacggg accattacct tcagctcctc gagacgtcgt ggcctccctg    1440
gtctctactc gcttcattaa attgacatgg cgtacacctg catcagaccc tcatggagac    1500
aatctcacct actctgtgtt ctacaccaag gaaggggttg ctagggagcg tgttgagaat    1560
accagccagc caggagagat gcaggtgact attcaaaact tgatgccagc aactgtgtac    1620
atcttcaaag ttatggctca aaataagcat ggctctggag aaagttcagc tcctcttcga    1680
gtagagacac agcctgaggt tcagctccct ggcccagcac taatatccg tgcttatgca    1740 acgtcaccta cttctatcac tgtcacctgg gaaacaccgt tatctggcaa tggggaaatt    1800
caaaattaca aattgtacta catggaaaaa ggaactgata agaacagga tattgatgtt    1860 tcaagtcact cctacaccat taatggactg aagaaataca cagaatacag tttccgagtg    1920
gtggcctaca ataaacatgg tcctggagtt tctacacaag atgttgctgt cgaacatta    1980 tcagatgttc ccagtgctgc tcctcagaat ctgtccttag aagtgagaaa ttcaaagagt    2040
atagtgatcc actggcagcc ccttcctca accacacaaa atgggcagat aactggctac    2100
aagattcgat atcgaaaggc ctcccgaaaa agtgatgtca ctgagacctt ggtaactggg    2160
acacagctgt ctcagctgat tgaaggtctt gatcggggga cagaatataa cttccgagtc    2220
gctgctctca cagtcaatgg tacaggtcca gcaactgatt ggctgtctgc tgaaactttt    2280
gaaagcgacc tagatgaaac tcgtgttcct gaagtgccca gctctcttca tgtccgtccg    2340
ctcgtcacta gcattgtagt gagctggact cctccagaga accagaacat tgtggtccga    2400
ggttatgcca tcggttacgg cattggcagc cctcatgccc agaccatcaa agtggactat    2460
aaacaacgtt attacaccat cgaaaacttg atccaagct ctcattacgt gattaccttg    2520
aaagcattta acaatgttgg cgaaggcatc ccccttatg agagtgctgt gaccagacct    2580
cacacagaca cttctgaagt tgatttattt gttattaatg ctccatacac tccagtgcca    2640
gatcccactc ccatgatgcc accagtggga gttcaggctt ccattctgag tcacgacacc    2700
ataaggatta cctgggcaga caactccctg cccaaacacc agaagattac agactcccgc    2760
tactacacag tccggtggaa gaccaacatc ccagcaaaca cgaagtacaa gaatgcaaat    2820
gcaacgacgt taagctattt ggttactggt ttaaagccaa atacgctcta tgagttctct    2880
gtgatggtga ccaaaggcag aaggtcaagc acgtggagta tgacagctca tggcgctacc    2940
tttgaattag ttcctacttc tccacctaag gatgtgacga ttgtgagtaa ggaaggaaaa    3000
cctagaacca tcatagtgaa ttggcagcct ccctctgaag ctaacggcaa gattacaggt    3060
tacatcatct attacagcac ggatgtgaat gcagagatac atgactgggt tattgaacca    3120
gttgtgggaa acagactgac tcaccagatt caagagttaa cacttgatac gccatactac    3180
ttcaaaatcc aggcccggaa ctcaagggc atggggccca tgtctgaagc tgtacagttc    3240
agaacaccta agcggactc ctctgataaa atgcctaatg accaagcctt agggtcagca    3300
ggaaaaggaa gccgactacc agacctggga tctgactaca aacctccaat gagtggcagc    3360
aacagccctc acgggagccc cacctcccct ctggacagca acatgctgct ggtcatcatt    3420
gtctctgttg gcgtcatcac tatcgtggtg gttgtggtca ttgctgtctt ttgtacccgg    3480
cgcaccacct ctcaccagaa gaagaaacga gctgcgtgca aatcagtgaa tggctcccat    3540
aagtacaagg gcaattgcaa agatgtgaag cctccagacc tatggatcca tcacgagaga    3600
ctagagttga agcctattga caagtctcca gatcctaacc ctgtcatgac tgatactcca    3660
atccctcgaa actctcaaga tatcaccacca gtggacaatt ccatggatag caatatccat    3720
caaaggcgga attcatacag agggcatgag tcagaggaca gcatgtctac actggctgga    3780
```

-continued

```
aggaggggaa tgagaccaaa aatgatgatg cccttTgact ctcagccacc tcagcctgtg    3840
attagtgccc atcccatcca ttccctcgat aaccctcacc atcatttcca ctccagcagc    3900
ctcgcttctc cagcccgcag tcatctctac cacccaagca gcccatggcc cattggcaca    3960
tccatgtccc tttcagacag ggccaattcc acagaatctg ttcgaaatac ccccagcacg    4020
gacaccatgc cagcgtcctc gtctcagacg tgctgcactg accatcagga ccctgagggt    4080
gctactagct cctcttactt ggccagctcc caagaggaag actcaggcca gagtcttccc    4140
acagcccatg tccgcccttc ccaccctctg aagagcttcg ctgtgccagc aatcccaccc    4200
ccaggacctc ctctctatga tcctgcactg ccaagcacac cattactgtc ccagcaagct    4260
ctgaaccatc acattcactc agtgaaaaca gcctccatcg ggacgttagg aaggagccgg    4320
cctcctatgc cagtggttgt tccgagtgcc cctgaagtac aggagaccac caggatgctg    4380
gaagactccg agagtagcta tgaaccagat gagctgacca aagagatggc ccacctggaa    4440
ggactaatga aggacctaaa tgccatcaca acagcctga                            4479
```

<210> SEQ ID NO 10
<211> LENGTH: 1492
<212> TYPE: PRT
<213> ORGANISM: Mus musculus

<400> SEQUENCE: 10

```
Met Ala Ala Glu Arg Glu Ala Gly Arg Leu Leu Cys Thr Ser Ser
1               5                   10                  15

Arg Arg Cys Cys Pro Pro Pro Leu Leu Leu Leu Pro Leu Leu
            20                  25                  30

Leu Leu Leu Gly Arg Pro Ala Ser Gly Ala Ala Ala Thr Lys Ser Gly
        35                  40                  45

Ser Pro Pro Gln Ser Ala Gly Ala Ser Val Arg Thr Phe Thr Pro Phe
    50                  55                  60

Tyr Phe Leu Val Glu Pro Val Asp Thr Leu Ser Val Arg Gly Ser Ser
65                  70                  75                  80

Val Ile Leu Asn Cys Ser Ala Tyr Ser Glu Pro Ser Pro Asn Ile Glu
                85                  90                  95

Trp Lys Lys Asp Gly Thr Phe Leu Asn Leu Glu Ser Asp Asp Arg Arg
            100                 105                 110

Gln Leu Leu Pro Asp Gly Ser Leu Phe Ile Ser Asn Val Val His Ser
        115                 120                 125

Lys His Asn Lys Pro Asp Glu Gly Phe Tyr Gln Cys Val Ala Thr Val
    130                 135                 140

Asp Asn Leu Gly Thr Ile Val Ser Arg Thr Ala Lys Leu Thr Val Ala
145                 150                 155                 160

Gly Leu Pro Arg Phe Thr Ser Gln Pro Glu Pro Ser Ser Val Tyr Val
                165                 170                 175

Gly Asn Ser Ala Ile Leu Asn Cys Glu Val Asn Ala Asp Leu Val Pro
            180                 185                 190

Phe Val Arg Trp Glu Gln Asn Arg Gln Pro Leu Leu Leu Asp Asp Arg
        195                 200                 205

Ile Val Lys Leu Pro Ser Gly Thr Leu Val Ile Ser Asn Ala Thr Glu
    210                 215                 220

Gly Asp Gly Gly Leu Tyr Arg Cys Ile Val Glu Ser Gly Gly Pro Pro
225                 230                 235                 240

Lys Phe Ser Asp Glu Ala Glu Leu Lys Val Leu Gln Asp Pro Glu Glu
```

```
                245                 250                 255
Ile Val Asp Leu Val Phe Leu Met Arg Pro Ser Ser Met Met Lys Val
            260                 265                 270

Thr Gly Gln Ser Ala Val Leu Pro Cys Val Val Ser Gly Leu Pro Ala
            275                 280                 285

Pro Val Val Arg Trp Met Lys Asn Glu Glu Val Leu Asp Thr Glu Ser
            290                 295                 300

Ser Gly Arg Leu Val Leu Leu Ala Gly Gly Cys Leu Glu Ile Ser Asp
305                 310                 315                 320

Val Thr Glu Asp Asp Ala Gly Thr Tyr Phe Cys Ile Ala Asp Asn Gly
            325                 330                 335

Asn Lys Thr Val Glu Ala Gln Ala Glu Leu Thr Val Gln Val Pro Pro
            340                 345                 350

Gly Phe Leu Lys Gln Pro Ala Asn Ile Tyr Ala His Glu Ser Met Asp
            355                 360                 365

Ile Val Phe Glu Cys Glu Val Thr Gly Lys Pro Thr Pro Thr Val Lys
            370                 375                 380

Trp Val Lys Asn Gly Asp Val Val Ile Pro Ser Asp Tyr Phe Lys Ile
385                 390                 395                 400

Val Lys Glu His Asn Leu Gln Val Leu Gly Leu Val Lys Ser Asp Glu
            405                 410                 415

Gly Phe Tyr Gln Cys Ile Ala Glu Asn Asp Val Gly Asn Ala Gln Ala
            420                 425                 430

Gly Ala Gln Leu Ile Ile Leu Glu His Asp Val Ala Ile Pro Thr Leu
            435                 440                 445

Pro Pro Thr Ser Leu Thr Ser Ala Thr Thr Asp His Leu Ala Pro Ala
            450                 455                 460

Thr Thr Gly Pro Leu Pro Ser Ala Pro Arg Asp Val Val Ala Ser Leu
465                 470                 475                 480

Val Ser Thr Arg Phe Ile Lys Leu Thr Trp Arg Thr Pro Ala Ser Asp
            485                 490                 495

Pro His Gly Asp Asn Leu Thr Tyr Ser Val Phe Tyr Thr Lys Glu Gly
            500                 505                 510

Val Ala Arg Glu Arg Val Glu Asn Thr Ser Gln Pro Gly Glu Met Gln
            515                 520                 525

Val Thr Ile Gln Asn Leu Met Pro Ala Thr Val Tyr Ile Phe Lys Val
            530                 535                 540

Met Ala Gln Asn Lys His Gly Ser Gly Glu Ser Ser Ala Pro Leu Arg
545                 550                 555                 560

Val Glu Thr Gln Pro Glu Val Gln Leu Pro Gly Pro Ala Pro Asn Ile
            565                 570                 575

Arg Ala Tyr Ala Thr Ser Pro Thr Ser Ile Thr Val Thr Trp Glu Thr
            580                 585                 590

Pro Leu Ser Gly Asn Gly Glu Ile Gln Asn Tyr Lys Leu Tyr Met
            595                 600                 605

Glu Lys Gly Thr Asp Lys Glu Gln Asp Ile Asp Val Ser Ser His Ser
            610                 615                 620

Tyr Thr Ile Asn Gly Leu Lys Lys Tyr Thr Glu Tyr Ser Phe Arg Val
625                 630                 635                 640

Val Ala Tyr Asn Lys His Gly Pro Gly Val Ser Thr Gln Asp Val Ala
            645                 650                 655

Val Arg Thr Leu Ser Asp Val Pro Ser Ala Ala Pro Gln Asn Leu Ser
            660                 665                 670
```

```
Leu Glu Val Arg Asn Ser Lys Ser Ile Val His Trp Gln Pro Pro
        675                 680                 685

Ser Ser Thr Thr Gln Asn Gly Gln Ile Thr Gly Tyr Lys Ile Arg Tyr
690                 695                 700

Arg Lys Ala Ser Arg Lys Ser Asp Val Thr Glu Thr Leu Val Thr Gly
705                 710                 715                 720

Thr Gln Leu Ser Gln Leu Ile Glu Gly Leu Asp Arg Gly Thr Glu Tyr
            725                 730                 735

Asn Phe Arg Val Ala Ala Leu Thr Val Asn Gly Thr Gly Pro Ala Thr
                740                 745                 750

Asp Trp Leu Ser Ala Glu Thr Phe Glu Ser Asp Leu Asp Glu Thr Arg
            755                 760                 765

Val Pro Glu Val Pro Ser Ser Leu His Val Arg Pro Leu Val Thr Ser
770                 775                 780

Ile Val Val Ser Trp Thr Pro Pro Glu Asn Gln Asn Ile Val Val Arg
785                 790                 795                 800

Gly Tyr Ala Ile Gly Tyr Gly Ile Gly Ser Pro His Ala Gln Thr Ile
                805                 810                 815

Lys Val Asp Tyr Lys Gln Arg Tyr Tyr Thr Ile Glu Asn Leu Asp Pro
                820                 825                 830

Ser Ser His Tyr Val Ile Thr Leu Lys Ala Phe Asn Asn Val Gly Glu
            835                 840                 845

Gly Ile Pro Leu Tyr Glu Ser Ala Val Thr Arg Pro His Thr Asp Thr
850                 855                 860

Ser Glu Val Asp Leu Phe Val Ile Asn Ala Pro Tyr Thr Pro Val Pro
865                 870                 875                 880

Asp Pro Thr Pro Met Met Pro Pro Val Gly Val Gln Ala Ser Ile Leu
                885                 890                 895

Ser His Asp Thr Ile Arg Ile Thr Trp Ala Asp Asn Ser Leu Pro Lys
            900                 905                 910

His Gln Lys Ile Thr Asp Ser Arg Tyr Tyr Thr Val Arg Trp Lys Thr
            915                 920                 925

Asn Ile Pro Ala Asn Thr Lys Tyr Lys Asn Ala Asn Ala Thr Thr Leu
            930                 935                 940

Ser Tyr Leu Val Thr Gly Leu Lys Pro Asn Thr Leu Tyr Glu Phe Ser
945                 950                 955                 960

Val Met Val Thr Lys Gly Arg Arg Ser Ser Thr Trp Ser Met Thr Ala
                965                 970                 975

His Gly Ala Thr Phe Glu Leu Val Pro Thr Ser Pro Pro Lys Asp Val
            980                 985                 990

Thr Val Val Ser Lys Glu Gly Lys Pro Arg Thr Ile Ile Val Asn Trp
            995                 1000                1005

Gln Pro Pro Ser Glu Ala Asn Gly Lys Ile Thr Gly Tyr Ile Ile
    1010                1015                1020

Tyr Tyr Ser Thr Asp Val Asn Ala Glu Ile His Asp Trp Val Ile
    1025                1030                1035

Glu Pro Val Val Gly Asn Arg Leu Thr His Gln Ile Gln Glu Leu
    1040                1045                1050

Thr Leu Asp Thr Pro Tyr Tyr Phe Lys Ile Gln Ala Arg Asn Ser
    1055                1060                1065

Lys Gly Met Gly Pro Met Ser Glu Ala Val Gln Phe Arg Thr Pro
    1070                1075                1080
```

```
Lys Ala Asp Ser Ser Asp Lys Met Pro Asn Asp Gln Ala Leu Gly
1085                1090                1095

Ser Ala Gly Lys Gly Ser Arg Leu Pro Asp Leu Gly Ser Asp Tyr
1100                1105                1110

Lys Pro Pro Met Ser Gly Ser Asn Ser Pro His Gly Ser Pro Thr
1115                1120                1125

Ser Pro Leu Asp Ser Asn Met Leu Leu Val Ile Ile Val Ser Val
1130                1135                1140

Gly Val Ile Thr Ile Val Val Val Val Val Ile Ala Val Phe Cys
1145                1150                1155

Thr Arg Arg Thr Thr Ser His Gln Lys Lys Lys Arg Ala Ala Cys
1160                1165                1170

Lys Ser Val Asn Gly Ser His Lys Tyr Lys Gly Asn Cys Lys Asp
1175                1180                1185

Val Lys Pro Pro Asp Leu Trp Ile His His Glu Arg Leu Glu Leu
1190                1195                1200

Lys Pro Ile Asp Lys Ser Pro Asp Pro Asn Pro Val Met Thr Asp
1205                1210                1215

Thr Pro Ile Pro Arg Asn Ser Gln Asp Ile Thr Pro Val Asp Asn
1220                1225                1230

Ser Met Asp Ser Asn Ile His Gln Arg Arg Asn Ser Tyr Arg Gly
1235                1240                1245

His Glu Ser Glu Asp Ser Met Ser Thr Leu Ala Gly Arg Arg Gly
1250                1255                1260

Met Arg Pro Lys Met Met Met Pro Phe Asp Ser Gln Pro Pro Gln
1265                1270                1275

Pro Val Ile Ser Ala His Pro Ile His Ser Leu Asp Asn Pro His
1280                1285                1290

His His Phe His Ser Ser Ser Leu Ala Ser Pro Ala Arg Ser His
1295                1300                1305

Leu Tyr His Pro Ser Ser Pro Trp Pro Ile Gly Thr Ser Met Ser
1310                1315                1320

Leu Ser Asp Arg Ala Asn Ser Thr Glu Ser Val Arg Asn Thr Pro
1325                1330                1335

Ser Thr Asp Thr Met Pro Ala Ser Ser Ser Gln Thr Cys Cys Thr
1340                1345                1350

Asp His Gln Asp Pro Glu Gly Ala Thr Ser Ser Ser Tyr Leu Ala
1355                1360                1365

Ser Ser Gln Glu Glu Asp Ser Gly Gln Ser Leu Pro Thr Ala His
1370                1375                1380

Val Arg Pro Ser His Pro Leu Lys Ser Phe Ala Val Pro Ala Ile
1385                1390                1395

Pro Pro Pro Gly Pro Pro Leu Tyr Asp Pro Ala Leu Pro Ser Thr
1400                1405                1410

Pro Leu Leu Ser Gln Gln Ala Leu Asn His His Ile His Ser Val
1415                1420                1425

Lys Thr Ala Ser Ile Gly Thr Leu Gly Arg Ser Arg Pro Pro Met
1430                1435                1440

Pro Val Val Val Pro Ser Ala Pro Glu Val Gln Glu Thr Thr Arg
1445                1450                1455

Met Leu Glu Asp Ser Glu Ser Ser Tyr Glu Pro Asp Glu Leu Thr
1460                1465                1470

Lys Glu Met Ala His Leu Glu Gly Leu Met Lys Asp Leu Asn Ala
```

| | 1475 | | 1480 | | 1485 | |

Ile Thr Thr Ala
    1490

<210> SEQ ID NO 11
<211> LENGTH: 4398
<212> TYPE: DNA
<213> ORGANISM: Mus musculus

<400> SEQUENCE: 11

| | | | | | | |
|---|---|---|---|---|---|---|
| atggcggcgg | agcgcgaagc | cgggcgactc | ctctgcacct | cctcctcccg | gcgctgctgt | 60 |
| ccgccaccgc | cgctgctgct | gttgctgccg | ctgctgctgc | tgctcggacg | cccggcgtcc | 120 |
| ggcgccgcgg | ccacgaagag | cggctccccg | ccgcagtccg | caggagccag | tgttcgaaca | 180 |
| ttcactccgt | tttatttct | ggtggagcca | gtagacaccc | tctcagttag | aggctcttct | 240 |
| gttatattaa | attgctcggc | atattctgag | ccctctccaa | acattgaatg | aagaaagat | 300 |
| gggactttt | taaacttaga | atcagatgat | cgacgccagc | tactcccaga | tggatcttta | 360 |
| ttcatcagca | acgtggtgca | ttccaaacac | aataagcctg | acgaaggttt | ctatcagtgt | 420 |
| gtagccactg | tggataatct | tggaaccatt | gtcagcagaa | cagccaagct | cacagtagca | 480 |
| ggtcttccaa | gatttaccag | ccaaccagaa | ccttcttcag | tctatgttgg | aaacagtgca | 540 |
| attctgaatt | gtgaagttaa | tgcagatttg | gtcccatttg | ttaggtggga | acagaatcga | 600 |
| cagcccttc | ttctagatga | caggattgtc | aaacttccaa | gtggaacact | ggttatcagc | 660 |
| aatgctactg | aaggagatgg | gggactctac | cgctgcattg | ttgaaagtgg | tgggccacca | 720 |
| aagtttagtg | acgaagctga | attgaaagtt | cttcaagatc | ctgaggaaat | tgtagacttg | 780 |
| gtatttctga | tgcgaccatc | ttctatgatg | aaagtcactg | gtcagagtgc | agtgttgcca | 840 |
| tgtgttgtct | cagggcttcc | tgctccagtt | gttagatgga | tgaaaacga | agaagtgctt | 900 |
| gacacagaaa | gctctggcag | gttggtcttg | ctagcaggag | gttgcttgga | gatcagtgat | 960 |
| gtcactgagg | atgatgctgg | gacttatttt | tgcatagctg | ataatggaaa | taagacagtt | 1020 |
| gaagctcagg | cggagcttac | tgtgcaagtg | ccacctggat | tcctgaaaca | acctgctaac | 1080 |
| atatatgctc | acgaatccat | ggacattgta | tttgaatgtg | aagtcactgg | gaagccaact | 1140 |
| ccaactgtga | gtgggtcaa | gatgggggat | gtggttatcc | ccagtgatta | ctttaaaatt | 1200 |
| gtaaaggaac | ataatcttca | agttttgggt | ctggtgaaat | cagatgaagg | gttctatcaa | 1260 |
| tgcattgctg | agaatgatgt | tggaaatgca | caagctggag | cccagctgat | aatccttgag | 1320 |
| catgatgttg | ccatcccaac | attacctccc | acttcactga | ccagtgccac | tactgaccat | 1380 |
| ctagcaccag | ccacaacggg | accattacct | tcagctcctc | gagacgtcgt | ggcctccctg | 1440 |
| gtctctactc | gcttcattaa | attgacatgg | cgtacacctg | catcagaccc | tcatggagac | 1500 |
| aatctcacct | actctgtgtt | ctacaccaag | gaaggggttg | ctagggagcg | tgttgagaat | 1560 |
| accagccagc | caggagagat | gcaggtgact | attcaaaact | tgatgccagc | aactgtgtac | 1620 |
| atcttcaaag | ttatggctca | aaataagcat | ggctctggag | aaagttcagc | tcctcttcga | 1680 |
| gtagagacac | agcctgaggt | tcagctcct | ggcccagcac | ctaatatccg | tgcttatgca | 1740 |
| acgtcaccta | cttctatcac | tgtcacctgg | gaaacaccgt | atctggcaa | tggggaaatt | 1800 |
| caaaattaca | aattgtacta | catggaaaaa | ggaactgata | agaacagga | tattgatgtt | 1860 |
| tcaagtcact | cctacaccat | taatggactg | aagaaataca | cagaatacag | tttccgagtg | 1920 |
| gtggcctaca | ataaacatgg | tcctggagtt | tctacacaag | atgttgctgt | tcgaacatta | 1980 |

```
tcagatgttc ccagtgctgc tcctcagaat ctgtccttag aagtgagaaa ttcaaagagt    2040
atagtgatcc actggcagcc cccttcctca accacacaaa atgggcagat aactggctac    2100
aagattcgat atcgaaaggc ctcccgaaaa agtgatgtca ctgagacctt ggtaactggg    2160
acacagctgt ctcagctgat tgaaggtctt gatcggggga cagaatataa cttccgagtc    2220
gctgctctca cagtcaatgg tacaggtcca gcaactgatt ggctgtctgc tgaaactttt    2280
gaaagcgacc tagatgaaac tcgtgttcct gaagtgccca gctctcttca tgtccgtccg    2340
ctcgtcacta gcattgtagt gagctggact cctccagaga accagaacat tgtggtccga    2400
ggttatgcca tcggttacgg cattggcagc cctcatgccc agaccatcaa agtggactat    2460
aaacaacgtt attacaccat cgaaaacttg atccaagct ctcattacgt gattaccttg     2520
aaagcattta acaatgttgg cgaaggcatc cccctttatg agagtgctgt gaccagacct    2580
cacacagtgc cagatcccac tcccatgatg ccaccagtgg gagttcaggc ttccattctg    2640
agtcacgaca ccataaggat tacctgggca gacaactccc tgcccaaaca ccagaagatt    2700
acagactccc gctactacac agtccggtgg aagaccaaca tcccagcaaa cacgaagtac    2760
aagaatgcaa atgcaacgac gttaagctat ttggttactg gtttaaagcc aaatacgctc    2820
tatgagttct ctgtgatggt gaccaaaggc agaaggtcaa gcacgtggag tatgacagct    2880
catggcgcta cctttgaatt agttcctact tctccaccta aggatgtgac agttgtgagt    2940
aaggaaggaa aacctagaac catcatagtg aattggcagc ctccctctga agctaacggc    3000
aagattacag gttacatcat ctattacagc acggatgtga atgcagagat acatgactgg    3060
gttattgaac cagttgtggg aaacagactg actcaccaga ttcaagagtt aacacttgat    3120
acgccatact acttcaaaat ccaggcccgg aactcaaagg gcatggggcc catgtctgaa    3180
gctgtacagt tcagaacacc taaagcctta gggtcagcag gaaaaggaag ccgactacca    3240
gacctgggat ctgactacaa acctccaatg agtggcagca acagccctca cgggagcccc    3300 acctccctc tggacagcaa catgctgctg gtcatcattg tctctgttgg cgtcatcact    3360
atcgtggtgg ttgtggtcat tgctgtcttt tgtacccggc gcaccacctc tcaccagaag    3420
aagaaacgag ctgcgtgcaa atcagtgaat ggctcccata agtacaaggg caattgcaaa    3480
gatgtgaagc ctccagacct atggatccat cacgagagac tagagttgaa gcctattgac    3540
aagtctccag atcctaaccc tgtcatgact gatactccaa tccctcgaaa ctctcaagat    3600
atcacaccag tggacaattc catggatagc aatatccatc aaaggcggaa ttcatacaga    3660
gggcatgagt cagaggacag catgtctaca ctggctggaa ggaggggaat gagaccaaaa    3720
atgatgatgc cctttgactc tcagccacct cagcctgtga ttagtgccca tcccatccat    3780
tccctcgata cccctcacca tcatttccac tccagcagcc tcgcttctcc agcccgcagt    3840
catctctacc acccaagcag cccatggccc attggcacat ccatgtccct ttcagacagg    3900
gccaattcca cagaatctgt tcgaaatacc cccagcacgg acaccatgcc agcgtcctcg    3960
tctcagacgt gctgcactga ccatcaggac cctgagggtg ctactagctc ctcttacttg    4020
gccagctccc aagaggaaga ctcaggccag agtcttccca gcccatgt ccgcccttcc     4080 cacccctctga agagcttcgc tgtgccagca atcccacccc caggacctcc tctctatgat    4140
cctgcactgc caagcacacc attactgtcc cagcaagctc tgaaccatca cattcactca    4200
gtgaaaacag cctccatcgg gacgttagga aggagccggc ctcctatgcc agtggttgtt    4260
ccgagtgccc tgaagtaca ggagaccacc aggatgctgg aagactccga gagtagctat    4320
gaaccagatg agctgaccaa agagatggcc cacctggaag gactaatgaa ggacctaaat    4380
```
gccatcacaa cagcctga 4398

<210> SEQ ID NO 12
<211> LENGTH: 1465
<212> TYPE: PRT
<213> ORGANISM: Mus musculus

<400> SEQUENCE: 12

Met Ala Ala Glu Arg Glu Ala Gly Arg Leu Leu Cys Thr Ser Ser Ser
1               5                   10                  15

Arg Arg Cys Cys Pro Pro Pro Leu Leu Leu Leu Pro Leu Leu
            20                  25                  30

Leu Leu Leu Gly Arg Pro Ala Ser Gly Ala Ala Thr Lys Ser Gly
        35                  40                  45

Ser Pro Pro Gln Ser Ala Gly Ala Ser Val Arg Thr Phe Thr Pro Phe
50                  55                  60

Tyr Phe Leu Val Glu Pro Val Asp Thr Leu Ser Val Arg Gly Ser Ser
65                  70                  75                  80

Val Ile Leu Asn Cys Ser Ala Tyr Ser Glu Pro Ser Pro Asn Ile Glu
                85                  90                  95

Trp Lys Lys Asp Gly Thr Phe Leu Asn Leu Glu Ser Asp Asp Arg Arg
            100                 105                 110

Gln Leu Leu Pro Asp Gly Ser Leu Phe Ile Ser Asn Val Val His Ser
        115                 120                 125

Lys His Asn Lys Pro Asp Glu Gly Phe Tyr Gln Cys Val Ala Thr Val
130                 135                 140

Asp Asn Leu Gly Thr Ile Val Ser Arg Thr Ala Lys Leu Thr Val Ala
145                 150                 155                 160

Gly Leu Pro Arg Phe Thr Ser Gln Pro Glu Pro Ser Ser Val Tyr Val
                165                 170                 175

Gly Asn Ser Ala Ile Leu Asn Cys Glu Val Asn Ala Asp Leu Val Pro
            180                 185                 190

Phe Val Arg Trp Glu Gln Asn Arg Gln Pro Leu Leu Leu Asp Asp Arg
        195                 200                 205

Ile Val Lys Leu Pro Ser Gly Thr Leu Val Ile Ser Asn Ala Thr Glu
210                 215                 220

Gly Asp Gly Gly Leu Tyr Arg Cys Ile Val Glu Ser Gly Gly Pro Pro
225                 230                 235                 240

Lys Phe Ser Asp Glu Ala Glu Leu Lys Val Leu Gln Asp Pro Glu Glu
                245                 250                 255

Ile Val Asp Leu Val Phe Leu Met Arg Pro Ser Ser Met Met Lys Val
            260                 265                 270

Thr Gly Gln Ser Ala Val Leu Pro Cys Val Val Ser Gly Leu Pro Ala
        275                 280                 285

Pro Val Val Arg Trp Met Lys Asn Glu Glu Val Leu Asp Thr Glu Ser
290                 295                 300

Ser Gly Arg Leu Val Leu Leu Ala Gly Gly Cys Leu Glu Ile Ser Asp
305                 310                 315                 320

Val Thr Glu Asp Asp Ala Gly Thr Tyr Phe Cys Ile Ala Asp Asn Gly
                325                 330                 335

Asn Lys Thr Val Glu Ala Gln Ala Glu Leu Thr Val Gln Val Pro Pro
            340                 345                 350

Gly Phe Leu Lys Gln Pro Ala Asn Ile Tyr Ala His Glu Ser Met Asp
        355                 360                 365

```
Ile Val Phe Glu Cys Glu Val Thr Gly Lys Pro Thr Pro Thr Val Lys
    370                 375                 380

Trp Val Lys Asn Gly Asp Val Val Ile Pro Ser Asp Tyr Phe Lys Ile
385                 390                 395                 400

Val Lys Glu His Asn Leu Gln Val Leu Gly Leu Val Lys Ser Asp Glu
                405                 410                 415

Gly Phe Tyr Gln Cys Ile Ala Glu Asn Asp Val Gly Asn Ala Gln Ala
            420                 425                 430

Gly Ala Gln Leu Ile Ile Leu Glu His Asp Val Ala Ile Pro Thr Leu
        435                 440                 445

Pro Pro Thr Ser Leu Thr Ser Ala Thr Thr Asp His Leu Ala Pro Ala
    450                 455                 460

Thr Thr Gly Pro Leu Pro Ser Ala Pro Arg Asp Val Val Ala Ser Leu
465                 470                 475                 480

Val Ser Thr Arg Phe Ile Lys Leu Thr Trp Arg Thr Pro Ala Ser Asp
                485                 490                 495

Pro His Gly Asp Asn Leu Thr Tyr Ser Val Phe Tyr Thr Lys Glu Gly
            500                 505                 510

Val Ala Arg Glu Arg Val Glu Asn Thr Ser Gln Pro Gly Glu Met Gln
        515                 520                 525

Val Thr Ile Gln Asn Leu Met Pro Ala Thr Val Tyr Ile Phe Lys Val
    530                 535                 540

Met Ala Gln Asn Lys His Gly Ser Gly Glu Ser Ser Ala Pro Leu Arg
545                 550                 555                 560

Val Glu Thr Gln Pro Glu Val Gln Leu Pro Gly Pro Ala Pro Asn Ile
                565                 570                 575

Arg Ala Tyr Ala Thr Ser Pro Thr Ser Ile Thr Val Thr Trp Glu Thr
            580                 585                 590

Pro Leu Ser Gly Asn Gly Glu Ile Gln Asn Tyr Lys Leu Tyr Tyr Met
        595                 600                 605

Glu Lys Gly Thr Asp Lys Glu Gln Asp Ile Asp Val Ser Ser His Ser
    610                 615                 620

Tyr Thr Ile Asn Gly Leu Lys Lys Tyr Thr Glu Tyr Ser Phe Arg Val
625                 630                 635                 640

Val Ala Tyr Asn Lys His Gly Pro Gly Val Ser Thr Gln Asp Val Ala
                645                 650                 655

Val Arg Thr Leu Ser Asp Val Pro Ser Ala Ala Pro Gln Asn Leu Ser
            660                 665                 670

Leu Glu Val Arg Asn Ser Lys Ser Ile Val Ile His Trp Gln Pro Pro
        675                 680                 685

Ser Ser Thr Thr Gln Asn Gly Gln Ile Thr Gly Tyr Lys Ile Arg Tyr
    690                 695                 700

Arg Lys Ala Ser Arg Lys Ser Asp Val Thr Glu Thr Leu Val Thr Gly
705                 710                 715                 720

Thr Gln Leu Ser Gln Leu Ile Glu Gly Leu Asp Arg Gly Thr Glu Tyr
                725                 730                 735

Asn Phe Arg Val Ala Ala Leu Thr Val Asn Gly Thr Gly Pro Ala Thr
            740                 745                 750

Asp Trp Leu Ser Ala Glu Thr Phe Glu Ser Asp Leu Asp Glu Thr Arg
        755                 760                 765

Val Pro Glu Val Pro Ser Ser Leu His Val Arg Pro Leu Val Thr Ser
    770                 775                 780
```

```
Ile Val Val Ser Trp Thr Pro Pro Glu Asn Gln Asn Ile Val Val Arg
785                 790                 795                 800

Gly Tyr Ala Ile Gly Tyr Gly Ile Gly Ser Pro His Ala Gln Thr Ile
            805                 810                 815

Lys Val Asp Tyr Lys Gln Arg Tyr Tyr Thr Ile Glu Asn Leu Asp Pro
        820                 825                 830

Ser Ser His Tyr Val Ile Thr Leu Lys Ala Phe Asn Asn Val Gly Glu
            835                 840                 845

Gly Ile Pro Leu Tyr Glu Ser Ala Val Thr Arg Pro His Thr Val Pro
    850                 855                 860

Asp Pro Thr Pro Met Met Pro Pro Val Gly Val Gln Ala Ser Ile Leu
865                 870                 875                 880

Ser His Asp Thr Ile Arg Ile Thr Trp Ala Asp Asn Ser Leu Pro Lys
            885                 890                 895

His Gln Lys Ile Thr Asp Ser Arg Tyr Tyr Thr Val Arg Trp Lys Thr
        900                 905                 910

Asn Ile Pro Ala Asn Thr Lys Tyr Lys Asn Ala Asn Ala Thr Thr Leu
    915                 920                 925

Ser Tyr Leu Val Thr Gly Leu Lys Pro Asn Thr Leu Tyr Glu Phe Ser
    930                 935                 940

Val Met Val Thr Lys Gly Arg Arg Ser Ser Thr Trp Ser Met Thr Ala
945                 950                 955                 960

His Gly Ala Thr Phe Glu Leu Val Pro Thr Ser Pro Lys Asp Val
            965                 970                 975

Thr Val Val Ser Lys Glu Gly Lys Pro Arg Thr Ile Ile Val Asn Trp
            980                 985                 990

Gln Pro Pro Ser Glu Ala Asn Gly  Lys Ile Thr Gly Tyr  Ile Ile Tyr
        995                 1000                 1005

Tyr Ser  Thr Asp Val Asn Ala  Glu Ile His Asp Trp  Val Ile Glu
    1010                 1015                 1020

Pro Val  Val Gly Asn Arg Leu  Thr His Gln Ile Gln  Glu Leu Thr
    1025                 1030                 1035

Leu Asp  Thr Pro Tyr Tyr Phe  Lys Ile Gln Ala Arg  Asn Ser Lys
    1040                 1045                 1050

Gly Met  Gly Pro Met Ser Glu  Ala Val Gln Phe Arg  Thr Pro Lys
    1055                 1060                 1065

Ala Leu  Gly Ser Ala Gly Lys  Gly Ser Arg Leu Pro  Asp Leu Gly
    1070                 1075                 1080

Ser Asp  Tyr Lys Pro Pro Met  Ser Gly Ser Asn Ser  Pro His Gly
    1085                 1090                 1095

Ser Pro  Thr Ser Pro Leu Asp  Ser Asn Met Leu Leu  Val Ile Ile
    1100                 1105                 1110

Val Ser  Val Gly Val Ile Thr  Ile Val Val Val Val  Val Ile Ala
    1115                 1120                 1125

Val Phe  Cys Thr Arg Arg Thr  Thr Ser His Gln Lys  Lys Lys Arg
    1130                 1135                 1140

Ala Ala  Cys Lys Ser Val Asn  Gly Ser His Lys Tyr  Lys Gly Asn
    1145                 1150                 1155

Cys Lys  Asp Val Lys Pro Pro  Asp Leu Trp Ile His  His Glu Arg
    1160                 1165                 1170

Leu Glu  Leu Lys Pro Ile Asp  Lys Ser Pro Asp Pro  Asn Pro Val
    1175                 1180                 1185

Met Thr  Asp Thr Pro Ile Pro  Arg Asn Ser Gln Asp  Ile Thr Pro
```

| | | | | | | | | | | |
|---|---|---|---|---|---|---|---|---|---|---|
| | | 1190 | | | 1195 | | | 1200 | | |
| Val | Asp | Asn | Ser | Met | Asp | Ser | Asn | Ile | His | Gln | Arg | Arg | Asn | Ser |
| | | 1205 | | | | | 1210 | | | | | 1215 | | |
| Tyr | Arg | Gly | His | Glu | Ser | Glu | Asp | Ser | Met | Ser | Thr | Leu | Ala | Gly |
| | | 1220 | | | | | 1225 | | | | | 1230 | | |
| Arg | Arg | Gly | Met | Arg | Pro | Lys | Met | Met | Met | Pro | Phe | Asp | Ser | Gln |
| | | 1235 | | | | | 1240 | | | | | 1245 | | |
| Pro | Pro | Gln | Pro | Val | Ile | Ser | Ala | His | Pro | Ile | His | Ser | Leu | Asp |
| | | 1250 | | | | | 1255 | | | | | 1260 | | |
| Asn | Pro | His | His | His | Phe | His | Ser | Ser | Ser | Leu | Ala | Ser | Pro | Ala |
| | | 1265 | | | | | 1270 | | | | | 1275 | | |
| Arg | Ser | His | Leu | Tyr | His | Pro | Ser | Ser | Pro | Trp | Pro | Ile | Gly | Thr |
| | | 1280 | | | | | 1285 | | | | | 1290 | | |
| Ser | Met | Ser | Leu | Ser | Asp | Arg | Ala | Asn | Ser | Thr | Glu | Ser | Val | Arg |
| | | 1295 | | | | | 1300 | | | | | 1305 | | |
| Asn | Thr | Pro | Ser | Thr | Asp | Thr | Met | Pro | Ala | Ser | Ser | Ser | Gln | Thr |
| | | 1310 | | | | | 1315 | | | | | 1320 | | |
| Cys | Cys | Thr | Asp | His | Gln | Asp | Pro | Glu | Gly | Ala | Thr | Ser | Ser | Ser |
| | | 1325 | | | | | 1330 | | | | | 1335 | | |
| Tyr | Leu | Ala | Ser | Ser | Gln | Glu | Glu | Asp | Ser | Gly | Gln | Ser | Leu | Pro |
| | | 1340 | | | | | 1345 | | | | | 1350 | | |
| Thr | Ala | His | Val | Arg | Pro | Ser | His | Pro | Leu | Lys | Ser | Phe | Ala | Val |
| | | 1355 | | | | | 1360 | | | | | 1365 | | |
| Pro | Ala | Ile | Pro | Pro | Pro | Gly | Pro | Pro | Leu | Tyr | Asp | Pro | Ala | Leu |
| | | 1370 | | | | | 1375 | | | | | 1380 | | |
| Pro | Ser | Thr | Pro | Leu | Leu | Ser | Gln | Gln | Ala | Leu | Asn | His | His | Ile |
| | | 1385 | | | | | 1390 | | | | | 1395 | | |
| His | Ser | Val | Lys | Thr | Ala | Ser | Ile | Gly | Thr | Leu | Gly | Arg | Ser | Arg |
| | | 1400 | | | | | 1405 | | | | | 1410 | | |
| Pro | Pro | Met | Pro | Val | Val | Val | Pro | Ser | Ala | Pro | Glu | Val | Gln | Glu |
| | | 1415 | | | | | 1420 | | | | | 1425 | | |
| Thr | Thr | Arg | Met | Leu | Glu | Asp | Ser | Glu | Ser | Ser | Tyr | Glu | Pro | Asp |
| | | 1430 | | | | | 1435 | | | | | 1440 | | |
| Glu | Leu | Thr | Lys | Glu | Met | Ala | His | Leu | Glu | Gly | Leu | Met | Lys | Asp |
| | | 1445 | | | | | 1450 | | | | | 1455 | | |
| Leu | Asn | Ala | Ile | Thr | Thr | Ala |
| | | 1460 | | | 1465 | |

<210> SEQ ID NO 13
<211> LENGTH: 1191
<212> TYPE: DNA
<213> ORGANISM: Homo sapiens

<400> SEQUENCE: 13

```
atggtggccg ggacccgctg tcttctagcg ttgctgcttc cccaggtcct cctgggcggc      60
gcggctggcc tcgttccgga gctgggccgc aggaagttcg cggcggcgtc gtcgggccgc     120
ccctcatccc agccctctga cgaggtcctg agcgagttcg agttgcggct gctcagcatg     180
ttcggcctga acagagacc cacccccagc agggacgccg tggtgccccc ctacatgcta     240
gacctgtatc gcaggcactc aggtcagccg ggctcacccg ccccagacca ccggttggag     300
agggcagcca gccgagccaa cactgtgcgc agcttccacc atgaagaatc tttggaagaa     360
ctaccagaaa cgagtgggaa acaacccgg agattcttct ttaatttaag ttctatcccc     420
acggaggagt ttatcaccctc agcagagctt caggtttttcc gagaacagat gcaagatgct     480
```

```
ttaggaaaca atagcagttt ccatcaccga attaatattt atgaaatcat aaaacctgca    540
acagccaact cgaaattccc cgtgaccaga cttttggaca ccaggttggt gaatcagaat    600
gcaagcaggt gggaaagttt tgatgtcacc cccgctgtga tgcggtggac tgcacaggga    660
cacgccaacc atggattcgt ggtggaagtg gcccacttgg aggagaaaca aggtgtctcc    720
aagagacatg ttaggataag caggtctttg caccaagatg aacacagctg gtcacagata    780
aggccattgc tagtaacttt tggccatgat ggaaaagggc atcctctcca caaagagaa     840 aaacgtcaag ccaaacacaa acagcggaaa cgccttaagt ccagctgtaa gagacaccct    900
ttgtacgtgg acttcagtga cgtggggtgg aatgactgga ttgtggctcc cccggggtat    960
cacgcctttt actgccacgg agaatgccct tttcctctgg ctgatcatct gaactccact   1020
aatcatgcca ttgttcagac gttggtcaac tctgttaact ctaagattcc taaggcatgc   1080
tgtgtcccga cagaactcag tgctatctcg atgctgtacc ttgacgagaa tgaaaaggtt   1140
gtattaaaga actatcagga catggttgtg gagggttgtg ggtgtcgcta g            1191
```

<210> SEQ ID NO 14
<211> LENGTH: 396
<212> TYPE: PRT
<213> ORGANISM: Homo sapiens

<400> SEQUENCE: 14

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
```

```
                    245                 250                 255
Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
            325                 330                 335

Leu Asn Ser Thr Asn His Ala Ile Val Gln Thr Leu Val Asn Ser Val
        340                 345                 350

Asn Ser Lys Ile Pro Lys Ala Cys Cys Val Pro Thr Glu Leu Ser Ala
    355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 15
<211> LENGTH: 1185
<212> TYPE: DNA
<213> ORGANISM: Mus musculus

<400> SEQUENCE: 15
atggtggccg ggacccgctg tcttctagtg ttgctgcttc cccaggtcct cctgggcggc      60
gcggccggcc tcattccaga gctgggccgc aagaagttcg ccgcggcatc cagccgaccc     120
ttgtcccggc cttcggaaga cgtcctcagc gaatttgagt tgaggctgct cagcatgttt     180
ggcctgaagc agagacccac ccccagcaag gacgtcgtgg tgccccccta tatgctagat     240
ctgtaccgca ggcactcagg ccagccagga gcgcccgccc cagaccaccg gctggagagg     300
gcagccagcc gcgccaacac cgtgcgcagc ttccatcacg aagaagccgt ggaggaactt     360
ccagagatga gtgggaaaac ggcccggcgc ttcttcttca atttaagttc tgtccccagt     420
gacgagtttc tcacatctgc agaactccag atcttccggg aacagataca ggaagctttg     480
ggaaacagta gtttccagca ccgaattaat atttatgaaa ttataaagcc tgcagcagcc     540
aacttgaaat ttcctgtgac cagactattg gacaccaggt tagtgaatca gaacacaagt     600
cagtgggaga gcttcgacgt caccccagct gtgatgcggt ggaccacaca gggacacacc     660
aaccatgggt tgtggtgga agtggcccat ttagaggaga cccaggtgt ctccaagaga     720 catgtgagga ttagcaggtc tttgcaccaa gatgaacaca gctggtcaca gataaggcca     780
ttgctagtga cttttggaca tgatggaaaa ggacatccgc tccacaaacg agaaaagcgt     840
caagccaaac acaaacagcg gaagcgcctc aagtccagct gcaagagaca ccctttgtat     900
gtggacttca gtgatgtggg gtggaatgac tggatcgtgg cacctccggg ctatcatgcc     960
ttttactgcc atggggagtg tcctttccc cttgctgacc acctgaactc cactaaccat    1020
gccatagtgc agactctggt gaactctgtg aattccaaaa tccctaaggc atgctgtgtc    1080
cccacagagc tcagcgcaat ctccatgttg tacctagatg aaaatgaaaa ggttgtgcta    1140
aaaaattatc aggacatggt tgtggagggc tgcgggtgtc gttag                    1185

<210> SEQ ID NO 16
```

```
<211> LENGTH: 394
<212> TYPE: PRT
<213> ORGANISM: Mus musculus

<400> SEQUENCE: 16
```

| | | | | | | | | | | | | | | |
|---|---|---|---|---|---|---|---|---|---|---|---|---|---|---|
| Met<br>1 | Val | Ala | Gly | Thr<br>5 | Arg | Cys | Leu | Leu | Val<br>10 | Leu | Leu | Pro | Gln | Val<br>15 |
| Leu | Leu | Gly | Gly<br>20 | Ala | Ala | Gly | Leu | Ile<br>25 | Pro | Glu | Leu | Gly | Arg<br>30 | Lys Lys |
| Phe | Ala | Ala<br>35 | Ala | Ser | Ser | Arg | Pro<br>40 | Leu | Ser | Arg | Pro | Ser<br>45 | Glu | Asp Val |
| Leu | Ser<br>50 | Glu | Phe | Glu | Leu | Arg<br>55 | Leu | Leu | Ser | Met | Phe<br>60 | Gly | Leu | Lys Gln |
| Arg<br>65 | Pro | Thr | Pro | Ser | Lys<br>70 | Asp | Val | Val | Pro | Pro<br>75 | Tyr | Met | Leu | Asp<br>80 |
| Leu | Tyr | Arg | Arg | His<br>85 | Ser | Gly | Gln | Pro | Gly<br>90 | Ala | Pro | Ala | Pro<br>95 | Asp His |
| Arg | Leu | Glu | Arg<br>100 | Ala | Ala | Ser | Arg | Ala<br>105 | Asn | Thr | Val | Arg | Ser<br>110 | Phe His |
| His | Glu | Glu<br>115 | Ala | Val | Glu | Glu | Leu<br>120 | Pro | Glu | Met | Ser | Gly<br>125 | Lys | Thr Ala |
| Arg | Arg<br>130 | Phe | Phe | Phe | Asn | Leu<br>135 | Ser | Ser | Val | Pro | Ser<br>140 | Asp | Glu | Phe Leu |
| Thr<br>145 | Ser | Ala | Glu | Leu | Gln<br>150 | Ile | Phe | Arg | Glu | Gln<br>155 | Ile | Gln | Glu | Ala Leu<br>160 |
| Gly | Asn | Ser | Ser | Phe<br>165 | Gln | His | Arg | Ile | Asn<br>170 | Ile | Tyr | Glu | Ile | Ile Lys<br>175 |
| Pro | Ala | Ala | Ala<br>180 | Asn | Leu | Lys | Phe | Pro<br>185 | Val | Thr | Arg | Leu | Leu<br>190 | Asp Thr |
| Arg | Leu | Val<br>195 | Asn | Gln | Asn | Thr | Ser<br>200 | Gln | Trp | Glu | Ser | Phe<br>205 | Asp | Val Thr |
| Pro | Ala<br>210 | Val | Met | Arg | Trp | Thr<br>215 | Thr | Gln | Gly | His | Thr<br>220 | Asn | His | Gly Phe |
| Val<br>225 | Val | Glu | Val | Ala | His<br>230 | Leu | Glu | Glu | Asn | Pro<br>235 | Gly | Val | Ser | Lys Arg<br>240 |
| His | Val | Arg | Ile | Ser<br>245 | Arg | Ser | Leu | His | Gln<br>250 | Asp | Glu | His | Ser | Trp Ser<br>255 |
| Gln | Ile | Arg | Pro<br>260 | Leu | Leu | Val | Thr | Phe<br>265 | Gly | His | Asp | Gly | Lys<br>270 | Gly His |
| Pro | Leu | His<br>275 | Lys | Arg | Glu | Lys | Arg<br>280 | Gln | Ala | Lys | His | Lys<br>285 | Gln | Arg Lys |
| Arg | Leu<br>290 | Lys | Ser | Ser | Cys | Lys<br>295 | Arg | His | Pro | Leu | Tyr<br>300 | Val | Asp | Phe Ser |
| Asp<br>305 | Val | Gly | Trp | Asn | Asp<br>310 | Trp | Ile | Val | Ala | Pro<br>315 | Pro | Gly | Tyr | His Ala<br>320 |
| Phe | Tyr | Cys | His | Gly<br>325 | Glu | Cys | Pro | Phe | Pro<br>330 | Leu | Ala | Asp | His | Leu Asn<br>335 |
| Ser | Thr | Asn | His<br>340 | Ala | Ile | Val | Gln | Thr<br>345 | Leu | Val | Asn | Ser | Val<br>350 | Asn Ser |
| Lys | Ile | Pro<br>355 | Lys | Ala | Cys | Cys | Val<br>360 | Pro | Thr | Glu | Leu | Ser<br>365 | Ala | Ile Ser |
| Met<br>370 | Leu | Tyr | Leu | Asp | Glu<br>375 | Asn | Glu | Lys | Val | Val<br>380 | Leu | Lys | Asn | Tyr Gln |
| Asp | Met | Val | Val | Glu | Gly | Cys | Gly | Cys | Arg | | | | | |

<210> SEQ ID NO 17
<211> LENGTH: 1227
<212> TYPE: DNA
<213> ORGANISM: Homo sapiens

<400> SEQUENCE: 17

```
atgattcctg gtaaccgaat gctgatggtc gttttattat gccaagtcct gctaggaggc      60
gcgagccatg ctagtttgat acctgagacg gggaagaaaa aagtcgccga gattcagggc     120
cacgcgggag gacgccgctc agggcagagc catgagctcc tgcgggactt cgaggcgaca     180
cttctgcaga tgtttgggct gcgccgccgc ccgcagccta gcaagagtgc cgtcattccg     240
gactacatgc gggatcttta ccggcttcag tctggggagg aggaggaaga gcagatccac     300
agcactggtc ttgagtatcc tgagcgcccg gccagccggg ccaacaccgt gaggagcttc     360
caccacgaag aacatctgga gaacatccca gggaccagtg aaaactctgc ttttcgtttc     420
ctctttaacc tcagcagcat ccctgagaac gaggtgatct cctctgcaga gcttcggctc     480
ttccgggagc aggtggacca gggccctgat tgggaagggg gcttccaccg tataaacatt     540
tatgaggtta tgaagccccc agcagaagtg gtgcctgggc acctcatcac acgactactg     600
gacacgagac tggtccacca caatgtgaca cggtgggaaa cttttgatgt gagccctgcg     660
gtccttcgct ggacccggga gaagcagcca aactatgggc tagccattga ggtgactcac     720
ctccatcaga ctcggaccca ccagggccag catgtcagga ttagccgatc gttacctcaa     780
gggagtggga attgggccca gctccggccc tcctggtca cctttggcca tgatggccgg     840
ggccatgcct tgacccgacg ccggagggcc aagcgtagcc ctaagcatca ctcacagcgg     900
gccaggaaga agaataagaa ctgccggcgc cactcgctct atgtggactt cagcgatgtg     960
ggctggaatg actggattgt ggccccacca ggctaccagg ccttctactg ccatgggggac    1020
tgcccctttc cactggctga ccacctcaac tcaaccaacc atgccattgt gcagaccctg    1080
gtcaattctg tcaattccag tatccccaaa gcctgttgtg tgcccactga actgagtgcc    1140
atctccatgc tgtacctgga tgagtatgat aaggtggtac tgaaaaatta tcaggagatg    1200
gtagtagagg gatgtgggtg ccgctga                                        1227
```

<210> SEQ ID NO 18
<211> LENGTH: 1227
<212> TYPE: DNA
<213> ORGANISM: Homo sapiens

<400> SEQUENCE: 18

```
atgattcctg gtaaccgaat gctgatggtc gttttattat gccaagtcct gctaggaggc      60
gcgagccatg ctagtttgat acctgagacg gggaagaaaa aagtcgccga gattcagggc     120
cacgcgggag gacgccgctc agggcagagc catgagctcc tgcgggactt cgaggcgaca     180
cttctgcaga tgtttgggct gcgccgccgc ccgcagccta gcaagagtgc cgtcattccg     240
gactacatgc gggatcttta ccggcttcag tctggggagg aggaggaaga gcagatccac     300
agcactggtc ttgagtatcc tgagcgcccg gccagccggg ccaacaccgt gaggagcttc     360
caccacgaag aacatctgga gaacatccca gggaccagtg aaaactctgc ttttcgtttc     420
ctctttaacc tcagcagcat ccctgagaac gaggtgatct cctctgcaga gcttcggctc     480
ttccgggagc aggtggacca gggccctgat tgggaagggg gcttccaccg tataaacatt     540
tatgaggtta tgaagccccc agcagaagtg gtgcctgggc acctcatcac acgactactg     600
```

```
gacacgagac tggtccacca caatgtgaca cggtggga aa cttttgatgt gagccctgcg    660
gtccttcgct ggacccggga gaagcagcca aactatgggc tagccattga ggtgactcac    720
ctccatcaga ctcggaccca ccagggccag catgtcagga ttagccgatc gttacctcaa    780
gggagtggga attgggccca gctccggccc ctcctggtca cctttggcca tgatggccgg    840
ggccatgcct tgacccgacg ccggagggcc aagcgtagcc ctaagcatca ctcacagcgg    900
gccaggaaga agaataagaa ctgccggcgc cactcgctct atgtggactt cagcgatgtg    960
ggctggaatg actggattgt ggccccacca ggctaccagg ccttctactg ccatggggac   1020
tgcccctttc cactggctga ccacctcaac tcaaccaacc atgccattgt gcagaccctg   1080
gtcaattctg tcaattccag tatccccaaa gcctgttgtg tgcccactga actgagtgcc   1140
atctccatgc tgtacctgga tgagtatgat aaggtggtac tgaaaaatta tcaggagatg   1200
gtagtagagg gatgtgggtg ccgctga                                       1227

<210> SEQ ID NO 19
<211> LENGTH: 1227
<212> TYPE: DNA
<213> ORGANISM: Homo sapiens

<400> SEQUENCE: 19
atgattcctg gtaaccgaat gctgatggtc gttttattat gccaagtcct gctaggaggc     60
gcgagccatg ctagtttgat acctgagacg gggaagaaaa aagtcgccga gattcagggc    120
cacgcgggag gacgccgctc agggcagagc catgagctcc tgcgggactt cgaggcgaca    180
cttctgcaga tgtttgggct gcgccgccgc ccgcagccta gcaagagtgc cgtcattccg    240
gactacatgc gggatcttta ccggcttcag tctggggagg aggaggaaga gcagatccac    300
agcactggtc ttgagtatcc tgagcgcccg gccagccggg ccaacaccgt gaggagcttc    360
caccacgaag aacatctgga gaacatccca gggaccagtg aaaactctgc ttttcgtttc    420
ctctttaacc tcagcagcat ccctgagaac gaggtgatct cctctgcaga gcttcggctc    480
ttccgggagc aggtggacca gggccctgat tgggaaaggg gcttccaccg tataaacatt    540
tatgaggtta tgaagccccc agcagaagtg gtgcctgggc acctcatcac acgactactg    600
gacacgagac tggtccacca caatgtgaca cggtggga aa cttttgatgt gagccctgcg    660
gtccttcgct ggacccggga gaagcagcca aactatgggc tagccattga ggtgactcac    720
ctccatcaga ctcggaccca ccagggccag catgtcagga ttagccgatc gttacctcaa    780
gggagtggga attgggccca gctccggccc ctcctggtca cctttggcca tgatggccgg    840
ggccatgcct tgacccgacg ccggagggcc aagcgtagcc ctaagcatca ctcacagcgg    900
gccaggaaga agaataagaa ctgccggcgc cactcgctct atgtggactt cagcgatgtg    960
ggctggaatg actggattgt ggccccacca ggctaccagg ccttctactg ccatggggac   1020
tgcccctttc cactggctga ccacctcaac tcaaccaacc atgccattgt gcagaccctg   1080
gtcaattctg tcaattccag tatccccaaa gcctgttgtg tgcccactga actgagtgcc   1140
atctccatgc tgtacctgga tgagtatgat aaggtggtac tgaaaaatta tcaggagatg   1200
gtagtagagg gatgtgggtg ccgctga                                       1227

<210> SEQ ID NO 20
<211> LENGTH: 408
<212> TYPE: PRT
<213> ORGANISM: Homo sapiens
```

```
<400> SEQUENCE: 20

Met Ile Pro Gly Asn Arg Met Leu Met Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Ser Gly
            35                  40                  45

Gln Ser His Glu Leu Leu Arg Asp Phe Glu Ala Thr Leu Leu Gln Met
    50                  55                  60

Phe Gly Leu Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
            115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
    195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405
```

<210> SEQ ID NO 21
<211> LENGTH: 1227
<212> TYPE: DNA
<213> ORGANISM: Mus musculus

<400> SEQUENCE: 21

```
atgattcctg gtaaccgaat gctgatggtc gttttattat gccaagtcct gctaggaggc    60
gcgagccatg ctagtttgat acctgagacc gggaagaaaa agtcgccga gattcagggc    120
cacgcgggag gacgccgctc agggcagagc catgagctcc tgcgggactt cgaggcgaca    180
cttctacaga tgtttgggct gcgccgccgt ccgcagccta gcaagagcgc cgtcattccg    240
gattacatga gggatcttta ccggctccag tctggggagg aggaggagga agagcagagc    300
cagggaaccg gcttgagta cccggagcgt cccgccagcc gagccaacac tgtgaggagt    360
ttccatcacg aagaacatct ggagaacatc ccagggacca gtgagagctc tgcttttcgt    420
ttcctcttca acctcagcag catcccagag aatgaggtga tctcctcggc agagctccgg    480
ctctttcggg agcaggtgga ccagggccct gactgggaac agggcttcca ccgtataaac    540
atttatgagg ttatgaagcc cccagcagaa atggttcctg acacctcat cacacgacta    600
ctggacacca gactagtcca tcacaatgtg acacggtggg aaactttcga tgtgagccct    660
gcagtccttc gctggacccg ggaaaagcaa cccaattatg ggctggccat tgaggtgact    720
cacctccacc agacacggac ccaccagggc cagcacgtca gaatcagccg atcgttacct    780
caagggagtg gagattgggc ccaactccgg cccctcctgg tcacttttgg ccatgatggc    840
cggggccata ccttgacccg cagaagggcc aaacgtagtc ccaagcatca cccacagcgg    900
tccaggaaga gaataagaa ctgccgtcgc cattcactat acgtggactt cagtgacgtg    960
ggctggaatg attggattgt ggccccaccc ggctaccagg ccttctactg ccacggggac    1020
tgtcccttc cactggctga tcacctcaac tcaaccaacc atgccattgt gcagaccccta  1080
gtcaactctg ttaattctag tatccctaag gcctgttgtg tccccactga actgagtgcc   1140
atttccatgt tgtacctgga tgagtatgac aaggtggtgt tgaaaaatta tcaggagatg   1200
gtggtagagg ggtgtggatg ccgctga                                       1227
```

<210> SEQ ID NO 22
<211> LENGTH: 408
<212> TYPE: PRT
<213> ORGANISM: Mus musculus

<400> SEQUENCE: 22

```
Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Glu Gln Ser Gln Gly Thr Gly Leu Glu Tyr Pro Glu Arg Pro Ala
            100                 105                 110
```

```
Ser Arg Ala Asn Thr Val Arg Ser Phe His His Glu Glu His Leu Glu
        115                 120                 125

Asn Ile Pro Gly Thr Ser Glu Ser Ser Ala Phe Arg Phe Leu Phe Asn
        130                 135                 140

Leu Ser Ser Ile Pro Glu Asn Glu Val Ile Ser Ser Ala Glu Leu Arg
145                 150                 155                 160

Leu Phe Arg Glu Gln Val Asp Gln Gly Pro Asp Trp Glu Gln Gly Phe
                165                 170                 175

His Arg Ile Asn Ile Tyr Glu Val Met Lys Pro Pro Ala Glu Met Val
                180                 185                 190

Pro Gly His Leu Ile Thr Arg Leu Leu Asp Thr Arg Leu Val His His
                195                 200                 205

Asn Val Thr Arg Trp Glu Thr Phe Asp Val Ser Pro Ala Val Leu Arg
        210                 215                 220

Trp Thr Arg Glu Lys Gln Pro Asn Tyr Gly Leu Ala Ile Glu Val Thr
225                 230                 235                 240

His Leu His Gln Thr Arg Thr His Gln Gly Gln His Val Arg Ile Ser
                245                 250                 255

Arg Ser Leu Pro Gln Gly Ser Gly Asp Trp Ala Gln Leu Arg Pro Leu
        260                 265                 270

Leu Val Thr Phe Gly His Asp Gly Arg Gly His Thr Leu Thr Arg Arg
        275                 280                 285

Arg Ala Lys Arg Ser Pro Lys His His Pro Gln Arg Ser Arg Lys Lys
290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
                340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
        370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 23
<211> LENGTH: 819
<212> TYPE: DNA
<213> ORGANISM: Homo sapiens
<220> FEATURE:
<221> NAME/KEY: CDS
<222> LOCATION: (1)..(819)

<400> SEQUENCE: 23 atg atc ttc ctc ctg cta atg ttg agc ctg gaa ttg cag ctt cac cag     48
Met Ile Phe Leu Leu Leu Met Leu Ser Leu Glu Leu Gln Leu His Gln
1               5                   10                  15 ata gca gct tta ttc aca gtg aca gtc cct aag gaa ctg tac ata ata     96
Ile Ala Ala Leu Phe Thr Val Thr Val Pro Lys Glu Leu Tyr Ile Ile
                20                  25                  30 gag cat ggc agc aat gtg acc ctg gaa tgc aac ttt gac act gga agt    144
Glu His Gly Ser Asn Val Thr Leu Glu Cys Asn Phe Asp Thr Gly Ser
```

```
cat gtg aac ctt gga gca ata aca gcc agt ttg caa aag gtg gaa aat      192
His Val Asn Leu Gly Ala Ile Thr Ala Ser Leu Gln Lys Val Glu Asn
     50                  55                  60 gat aca tcc cca cac cgt gaa aga gcc act ttg ctg gag gag cag ctg      240
Asp Thr Ser Pro His Arg Glu Arg Ala Thr Leu Leu Glu Glu Gln Leu
 65                  70                  75                  80 ccc cta ggg aag gcc tcg ttc cac ata cct caa gtc caa gtg agg gac      288
Pro Leu Gly Lys Ala Ser Phe His Ile Pro Gln Val Gln Val Arg Asp
                 85                  90                  95 gaa gga cag tac caa tgc ata atc atc tat ggg gtc gcc tgg gac tac      336
Glu Gly Gln Tyr Gln Cys Ile Ile Ile Tyr Gly Val Ala Trp Asp Tyr
            100                 105                 110 aag tac ctg act ctg aaa gtc aaa gct tcc tac agg aaa ata aac act      384
Lys Tyr Leu Thr Leu Lys Val Lys Ala Ser Tyr Arg Lys Ile Asn Thr
        115                 120                 125 cac atc cta aag gtt cca gaa aca gat gag gta gag ctc acc tgc cag      432
His Ile Leu Lys Val Pro Glu Thr Asp Glu Val Glu Leu Thr Cys Gln
    130                 135                 140 gct aca ggt tat cct ctg gca gaa gta tcc tgg cca aac gtc agc gtt      480
Ala Thr Gly Tyr Pro Leu Ala Glu Val Ser Trp Pro Asn Val Ser Val
145                 150                 155                 160 cct gcc aac acc agc cac tcc agg acc cct gaa ggc ctc tac cag gtc      528
Pro Ala Asn Thr Ser His Ser Arg Thr Pro Glu Gly Leu Tyr Gln Val
                165                 170                 175 acc agt gtt ctg cgc cta aag cca ccc cct ggc aga aac ttc agc tgt      576
Thr Ser Val Leu Arg Leu Lys Pro Pro Pro Gly Arg Asn Phe Ser Cys
            180                 185                 190 gtg ttc tgg aat act cac gtg agg gaa ctt act ttg gcc agc att gac      624
Val Phe Trp Asn Thr His Val Arg Glu Leu Thr Leu Ala Ser Ile Asp
        195                 200                 205 ctt caa agt cag atg gaa ccc agg acc cat cca act tgg ctg ctt cac      672
Leu Gln Ser Gln Met Glu Pro Arg Thr His Pro Thr Trp Leu Leu His
    210                 215                 220 att ttc atc ccc tcc tgc atc att gct ttc att ttc ata gcc aca gtg      720
Ile Phe Ile Pro Ser Cys Ile Ile Ala Phe Ile Phe Ile Ala Thr Val
225                 230                 235                 240 ata gcc cta aga aaa caa ctc tgt caa aag ctg tat tct tca aaa gac      768
Ile Ala Leu Arg Lys Gln Leu Cys Gln Lys Leu Tyr Ser Ser Lys Asp
                245                 250                 255 aca aca aaa aga cct gtc acc aca aca aag agg gaa gtg aac agt gct      816
Thr Thr Lys Arg Pro Val Thr Thr Thr Lys Arg Glu Val Asn Ser Ala
            260                 265                 270 atc                                                                  819
Ile

<210> SEQ ID NO 24
<211> LENGTH: 273
<212> TYPE: PRT
<213> ORGANISM: Homo sapiens

<400> SEQUENCE: 24

Met Ile Phe Leu Leu Leu Met Leu Ser Leu Glu Leu Gln Leu His Gln
 1               5                  10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
```

```
                50                  55                  60
Asp Thr Ser Pro His Arg Glu Arg Ala Thr Leu Leu Glu Glu Gln Leu
 65                  70                  75                  80

Pro Leu Gly Lys Ala Ser Phe His Ile Pro Gln Val Gln Val Arg Asp
                 85                  90                  95

Glu Gly Gln Tyr Gln Cys Ile Ile Ile Tyr Gly Val Ala Trp Asp Tyr
                100                 105                 110

Lys Tyr Leu Thr Leu Lys Val Lys Ala Ser Tyr Arg Lys Ile Asn Thr
                115                 120                 125

His Ile Leu Lys Val Pro Glu Thr Asp Glu Val Glu Leu Thr Cys Gln
                130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
                180                 185                 190

Val Phe Trp Asn Thr His Val Arg Glu Leu Thr Leu Ala Ser Ile Asp
                195                 200                 205

Leu Gln Ser Gln Met Glu Pro Arg Thr His Pro Thr Trp Leu Leu His
                210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
                260                 265                 270

Ile

<210> SEQ ID NO 25
<211> LENGTH: 126
<212> TYPE: PRT
<213> ORGANISM: Artificial Sequence
<220> FEATURE:
<223> OTHER INFORMATION: /note="Description of Artificial Sequence: 9D1
      mAb vK amino acid sequence"

<400> SEQUENCE: 25

Met Met Ala Ala Val Gln Leu Leu Gly Leu Leu Leu Leu Cys Leu Arg
 1               5                  10                  15

Ala Met Arg Cys Asp Ile Gln Met Thr Gln Ser Pro Ser His Leu Ser
                20                  25                  30

Ala Ser Val Gly Asp Arg Val Thr Leu Ser Cys Lys Val Ser Gln Asn
                35                  40                  45

Ile Tyr Lys Tyr Leu Asn Trp Tyr Gln Gln Lys Leu Gly Glu Ala Pro
 50                  55                  60

Lys Leu Leu Ile Tyr Tyr Thr Ser Phe Leu Gln Thr Gly Ile Pro Ser
 65                  70                  75                  80

Arg Phe Ser Gly Ser Gly Ser Gly Thr Asp Tyr Thr Leu Thr Ile Ser
                 85                  90                  95

Ser Leu Gln Pro Glu Asp Val Ala Thr Tyr Phe Cys Gln Lys Tyr Tyr
                100                 105                 110

Ser Gly Trp Thr Phe Gly Gly Gly Thr Lys Leu Glu Leu Lys
                115                 120                 125
```

```
<210> SEQ ID NO 26
<211> LENGTH: 378
<212> TYPE: DNA
<213> ORGANISM: Artificial Sequence
<220> FEATURE:
<223> OTHER INFORMATION: /note="Description of Artificial Sequence: 9D1
      mAb vK cDNA sequence"

<400> SEQUENCE: 26
atgatggctg cagttcagct cttagggctt tgctgctct gcctccgagc catgagatgt        60
gacatccaga tgacccagtc tccttcacac ctgtcagcat ctgtgggaga cagagtcact       120
ctcagctgca agtaagtca gaatatttac aagtacttaa actggtatca gcaaaaactt       180
ggagaagctc ccaaactcct gatatattat acaagctttt tgcaaacggg catcccgtca       240
aggttcagtg gcagtggatc tggtacagat tacacactca ccatcagcag cctgcagcct       300
gaagatgttg ccacatattt ctgccagaag tattatagcg ggtggacgtt cggtggaggc       360
accaagctgg aattgaaa                                                    378

<210> SEQ ID NO 27
<211> LENGTH: 136
<212> TYPE: PRT
<213> ORGANISM: Artificial Sequence
<220> FEATURE:
<223> OTHER INFORMATION: /note="Description of Artificial Sequence: 9D1
      mAb vH amino acid sequence"

<400> SEQUENCE: 27

Met Gly Trp Ser Gln Ile Ile Leu Phe Leu Val Ala Ala Thr Thr Cys
1               5                   10                  15

Val His Ser Gln Val Gln Leu Gln Gln Ser Gly Thr Glu Leu Val Lys
            20                  25                  30

Pro Gly Ser Ser Val Lys Ile Ser Cys Lys Ala Ser Gly Asp Thr Phe
        35                  40                  45

Thr Ser Asp Tyr Met His Trp Ile Arg Gln Pro Gly Ser Gly Leu
    50                  55                  60

Glu Trp Ile Gly Trp Ile Tyr Pro Gly Asn Gly Asn Thr Lys Tyr Asn
65                  70                  75                  80

Gln Lys Phe Asp Gly Lys Ala Thr Leu Thr Ala Asp Lys Ser Ser Ser
                85                  90                  95

Thr Ala Tyr Leu Gln Leu Ser Leu Leu Thr Ser Glu Asp Tyr Ala Val
            100                 105                 110

Tyr Phe Cys Ala Arg Gln Thr Glu Gly Tyr Phe Asp Tyr Trp Gly Gln
        115                 120                 125

Gly Val Met Val Thr Val Ser Ser
    130                 135

<210> SEQ ID NO 28
<211> LENGTH: 408
<212> TYPE: DNA
<213> ORGANISM: Artificial Sequence
<220> FEATURE:
<223> OTHER INFORMATION: /note="Description of Artificial Sequence: 9D1
      mAb vH cDNA sequence"

<400> SEQUENCE: 28
atgggatgga gccagatcat tctctttctg gtggcagcaa ctacatgtgt ccactcccag        60
gtacagctac agcaatcagg gactgaactg gtgaagcctg gtcctcagt gaaaatttcc       120 tgcaaggctt ctggcgacac cttcaccagt gactatatgc actggataag gcagcagcct       180
```

```
ggaagtggcc ttgagtggat tgggtggatt tatcctggaa atggtaatac taagtacaat         240
caaaagttcg atgggaaggc aacactcact gcagacaaat cctccagcac agcctatttg         300
cagctcagcc tcctgacatc tgaggactat gcagtctatt tctgtgcaag acagacggag         360
gggtactttg attactgggg ccaaggagtc atggtcacag tctcctca                     408
```